US006482410B1

(12) United States Patent
Crossin et al.

(10) Patent No.: US 6,482,410 B1
(45) Date of Patent: *Nov. 19, 2002

(54) CYTOTACTIN DERIVATIVES THAT STIMULATE ATTACHMENT AND NEURITE OUTGROWTH, AND METHODS OF MAKING SAME

(75) Inventors: Kathryn L. Crossin, San Diego; Greg Phillips, Del Mar; Anne L. Prieto, San Diego, all of CA (US)

(73) Assignee: The Scripps Research Institute, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/793,273

(22) PCT Filed: Sep. 14, 1995

(86) PCT No.: PCT/US95/11684

§ 371 (c)(1),
(2), (4) Date: May 22, 1997

(87) PCT Pub. No.: WO96/08513

PCT Pub. Date: Mar. 21, 1996

Related U.S. Application Data

(63) Continuation-in-part of application No. 08/308,359, filed on Sep. 19, 1994, now abandoned.

(51) Int. Cl.$^7$ .................... C07K 14/78; A61K 38/39
(52) U.S. Cl. ............... 424/185.1; 530/350; 424/198.1; 424/192.1; 424/195.11; 424/425; 424/426
(58) Field of Search .................. 530/350, 399, 530/324; 514/12; 930/10; 424/185.1, 192.1, 198.1, 195.11, 425, 426, 484, 491, 499

(56) References Cited

U.S. PATENT DOCUMENTS 4,829,000 A * 5/1989 Kleinman et al. ...... 435/240.23
5,279,966 A * 1/1994 Jessell et al. ............ 435/320.1

OTHER PUBLICATIONS

Friedlander, et al., "Functional Mapping of Cytotactin: Proteolytic Fragments Active in Cell–Substrate Adhesion", *J. Cell Biol.*, 107:2329–2340 (1988).

Husmann, et al., "Tenascin Promotes Cerebellar Granule Cell Migration and Neurite Outgrowth by Different Domains in the Fibronectin Type III Repeats", *J. Cell Biol.*, 116:1475–1486 (1992).

Jones, et al., "A cDNA Clone for Cytotactin Contains Sequences Similar to Epidermal Growth Factor–like Repeats and Segments of Fibronectin and Fibrinogen", *Proc. Natl. Acad. Sci., USA*, 85:2186–2190 (1988).

Jones, et al., "A Detailed Structural Model of Cytotactin: Protein Homologies Alternative RNA Splicing, and Binding Regions", *Proc. Natl. Acad. Sci., USA*, 86:1905–1909 (1989).

Nies, et al., "The Complete cDNA Sequence of Human Hexabrachion (Tenascin)", *J. Biol. Chem.*, 266:2818–2823 (1991).

Prieto, et al., "Characterization of Multiple Adhesive and Counteradhesive Domains in the Extracellular Matrix Protein Cytotactin", *J. Cell Biol.*, 119:663–678 (1992).

Spring, et al., "Two Contrary Functions of Tenascin: Dissection of the Active Sites by Recombinant Tenascin Fragments", *Cell*, 59:325–334 (1989).

Taylor, et al., "Influence of Janusin and Tenascin on Growth Cone Behavior In Vitro", *J. Neuroscience Res.*, 35:347–362 (1993).

Wehrle–Haller, et al., "Dual function of Tenascin: Simultaneous Promotion of Neurite Growth and Inhibition of Glial Migration", *J. Cell Science*, 106:597–610 (1993).

Siji et al Nucleic Acids Research 19(1991) 525–531.*

Weller et al. J. Cell Biology 112 (1991) 355–362.*

Rudinger In "Peptide Hormones" (Jun. 1976) ed. J.A. Parsons, University Park Press, Baltimore, pp.1–7.*

* cited by examiner

*Primary Examiner*—Gary L. Kunz
*Assistant Examiner*—Robert C. Hayes
(74) *Attorney, Agent, or Firm*—Emily Holmes; Thomas Fitting

(57) ABSTRACT

The present invention relates to cytotactin proteins, polypeptides, antibodies (including anti-idiotype antibodies), and other cytotacting derivatives useful in the mediation of neuronal attachment and enhancement of the outgrowth of neurites, as well as to methods of using same. Methods of making the disclosed proteins, polypeptides, antibodies, derivatives and related compositions, which have a variety of diagnostic and therapeutic applications, are also disclosed.

9 Claims, 3 Drawing Sheets

CYTOTACTIN DERIVATIVES THAT STIMULATE ATTACHMENT AND NEURITE OUTGROWTH, AND METHODS OF MAKING SAME

This application is the National Stage under 35 U.S.C. 371 of International Application No. PCT/US95/11684, filed Sep. 14, 1995, which is a continuation-in-part of U.S. application Ser. No. 08/308,359, filed Sep. 19, 1994, now abandoned.

This invention was made with government support under Contract No. DK04256 by the National Institutes of Health. The government has certain rights in the invention.

TECHNICAL FIELD

The present invention relates to cytotactin proteins, polypeptides, antibodies and other cytotactin derivatives useful in the mediation of neuronal attachment and enhancement of the outgrowth of neurites, as well as to methods of using same. Methods of making the disclosed proteins, polypeptides, antibodies, derivatives and related compositions, which have a variety of diagnostic and therapeutic applications, are also disclosed.

BACKGROUND

Cytotactin (CT) is a multidomain extracellular matrix (ECM) protein which plays a role in cell migration, proliferation, and differentiation during development (Crossin, et al., *J. Cell Biol.* 102: 1917–1930(1986); Prieto, et al., *J. Cell Biol.* 111: 685–698 (1990)), which may be controlled by other developmentally important genes. The restricted spatiotemporal expression of cytotactin that results from its developmental regulation is tightly linked to a number of cellular primary processes, including adhesion (Grumet, et al., *Proc. Natl. Acad. Sci. USA* 82: 8075–8079 (1985)), migration (Chuong et al.,*J. Cell Biol.* 104: 331–342 (1987); Halfter, et al.,*Dev. Biol.* 132: 14–25 (1989); Tan, et al., *PNAS USA* 84: 7977–7981 (1987)), proliferation (Chiquet-Ehrismann, et al., *Cell* 53: 383–390 (1988); Crossin, *PNAS USA* 88: 11403–11407 (1991)), differentiation (Mackie, et al., *J. Cell Biol.* 105: 2569–2579 (1987)), epithelial-mesenchymal interactions (Aufderheide, et al., *J. Cell Biol.* 105: 2341–2349 (1988); Aufderheide, et al., *J. Cell Biol.* 105: 599–608 (1987)), and cell death (Williamson, et al., *Embryonic Develop. Morphol.* 209: 189–202 (1991)).

Cytotactin, which is also known as tenascin (TN) (Chiquet-Ehrismann, et al., *Cell* 47: 131–139 (1986)), J1 2201200 (Kruse, et al., *Nature* 316: 146–148 (1985)), hexabrachion (Erickson, et al.,*Nature* 311: 267–269 (1984); Gulcher, et al., *PNAS USA* 86: 1588–1592 (1989)), the glioma-mesenchymal extracellular matrix protein (Bourdon, et al., *Cancer Res.* 43: 2796–2805 (1983)), and myotendinous antigen (Chiquet et al., *J. Cell Biol.* 98: 1926–1936 (1984)), exists in at least three isoforms generated by alternative splicing (Zisch, et al., *J. Cell Biol.* 119: 203 (1992)). The three known chicken CT isoforms, which are composed of polypeptides having molecular weights of 190, 200, and 220 kD have been isolated from chicken brain (Grumet, et al., *PNAS USA* 82: 8075–8079 (1985)); relative to the 190 kD isoform, the 200 kD form contains one, and the 220 kD form contains three, additional fn type III domains (Zisch, Id, (1992)). The CT found in other species, including human and murine CT, for example, exists in a variety of isoforms as well.

As noted, variation in the polypeptide structure arises from alternative splicing of transcripts from a single gene (Jones, et al., *PNAS USA* 85: 2186–2190 (1988); Jones, et al., *PNAS USA* 86: 1905–1909 (1989); Spring, et al., *Cell* 59: 325–334 (1989)). The polypeptides are disulfide-linked to form a multimeric structure (Grumet, et al., *PNAS USA* 82: 8075–8079 (1985); Hoffman, et al., *J. Cell Biol.* 106: 519–532 (1988)). Electron microscopy of the rotary-shadowed molecule has revealed a characteristic six-armed structure, called a hexabrachion (Erickson, et al., *Nature* 311: 267–269 (1984); Erickson, et al., *Adv. Cell Biol.* 2: 55–90 (1988)), in which six polypeptides are linked through disulfide bonds at their aminotermini.

The sequence of cytotactin reveals a multidomain structure (Jones, et al.,*PNAS USA* 86: 1905–1909 (1989); Spring, et al., *Cell* 59: 325–334 (1989)) with homologies to three other protein families. The amino-terminal portion contains the cysteine involved in interchain disulfide bonding, followed by an array of 13 repeats of 31 amino acids in length that resemble those found in epidermal growth factor (EGF). These EGF-like repeats are followed by a variable number of repeats similar to fibronectin type III repeats. In the chicken, cytotactin polypeptides contain between 8 and 11 type III repeats as a consequence of alternative RNA splicing. Different variants have been shown to be expressed preferentially at certain times and anatomical sites during development (Prieto, et al., *J. Cell Biol.* 111: 685–698 (1990)) and they may have different binding or morphogenic functions (Kaptony, et al., *Development (Camb.)* 112: 605–614 (1991); Matsuoka, et al., *Cell Differ.* 32: 417–424 (1990); Murphy-Ullrich, et al.,*J. Cell Biol.* 115: 1127–1136 (1991)).

More recently, it has been shown that the third fibronectin type III (CTfn3) repeat can mediate RGD-dependent cell attachment via integrins $\alpha_v\beta_3$ and $\alpha_v\beta_6$ and that the whole molecule bound to a $\beta_1$ integrin but the binding site was not determined. The carboxy-terminal portion of cytotactin is homologous to the distal domain of the $\beta$ and $\gamma$ chains of fibrinogen and contains a putative $Ca^{2+}$ binding site.

Early studies of cell attachment to cytotactin-coated surfaces suggested that multiple modes of binding to the molecule existed. For example, fibroblasts bind both to intact cytotactin and to a chymotryptic fragment derived from the carboxy-terminal end of the protein (Friedlander, et al., *J. Cell Biol.* 107: 2329–2340 (1988)). These binding activities are inhibitable by peptides containing the amino acid sequence arginine-glycine-aspartic acid (RGD) and by antibodies to specific regions of the cytotactin protein. In contrast to their rounded cell morphology on intact cytotactin, cells exhibit a spread morphology on the chymotryptic fragment. Using a variety of recombinant fragments of cytotactin, a smaller region of the molecule has been identified as a cell binding site, but no spreading was observed (Spring, et al., *Cell* 59: 325–334 (1989)).

In these studies, a fragment in the amino-terminal region containing the EGF domains appeared to prevent cell binding to other substrates. Together, these observations suggested that at least two binding activities are present in intact cytotactin, one in the carboxy-terminal half of the protein, mediating cell attachment and flattening, and one in the amino-terminal portion, responsible for so-called anti-adhesive effects (Spring, et al., *Cell* 59: 325–334 (1989)) and rounding of cells exposed to the molecule (Chiquet-Ehrismann, et al., *Cell* 47: 131–139 (1986); Friedlander, et al., *J. Cell Biol.* 107: 2329–2340 (1988)). Studies on the effects of cytotactin on neural attachment and neurite outgrowth have suggested at least one additional interactive site on the molecule based on antibody inhibition studies (Crossin, et al., *Exp. Neurol.* 109: 6–18 (1990); Faissner, et al., Neuron 5: 627–637 (1990); Grierson, et al., *Dev. Brain Res.* 55: 11–19 (1990); Husmann, et al., *J. Cell Biol.* 116: 1475–1486(1992); Lochter, et al., *J. Cell Biol.* 113: 1159–1171 (1991); Wehrle, et al., *Development (Camb.)* 110: 401–415 (1990)).

BRIEF SUMMARY OF THE INVENTION

We have now unambiguously identified the regions of CT responsible for its ability to promote or to inhibit neurite outgrowth, as well as the regions primarily responsible for cell attachment and spreading. Understanding which regions of this complex protein are responsible for these various functions is essential to determine how the protein may affect neural development and regeneration. One working hypothesis is that the inhibition and promotion of neurite outgrowth may be mapped to specific domains of the protein and may be modulated by other CT binding proteins in the ECM. Fusion proteins have now been generated in the pGEX expression system comprising almost the entire linear structure of the protein and have now been expressed in bacteria. Other new constructs comprising portions of CT, some in unique combinations, are also disclosed herein.

Using these bacterially-generated fusion proteins, smaller domains within the CT protein (e.g., CTfn3) have now been identified that have the ability to promote neurite outgrowth. Another major contribution of the within-disclosed invention is the contribution to the understanding of the conditions under which CT facilitates or inhibits neurite outgrowth and the description of reagents useful in therapeutic interventions to improve neural regeneration.

Therefore, in one embodiment, the present invention contemplates a cytotactin (CT) polypeptide substantially homologous to at least a portion of the protein identified as SEQ ID NO 2 herein (human cytotactin encoded by SEQ ID NO 1), wherein the polypeptide comprises not more than 250 amino acid residues in length. In another variation, the CT polypeptide is substantially homologous to at least a portion of the protein identified as SEQ ID NO 4 herein (chicken cytotactin encoded by SEQ ID NO 3). In various embodiments, the CT polypeptides are capable of stimulating neuronal cell attachment, cell elongation, cell growth, neurite outgrowth, or a combination of the foregoing. In an alternative embodiment, a polypeptide of the present invention is capable of stimulating cell attachment to a substrate, or it may be incorporated into a bioabsorbable matrix.

The invention further contemplates a polypeptide substantially homologous to at least a portion of the protein identified as SEQ ID NO 2 or SEQ ID NO 4 herein (respectively human and chicken cytotactin respectively encoded by SEQ ID NO 1 and SEQ ID NO 3), wherein the polypeptide comprises not more than 250 amino acid residues in length, and wherein the polypeptide comprises a fusion of two or more segments of the protein identified as SEQ ID NO 2 or SEQ ID NO 4 herein. In various alternative embodiments, the polypeptide has an amino acid residue sequence selected from the group consisting of SEQ ID NO 5 (human cytotactin); SEQ ID NO 6 (mouse cytotactin); SEQ ID NO 7 (chicken cytotactin); SEQ ID NO 8 (human cytotactin); SEQ ID NO 9 (mouse cytotactin); and SEQ ID NO 10 (chicken cytotactin). In other variations, the polypeptide is selected from the group consisting of CTfn3, CTfn6, and CTfn3–6.

The present invention also contemplates a cytotactin (CT) polypeptide substantially homologous to at least a portion of the protein identified as SEQ ID NO 4 herein, wherein the polypeptide comprises not more than 250 amino acid residues in length. The various alternative embodiments and applications described hereinabove with respect to SEQ ID NO 2 are also contemplated with regard to SEQ ID NO 4.

In yet another embodiment, the present invention contemplates a biological material comprising a bioabsorbable matrix and an effective amount of a pharmacologically active agent capable of affecting cell attachment, cell growth, or neurite outgrowth. In one variation, the biological material further comprises a collagen gel. In another variation, the agent comprises a cytotactin derivative. In alternative embodiments, the cytotactin derivative comprises human cytotactin (SEQ ID NO 2) or chick cytotactin (SEQ ID NO 4).

In yet another variation pertaining to biological materials of the present invention, the cytotactin derivative comprises one or more cytotactin polypeptides. The invention further contemplates that the cytotactin polypeptides are selected from the group consisting of SEQ ID NO 5; SEQ ID NO 6; SEQ ID NO 7; SEQ ID NO 8; SEQ ID NO 9; and SEQ ID NO 10. Alternatively, the cytotactin polypeptides are selected from the group consisting of CTfn3, CTfn6, and CTfn3–6. Another embodiment contemplates that the cytotactin derivative comprises an anti-(CT idiotype) antibody.

The invention further contemplates that the matrix comprises a bioabsorbable biopolymer. In various embodiments, the biopolymer comprises one or more macromolecules selected from the group consisting of collagen, elastin, fibronectin, vitronectin, laminin, hyaluronic acid, chondroitin sulfate, dermatan sulfate, heparin sulfate, heparin, fibrin, cellulose, gelatin, polylysine, echinonectin, entactin, thrombospondin, uvomorulin, biglycan, decorin, and dextran. In another disclosed variation, the matrix further includes a substructure comprising freeze dried sponge, powders, films, flaked or broken films, aggregates, microspheres, fibers, fiber bundles, or a combination thereof. In yet another embodiment, the matrix further includes a solid support selected from the group consisting of a prosthetic device; a porous tissue culture insert; an implant; and a suture.

The within-disclosed invention also contemplates antibody compositions. In one variation, an antibody composition comprises antibody molecules capable of inhibiting neurite outgrowth, wherein the antibody molecules immunoreact with a CT polypeptide substantially homologous to at least a portion of the protein identified as SEQ ID NO 2 herein. In another variation, the CT polypeptide is substantially homologous to at least a portion of the protein identified as SEQ ID NO 4 herein.

Another embodiment contemplates that the antibody molecules also immunoreact with cytotactin. In other variations, the antibody molecules are monoclonal or polyclonal. In one disclosed embodiment, the CT polypeptide is selected from the group consisting of SEQ ID NO 5; SEQ ID NO 6; SEQ ID NO 7; SEQ ID NO 8; SEQ ID NO 9; and SEQ ID NO 10. In another variation, the CT polypeptide is selected from the group consisting of CTfn3, CTfn6, and CTfn3–6.

Another antibody composition contemplated herein comprises anti-(CT idiotype) antibody molecules capable of stimulating neurite outgrowth. In one embodiment, the anti-(CT idiotype) antibody molecules have an activity substantially similar to that of a polypeptide substantially homologous to at least a portion of a protein identified as SEQ ID NO 2 or SEQ ID NO 4 herein, wherein the polypeptide comprises not more than 250 amino acid residues in length. In another embodiment, the anti-(CT idiotype) antibody molecules have an activity substantially similar to that of a polypeptide selected from the group consisting of CTfn3, CTfn6, and CTfn3–6. In one variation, the anti-(CT idiotype) antibody molecules are monoclonal. In another, the antibodies are humanized.

The present invention also discloses methods for preparing solid supports useful in promoting neuronal cell growth and elongation (and/or neurite outgrowth), comprising coating or impregnating the solid support with a biological material including a cytotactin derivative capable of promoting the growth and elongation. In one disclosed variation, the biological material comprises a bioabsorbable biopolymer. In another variation, the solid support is selected from the group consisting of a porous tissue culture insert; a prosthetic device; an implant; and a suture.

In another embodiment, the solid support comprises a bioabsorbable biopolymer. In alternative variations, the biopolymer comprises one or more macromolecules selected from the group consisting of collagen, elastin, fibronectin, vitronectin, laminin, hyaluronic acid, chondroitin sulfate, dermatan sulfate, heparin sulfate, heparin, fibrin, cellulose, gelatin, polylysine, echinonectin, entactin, thrombospondin, uvomorulin, biglycan, decorin, and dextran. In another embodiment, the biological material further comprises at least one attachment factor. Another variant of the disclosed method contemplates that the attachment factor is selected from the group consisting of collagen (all types), fibronectin, gelatin, laminin, polylysine, vitronectin, cytotactin, echinonectin, entactin, thrombospondin, uvomorulin, biglycan, chondroitin sulfate, decorin, dermatan sulfate, heparin, and hyaluronic acid.

The present invention also encompasses a variety of diagnostic and therapeutic assays and kits. In one embodiment, an assay kit for the detection of tumors comprises in an amount sufficient to conduct at least one assay, an anti-cytotactin antibody. Further components in various embodiments include labeling means, samples of CT protein or polypeptide, anti-(CT idiotype) antibodies, and other CT derivatives, all in amounts sufficient to conduct at least one assay.

The invention also contemplates various compounds and compositions useful in the detection or inhibition of metastasis or angiogenesis. One embodiment contemplates a site-specific anti-CT antibody capable of inhibiting metastasis in an individual. Another discloses a polypeptide capable of inhibiting metastasis and angiogenesis in an individual via modulating cell attachment to cytotactin.

The present invention also discloses various methods of detecting tumors. One method comprises obtaining a fluid or tissue sample from an individual; admixing the sample with a predetermined amount of an anti-cytotactin antibody to form an admixture; maintaining the admixture for a time period sufficient to allow the antibody to immunoreact with any cytotactin or fragments thereof in the sample, to form an immunoreaction product; assaying for the presence of the immunoreaction product; and comparing the amount of immunoreaction product assayed with a control, thereby determining whether an excessive amount of cytotactin is present in the sample.

Cell culture systems and methods are also contemplated herein. In one embodiment, a cell culture system comprising a substrate with a cell adhesion factor attached thereto is disclosed. In another, the adhesion factor comprises a CT derivative. Yet another discloses that the CT derivative is selected from the group consisting of SEQ ID NO 2; SEQ ID NO 4; SEQ ID NO 5; SEQ ID NO 6; SEQ ID NO 7; SEQ ID NO 8; SEQ ID NO 9; and SEQ ID NO 10.

A method of inhibiting cytotactin binding to neuronal cells in a patient is also disclosed, comprising administering to the patient a physiologically tolerable composition comprising a therapeutically effective amount of a CT derivative. In one alternative embodiment, the CT derivative is an antibody; in another, it is an anti-(CT idiotype) antibody. In still another variation, the therapeutically effective amount is an amount sufficient to produce an intravascular concentration of antibody in the blood of the patient in the range of about 0.1 to 100 μg/ml. Yet another variation contemplates that the CT derivative is a CT polypeptide substantially homologous to at least a portion of the protein identified as SEQ ID NO 2 herein.

In various disclosed embodiments, a therapeutically effective amount is an amount sufficient to produce an intravascular concentration of CT polypeptide in the blood of the patient in the range of about 0.1 to 100 micromolar. According to various embodiments, the neuronal cells are fibroblasts or ganglion cells.

Various compositions are also encompassed herein. In one embodiment, a composition comprises a therapeutically effective amount of a CT derivative in a pharmaceutically acceptable excipient, wherein the effective amount is an amount sufficient to inhibit cytotactin binding to neuronal cells. In another variation, the CT derivative is a CT polypeptide substantially homologous to at least a portion of the protein identified as SEQ ID NO 2 herein. Another embodiment contemplates that the effective amount is at least 0.1 weight percent of CT derivative per total weight of the composition. In various disclosed embodiments, the CT derivative is an anti-CT antibody or an anti-(CT idiotype) antibody.

The invention further contemplates methods of assaying the amount of cytotactin in a fluid sample. One such method comprises the steps of (a) admixing a fluid sample with an anti-CT antibody to form an immunoreaction admixture; (b) maintaining the admixture for a time period sufficient to form a CT-containing immunoreaction product in a solid phase; and (c) determining the amount of product formed in step (b). In another embodiment, the antibody is a monoclonal antibody; in yet another, the antibody is capable of immunoreacting with CTfn3 or CTfn6, or both.

In an alternative embodiment, the determining step (c) comprises the steps of (1) admixing the CT-containing immunoreaction product in the solid phase with a second antibody to form a second immunoreaction admixture having a liquid phase and a solid phase, the second antibody having the ability to immunoreact with the CT-containing immunoreaction product; (2) maintaining the second reaction admixture for a time period sufficient for the second antibody to immunoreact with the CT-containing immunoreaction product and form a second immunoreaction product in the solid phase; and (3) determining the amount of the second antibody present in the second immunoreaction product, thereby determining the amount of CT-containing immunoreaction product formed in step (c).

The present invention also discloses a competition assay method for assaying the amount of cytotactin in a fluid sample, comprising the steps of (a) forming a competition immunoreaction admixture by admixing a vascular fluid sample with (1) an anti-CT antibody composition containing antibody molecules that immunoreact with cytotactin and with a CT polypeptide substantially homologous to at least a portion of the protein identified as SEQ ID NO 2 herein, wherein the antibody molecules are attached to a solid matrix, such that the competition immunoreaction admixture has both a liquid and a solid phase; and (2) a polypeptide immunoreactive with the antibody, wherein the polypeptide is labeled; (b) maintaining the competition immunoreaction admixture for a time period sufficient to form a labeled immunoreaction product in the solid phase; and (c) determining the amount of labeled immunoreaction product formed in step (b), thereby determining the amount of cytotactin present in the sample. In one variation, the antibody is a monoclonal antibody. In alternative embodiments, the antibody is capable of immunoreacting with CTfn3, CTfn6, or both.

Finally, another preferred embodiment of the invention relates to polynucleotides which encode the above noted cytotactin proteins and polypeptides, and to polynucleotide sequences which are complementary to these polynucleotide sequences. Complementary polynucleotide sequences include those sequences which hybridize to the polynucleotide sequences of the invention under stringent hybridization conditions. Methods of making the various proteins, polypeptides, and other CT derivatives disclosed herein are also inventions disclosed herein.

The various regions of CT which were expressed as fusion proteins with glutathione-S-transferase (GST) in the pGEX protein expression system are shown below the primary structure and are labeled as they are presented in Example 1. The range of amino acid residues of chicken CT (SEQ ID NO 4) which corresponds to the various regions of CT expressed as fusion proteins with GST are given in Table 1.

Figure 2:
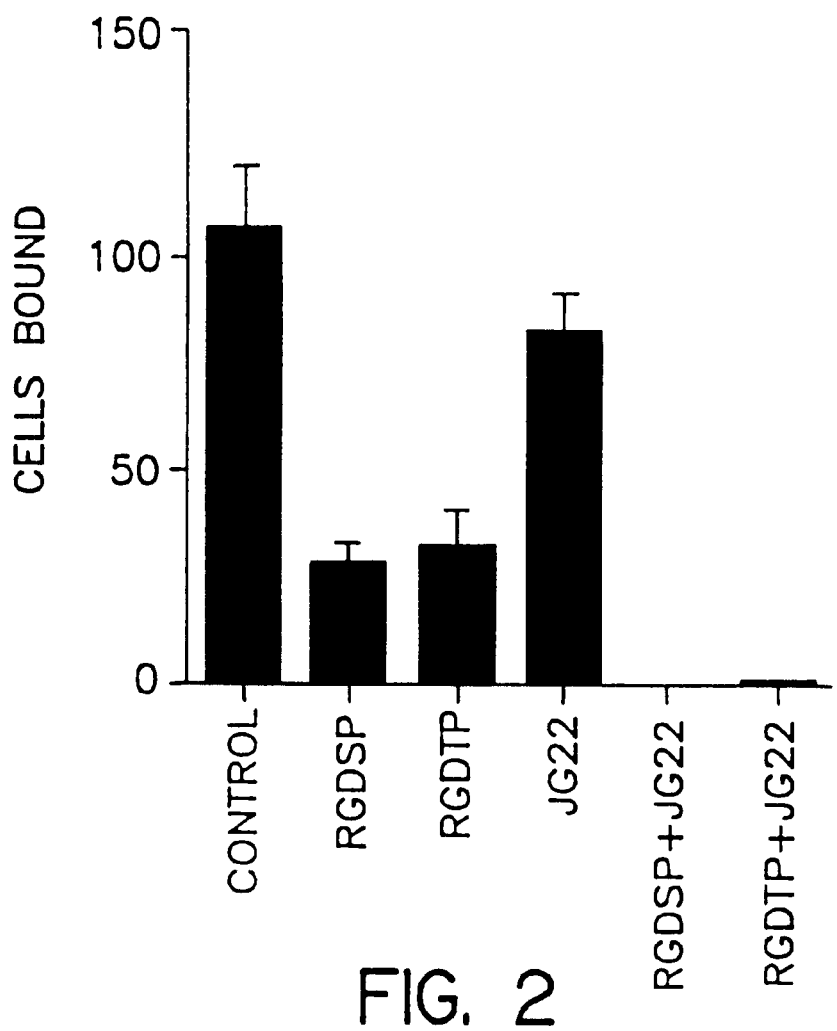

FIG. 2 illustrates the results of cell attachment and inhibition of cell attachment assays characterizing the attachment of chicken fibroblast cells to CT as described in Examples 5.B. and 5.C. Soluble inhibitors of attachment, the RGD-containing peptides Arg-Gly-Asp-Ser-Pro (RGDSP) (SEQ ID NO 11) and Arg-Gly-Asp-Thr-Pro (RGDTP) (SEQ ID NO 12), and the monoclonal antibody JG22, were assayed both separately and in combination for their ability to inhibit attachment of chicken fibroblast cells to CT as described in Example 5.C. The control sample represents the number of chicken fibroblast cells that attachment to CT in the absence of inhibitor. The number of cells bound is on the vertical axis and the inhibitors are given on the horizontal axis. The values represent the average of 12 measurements obtained in three separate experiments. Inhibition of attachment to CT was judged significant by the Student's t test where p=0.001.

Figure 3A:
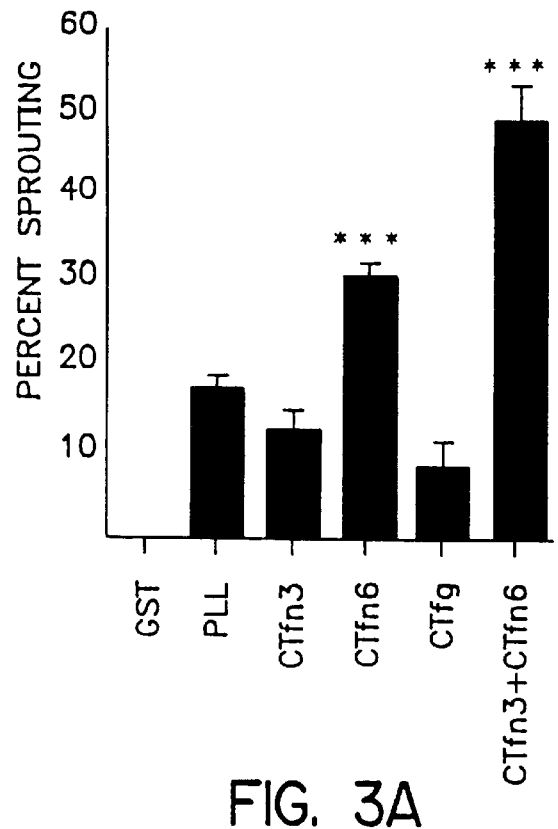
Figure 3B:
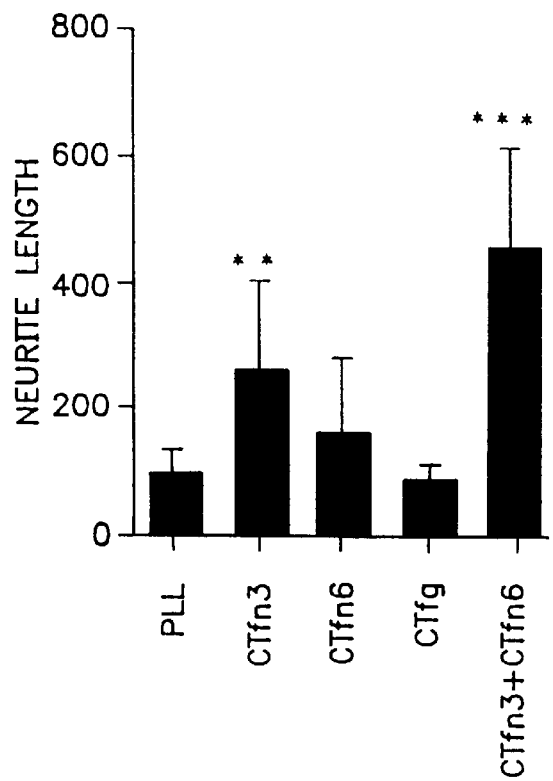

FIGS. 3A–B illustrates neurite outgrowth of dorsal root ganglia (DRG) when attached to control proteins, fusion proteins, and adhesion molecules as represented by the percent sprouting and neurite length as described in Example 6.C. In FIG. 3A, the vertical axis represents the percentage of cells sprouting neurites and the horizontal axis indicates the fusion protein or control used in the assay. GST represents the glutathione-S-transferase (GST) domain without a CT (CT) domain and PLL represents poly-L-lysine. CTfn3 and CTfn6 represent GST fusion proteins of the III and VI fibronectin type III repeats of CT, respectively. CTfg represents a GST fusion protein of the fibrinogen region of CT. CTfn3 and CTfn6 represents a combination of the GST fusion proteins, CTfn3 and CTfn6. The percent of cells sprouting was defined as those cells with neurites greater than one cell diameter and was derived from six experiments±standard deviation (S.E.M.).

In FIG. 3B, the vertical axis represents the length of the neurites in microns.

The average total neurite length per neurite-bearing cell was derived from three experiments±S.E.M. The horizontal axis represents the fusion protein or control used in the assay.

In FIGS. 3A and 3B, statistically significant differences from poly-L-lysine (PLL) are denoted by asterisks wherein  indicates p=0.005 and * indicates p=0.001.

DETAILED DESCRIPTION

A. Definitions

Amino Acid Residue: An amino acid, e.g., one formed upon chemical digestion (hydrolysis) of a polypeptide at its peptide linkages. The amino acid residues identified herein are preferably in the natural "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.* 243: 3552–59 (1969) and adopted at 37 CFR §1.822(b)(2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | Leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | unknown or any amino acid |
| B | Asx | aspartic acid or asparagine |
| Z | Glx | glutamic acid or glutamine |

It should be noted that all amino acid residue sequences are represented herein by formulae whose left and right orientation is in the conventional direction of amino-terminus to carboxy-terminus. In addition, the phrase "amino acid residue" is broadly defined to include modified and unusual amino acids, such as those listed in 37 CFR §1.822(b)(4), which disclosures are incorporated by reference herein. Furthermore, it should be noted that a dash (-) at the beginning or end of an amino acid residue sequence indicates either a peptide bond to a further sequence of one or more amino acid residues or a covalent bond to a carboxyl or hydroxyl end group.

Recombinant DNA (rDNA) molecule: A DNA molecule produced by operatively linking two or more DNA segments. Thus, a recombinant DNA molecule is a hybrid DNA molecule comprising at least two nucleotide sequences not normally found together in nature. Recombinant DNA molecules (rDNAs) not having a common biological origin, i.e., evolutionarily different, are said to be "heterologous".

Vector: A rDNA molecule capable of autonomous replication and to which a DNA segment, e.g., a gene or polynucleotide, can be operatively linked so as to bring about replication of the attached segment. Vectors capable of directing the expression of genes encoding for one or more polypeptides are referred to herein as "expression vectors". Particularly preferred vectors according to the present invention allow cloning of cDNA (complementary DNA) from messenger RNA (mRNA) produced using reverse transcriptase.

Receptor: A receptor is a biologically active proteinaceous molecule, such as a protein, glycoprotein, and the like, that can specifically (non-randomly) bind to a different molecule or molecules, generally termed ligand molecules.

Fusion Polypeptide: A polypeptide comprised of at least two polypeptides and a linking sequence which operatively links the polypeptides into one continuous polypeptide. The two or more polypeptides linked in a fusion polypeptide are typically derived from two independent sources, and therefore a fusion polypeptide comprises two or more linked polypeptides not normally found linked in nature. The terms "fusion protein(s)" and "fusion polypeptide(s)" may be used interchangeably herein.

Upstream: In the direction opposite to the direction of DNA transcription, that is, going from 5' to 3' on the non-coding strand, or 3' to 5' on the mRNA.

Downstream: Further along a DNA sequence in the direction of sequence transcription or read-out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Reading Frame: Particular sequence of contiguous nucleotide triplets (codons) employed in translation. The reading frame depends on the location of the translation initiation codon.

Antibody: The term "antibody" or "antibody molecule" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of heavy and light chain variable and hypervariable regions that specifically binds (immunoreacts with) an antigen. The term "immunoreact" in its various forms means specific binding between an antigenic determinant-containing molecule and a molecule containing an antibody combining site, such as a whole antibody molecule or a portion thereof.

Monoclonal Antibody: The phrases "monoclonal antibody" or "monoclonal antibody composition" in their various grammatical forms refer to a population of antibody molecules that contains only one species of antibody combining site capable of immunoreacting with a particular antigen. A monoclonal antibody thus typically displays a single binding affinity for any antigen with which it immunoreacts. Moreover, a monoclonal antibody may comprise an antibody molecule having a plurality of antibody combining sites, each site being immunospecific for a different antigen, e.g., a bispecific monoclonal antibody.

Polypeptide and Peptide: "polypeptide" and "peptide" are terms used interchangeably herein to designate a series of amino acid residues connected one to the other by peptide bonds between the alpha-amino and carboxy groups of adjacent residues. In general, the terms "peptide" and "polypeptide" are used herein to designate a series of 50 or fewer amino acid residues connected one to the other, while the term "protein" is used to designate a series of greater than 50 amino acid residues connected one to the other.

Synthetic Peptide: Synthetic peptide refers to a chemically produced polymer or chain of amino acid residues typically linked together by peptide bonds. As used herein, the term is not generally intended to include naturally occurring proteins and fragments thereof.

Conservative Substitution: "conservative substitution" as used herein denotes the replacement of an amino acid residue by another, biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. "Conservative substitution" is also intended to include differential splicing and repeats of various sequences, such as those seen in the various CT isoforms (e.g. those seen in human, murine and chick CT). The term "conservative substitution" as used herein also includes the use of a substituted amino acid in place of an unsubstituted parent amino acid provided that cytotactin homologs having the substituted polypeptide also stimulate cell attachment and/or neurite outgrowth.

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 75% similarity, preferably greater than 80% similarity, more preferably greater than 90% similarity, equivalent biological activity, and equivalent expression characteristics are considered substantially homologous and are included within the scope of proteins and polypeptides defined by the terms "cytotactin", "CT", "CT/TN", "CT derivative" and "CT peptide or polypeptide". Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents. Similarly, nucleotide sequences at least 75% homologous to that identified herein as SEQ ID NO 1 (human cytotactin nucleotide sequence) or to SEQ ID NO 3 (chicken cytotactin nucleotide sequence) (or a portion thereof) are considered substantially homologous.

B. Cytotactin and Cytotactin Derivatives

Cytotactin (CT) is a large extracellular matrix glycoprotein composed of several distinct domains. The amino terminus is a unique region containing cysteine residues that can form interchain disulfide bonds. In linear order, this is followed by several repeats similar to those in epidermal growth factor, by 6–15 repeats homologous to fibronectin (FN) type III repeats (the number depending on the species and on patterns of alternative splicing), and by a segment homologous to the β and γ chains of fibrinogen. (See, e.g., Jones, et al., *PNAS USA* 85: 2186–2190 (1988); Jones, et al., *PNAS USA* 86: 1905–1909 (1989); Gulcher, et al., *PNAS USA* 86: 1588–1592 (1989); Weller, et al., *J. Cell. Biol.* 112: 355–362 (1991); Spring, et al., *Cell* 59; 325–334 (1989).)

Although CT shows some structural similarities to FN, the two molecules differ both in their expression patterns and in their functions. For example, while glial and fibroblastic cells will attach to CT-coated substrates (Spring, et al., Id. (1989); Chiquet-Ehrismann, et al., *Cell* 53: 383–390 (1988); Hoffman, et al., *J. Cell Biol.* 106: 519–532 (1988); Friedlander, et al., *J. Cell Biol.* 107: 2329–2340 (1988)), CT prevents spreading of cells on FN or other permissive substrates (Chiquet-Ehrismann, et al., Id. (1 988); Friedlander, et al., Id. (1988)) and decreases cell migration (Tan, et al., Id. (1987); Mackie, et al., *Development (Cambridge, UK)* 102: 237–250 (1988) Kaplony, et al., *Development (Cambridge, UK)* 112: 605–614 (1991)).

The ability of CT to inhibit cell attachment, spreading, and migration has been termed counteradhesion (Prieto, et al., *J. Cell Biol.* 119: 663–678 (1992)), or antiadhesion (Spring, et al., Id. (1989)). This property is not unique to CT and is shared with at least three other extracellular matrix proteins, SPARC (Sage, et al., *J. Cell Biol.* 109: 341–356 (1989); Lane, et al., *J. Cell Biol.* 111: 3065–3076 (1990)), thrombospondin (Lawler, et al., *J. Cell Biol.* 107: 2351–2361 (1988); Murphy-Ullrich, et al., *J. Cell Biol.* 109: 1309–1319 (1989)) and laminin (Calof, et al., *J. Cell Biol.* 115: 779–794 (1991)).

A number of different studies have indicated that cytotactin (CT) affects neurite morphology and extension in vitro. (See, e.g., Crossin, et al., *Exp. Neurol.* 109: 6–18 (1990); Faissner and Kruse, *Neuron* 5: 627–637 (1990); Grierson, et al., *Dev Brain Res.* 55: 11–19 (1990); Husmann, et al., *J. Cell. Biol.* 116: 1475–1486 (1992); Lochter, et al., *J. Cell. Biol.* 113: 1159–1171 (1991); Perez and Halfter, *Devel. Biol.* 156: 278–292 (1993); Taylor, et al., *J. Neurosci. Res.* 35: 347–362 (1993); Wehrle and Chiquet, *Development* 110: 401–415 (1990); and Wehrle-Haller and Chiquet, *J. Cell Sci.* 106: 597–610 (1993)). Other studies indicate that CT affects neuronal migration (Chuong, et al., *J. Cell. Biol.* 104: 331–342 (1987); Halfter, et al., *Dev. Biol.* 132: 14–25 (1989); Husmann, et al., *J. Cell Biol.* 116: 1475–1486 (1992)) and polarity (Lochter and Schachner, *J. Neurosci.* 13: 3986–4000 (1993)).

Depending on the assay systems and source of neurons, both inhibitory and stimulatory effects have been observed, Inhibition of neurite outgrowth was observed for both central neurons (Faissner and Kruse, Id. (1990); Grierson, et al., Id. (1990)) and peripheral neurons (Crossin, et al., Id. (1990); Taylor, et al., Id. (1993); Wehrle-Haller and Chiquet, Id. (1993)).

As noted previously, CT exists in vivo in various isoforms, depending upon the number of repeat sequences and the manner in which the molecule is spliced. For example, in the chicken, CT exists in at least three isoforms which are composed of polypeptides having molecular weights of 190, 200, and 220 kD (Grumet, et al., *PNAS USA* 82: 8075–8079 (1985)). Relative to the 190 kD isoform, the 200 kD form contains one, and the 220 kD form contains three, additional fn type III domains (Zisch, Id.(1992)).

The CT found in other species, including human and murine CT, for example, also exists in a variety of isoforms. By way of illustration, the alignment of the differentially spliced type III repeats of human, murine, and chick CT is illustrated in Weller, et al., *J. Cell Biol.* 112: 355–362 (1991) (see FIG. 3 therein). The type III repeats are contiguous in all three species. The three spliced repeats of chick CT and the five spliced repeats of murine CT show higher sequence similarity with certain of the seven repeats of human CT. The position of potential N-glycosylation sites also appears to have been conserved quite well between human and mouse. In chick CT, an additional splice variant has been described which lacks the first and second, but contains the third, of the differentially spliced type III repeats (Id.).

It has been suggested that outgrowth of peripheral neurites is inhibited only when confronting CT at a border in a two-dimensional substrate. Other reports have shown that CT can inhibit CNS neurite outgrowth in certain two- and three-dimensional assays. (See, e.g., Grierson, et al., Id. (1 990); Husmann, et al., Id. (1992); Lochter, et al., Id. (1 991); Perez, et al., Id. (1993); and Taylor, et al., Id. (1993)).

In contrast, when molecules that otherwise supported neural attachment and neurite outgrowth (e.g. polyamines or laminin) were mixed with CT in a uniform two-dimensional substrate, outgrowth was enhanced from peripheral and central nervous system neurons. (See, e.g., Taylor, et al., Id. (1993): Wehrle and Chiquet, Id. (1990); Wehrle-Haller and Chiquet, Id. (1993); Husmann, et al., Id. (1992); and Lochter, et al., Id. (1991).)

As noted previously, the present invention encompasses CT and derivatives thereof, which may be used in a wide variety of diagnostic, therapeutic, and other applications. As used herein, the phrase "CT derivatives" is intended to encompass CT (irrespective of the species of organism from which it is obtained), molecules substantially homologous to CT, polypeptides and proteins comprising one or more portions of an intact CT molecule, including sequential subsets thereof, as well as synthetic polypeptides, fusion proteins, and fusion polypeptides comprising one or more portions of a CT molecule or a molecule substantially homologous thereto. The phrase "CT derivatives" is also intended to include CT ligands, CT receptors, anti-CT antibodies and anti-idiotype antibodies, whether said antibodies are monoclonal or polyclonal.

C. Polypeptides

Polypeptides of the present invention may be derived from intact cytotactin (CT), or via synthetic means, such as those described hereinbelow. As described herein, intact CT may be purified from brain tissue (e.g. chick brain) and from fibroblast culture supernatant. (See, e.g., Crossin, *PNAS USA* 88: 11403–11407 (1991) and Hoffman, et al., *J. Cell Biol.* 106: 519–532 (1988), the disclosures of which are incorporated by reference herein.)

A polypeptide of the present invention is derived from a protein designated cytotactin (CT) or from molecules that are substantially homologous to CT. Alternatively, a polypeptide of the present invention may be translated from cDNA generated via polymerase chain reaction (PCR) or other synthetic means. (PCR procedures are described hereinbelow.) Preferably, a polypeptide of the present invention has an amino acid residue sequence that is substantially homologous to at least a portion of CT.

Polypeptides of the present invention preferably correspond in amino acid residue sequence to a sequence identified herein as either SEQ ID NO 2 or SEQ ID NO 4, to a sequence substantially homologous to SEQ ID NO 2 or SEQ ID NO 4, or to one or more sequential subsets thereof. A polypeptide of the present invention preferably corresponds in amino acid residue sequence to the sequence of human cytotactin, murine cytotactin, chicken cytotactin, or molecules that are substantially homologous thereto.

In another embodiment, a polypeptide of the present invention corresponds in amino acid residue sequence to a sequence identified herein as SEQ ID NO 2 or SEQ ID NO 4, to a sequence substantially homologous thereto, or to one or more sequential subsets thereof. Thus, in one embodiment, a polypeptide of the present invention has an amino acid residue sequence corresponding to the following: LDAPSGIEVKDVTDTTALITWFKPLAEIDGIELTY-GIKDVPGDRTTIDLTEDENQYSIGNLKPD TEYEVS-LISRRGDMSSNPAKETFTT (SEQ ID NO 5), or to a sequential subset or homolog thereof. In yet another embodiment, a polypeptide of the present invention has an amino acid residue sequence corresponding to the following: LDAPSHIEVKDVTDTTALITWFKPLAEIDSIELSY-GIKDVPGDRTTIDLTHEDNQYSIGNLRPD TEYEVS-LISRRVDMASNPAKETFIT (SEQ ID NO 6), or to a sequential subset or homolog thereof.

In another embodiment, a polypeptide of the present invention has an amino acid residue sequence corresponding to the following: LDAPSQIEAKDVTDTTALITWSKPLAEIEGIELTY-GPKDVPGDRTTIDLSEDENQYSIGNLRPH TEY-EVTLISRRGDMESDPAKEVFVT (SEQ ID NO 7), or to a sequential subset or homolog thereof.

In another variation, a polypeptide of the present invention has an amino acid residue sequence corresponding to the following: AMGSPKEVIFSDITENSATVSWRAPTAQVESFRITY-VPITGGTPSMVTVDGTKTQTRLVKLI PGVEYLVSI-IAMKGFEESEPVSGSFTT (SEQ ID NO 8), or to a sequential subset or homolog thereof. In yet another variation, a polypeptide of the present invention has an amino acid residue sequence corresponding to the following: AMGSPKEIMFSDITENAATVSWRAPTAQVESFRITY-VPMTGGAPSMVTVDGTDTETRLVK LTPGVEYRVS-VIAMKGFEESDPVSGTLIT (SEQ ID NO 9), or to a sequential subset or homolog thereof.

In a different embodiment, a polypeptide of the present invention has an amino acid residue sequence corresponding to the following: VVGSPKGISFSDITENSATVSWTPPRSRVDSYRVSYV-PITGGTPNVVTVDGSKTRTKLVKL VPGVDYNVNIIS-VKGFEESEPISGILKT (SEQ ID NO 10), or to a sequential subset or homolog thereof.

A polypeptide according to the present invention may have pronounced homologies with the amino acid residue sequence of human fibronectin, fibrinogen, or the amino acid residue sequence of epidermal growth factor (EGF). However, a polypeptide of the present invention is not identical to, and is distinguishable from, fibronectin, fibrinogen, and EGF. A polypeptide of the present invention may also be referred to herein as a CT-derived polypeptide or protein.

It is contemplated herein that CT-derived proteins and polypeptides substantially homologous to cytotactin (e.g. SEQ ID NO 2 or SEQ ID NO 4) are useful. In another embodiment, a polypeptide of this invention has an amino acid residue sequence comprising a sequential subset of cytotactin. Preferably, the polypeptide or protein also binds to an anti-CT antibody. Alternatively, a CT polypeptide or protein has an amino acid residue sequence at least 75% homologous to at least a portion of a sequence identified herein as SEQ ID NO 2 or 4. More preferably, they are at least 85% homologous; even more preferably, they are at least 90% homologous; most preferably, they are at least 95% homologous to at least a portion of one of the proteins identified herein as SEQ ID NO 2 or SEQ ID NO 4.

A polypeptide of the present invention can be used to generate a variety of useful antibodies by means described herein. Additionally, a polypeptide of the present invention may be used in competitive assays—e.g., to compete with CT for binding to an anti-CT antibody. Alternatively, a polypeptide of the present invention may be used to generate antibodies (or fragments thereof) to various portions of, or epitopes on, CT.

In addition, a polypeptide of the present invention may be used to promote or modulate cell attachment, spreading, growth, or neurite outgrowth, via binding to or occupying the relevant receptor to which a CT molecule would typically bind—that is, such a polypeptide would compete with CT for binding to the receptor. The various utilities of the polypeptides noted herein will further be apparent from the discussions provided hereinbelow.

Typically, a polypeptide of the present invention is not glycosylated, i.e., it is synthesized either directly by standard peptide synthesis techniques or by prokaryotic host expression of a recombinant DNA molecule of the present invention. A eukaryotically produced polypeptide is typically glycosylated. Useful polypeptides and proteins of the present invention may be glycosylated or not, depending on the use for which said construct is intended.

An instant polypeptide can incorporate a variety of changes, such as insertions, deletions, and substitutions of amino acid residues which are either conservative or nonconservative, as long as the resulting polypeptide molecule exhibits the desired properties. One such "desired property" is, for example, that the polypeptide is immunogenic in a suitable host and is able to generate antibodies to the CT molecule or a polypeptide homologous to at least a portion of CT, whether present in a denatured state (as found in an SDS-PAGE gel) or in the "natural" or "native" state (i.e., the state in which CT is usually expressed in vivo). An additional desired property is that the polypeptide is antigenic when expressed or in its denatured state, so that antibodies immunoreactive with the CT molecule also immunoreact with the instant polypeptide. Another desired property of a CT polypeptide of the present invention is its ability to stimulate cell attachment, cell spreading, cell elongation, to stimulate or inhibit neurite outgrowth, or some combination of the foregoing.

When a polypeptide of the present invention incorporates conservative substitutions in the sequences corresponding to CT as discussed herein, the substituted amino acid residues are preferably replaced by another, biologically similar amino acid residue such that the resulting polypeptide has an amino acid residue sequence that is similar to (i.e., is at least 50% homologous to) the CT protein or polypeptide sequences identified herein as SEQ ID NOS 2 or 4–10. Still another aspect of a polypeptide incorporating conservative substitutions occurs when a substituted amino acid residue replaces an unsubstituted parent amino acid residue. Examples of substituted amino acids may be found at 37 C.F.R. §1.822(b)(4), which species are incorporated herein by reference.

When a polypeptide of the present invention has an amino acid residue sequence that corresponds to the sequence of CT (see, e.g., SEQ ID NO 2 or SEQ ID NO 4) but has one or more conservative substitutions, preferably no more than about 40%, more preferably not more than about 30%, and even more preferably no more than about 20%, of the amino acid residues of the native protein are substituted. Polypeptides having no more than about 5–10% conservative substitutions are even more preferred.

Preferably, a protein or polypeptide of the present invention is at least about 3 amino acid residues in length, more preferably at least about 5 amino acids in length, and even more preferably, at least about 10 amino acids in length. In addition, a protein or polypeptide of the present invention is not more than about 250 amino acid residues in length, preferably not more than about 150 amino acids in length, even more preferably not more than about 100 amino acids in length, and more preferably still, not more than about 50 amino acids in length.

A polypeptide of the present invention can be synthesized by any of the peptide synthetic techniques known to those skilled in the art. A summary of some of the techniques available can be found in J. M. Stuard and J. D. Young, *Solid Phase Peptide Synthesis*, W. H. Freeman, Co., San Francisco (1969); J. Meinhofer, *Hormonal Proteins and Peptides* Vol. 2, pp. 46, Academic Press (New York) 1983; E. Schroder and K. Kubke, *The Peptides* (*Vol.* 1), Academic Press (New York), 1965 for classical solution synthesis, and U.S. Pat. No. 4,631,211, the disclosures of which are incorporated herein by reference. When a polypeptide desired for use according to the present invention is relatively short (i.e., less than about 50 amino acid residues in length) direct peptide synthetic techniques are generally favored, usually by employing a solid phase technique such as that of Merrifield (*JACS* 85: 2149 (1963)). Appropriate protective groups usable in the aforementioned syntheses are described in the above texts and in J. F. W. McOmie, *Protective Groups in Organic Chemistry*, Plenum Press, New York, 1973, which is incorporated herein by reference.

An instant polypeptide can also be synthesized by recombinant DNA techniques. Such recombinant techniques are favored especially when the desired polypeptide is relatively long (greater than about 50 amino acids residues in length). When recombinant DNA techniques are employed to prepare an instant polypeptide (see Example 1 hereinbelow), a DNA segment encoding the desired polypeptide is incorporated into a preselected vector that is subsequently expressed in a suitable host. The expressed polypeptide is then preferably purified by a routine method such as gel electrophoresis, immunosorbent chromatography, and the like.

Preferably, a CT polypeptide of this invention is further characterized by its ability to immunologically mimic an epitope (antigenic determinant) expressed by CT. As used herein, the phrase "immunologically mimic" in its various grammatical forms refers to the ability of a CT polypeptide of this invention to immunoreact with an antibody of the present invention that immunoreacts with a native epitope of CT as defined herein. It should be understood that a subject polypeptide need not be identical to the amino acid residue sequence of CT (or a portion thereof), so long as it includes the required sequence and is able to affect cell attachment, growth, elongation, neurite outgrowth, or is able to immunoreact with an anti-CT antibody, as described herein.

A subject polypeptide includes any analog, fragment or chemical derivative of a polypeptide whose amino acid residue sequence is shown herein so long as the polypeptide is capable of immunoreacting with an anti-CT antibody of the present invention or is capable of stimulating cell attachment, growth, elongation, or neurite outgrowth. Therefore, a polypeptide of the present invention can be subject to various changes, substitutions, insertions, and deletions, where such changes provide for certain advantages in its use. In this regard, a CT polypeptide of this invention corresponds to, rather than is identical to, one or more sequential subsets of the CT sequences identified herein as SEQ ID NOS 2 or 4. Alternatively, a CT polypeptide may comprise one or more of the amino acid residue sequences identified herein as SEQ ID NOS 5–10, sequential subsets thereof, or molecules substantially homologous thereto. Further, where one or more changes are made, a CT polypeptide preferably retains the ability to "perform" as described herein.

The term "analog" includes any polypeptide having an amino acid residue sequence substantially identical to a sequence specifically shown herein in which one or more residues have been conservatively substituted with a functionally similar residue and which displays the within-described abilities. The phrase "conservative substitution" also includes the use of a chemically derivatized residue in place of a non-derivatized residue provided that such polypeptide displays the requisite inhibition activity. "Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives, The imidazole nitrogen of histidine may be derivatized to form N-im-benzylhistidine.

Also included as chemical derivatives are those peptides which contain one or more naturally occurring amino acid derivatives of the twenty standard amino acids. Examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained. As noted herein, polypeptides having an amino acid residue sequence 75–100% homologous to a CT sequence identified herein as SEQ ID NO 2 or SEQ ID NO 4, or one or more sequential subsets thereof, are especially preferred.

When a polypeptide of the present invention has a sequence that is not identical to the sequence of CT, to any of the other CT-derived or CT-related sequences disclosed herein, or a sequential subset thereof, it is typically because one or more conservative or non-conservative substitutions have been made, usually no more than about 30 number percent, and preferably no more than 10 number percent of the amino acid residues are substituted. Additional residues may also be added at either terminus of a CT polypeptide for the purpose of providing a "linker" by which the polypeptides of this invention can be conveniently affixed to a label or solid matrix, or carrier. Preferably, the linker residues do not form CT epitopes, i.e., are not similar in structure to CT.

Amino acid residue linkers are usually at least one residue and can be 40 or more residues, more often 1 to 10 residues, but do not form CT epitopes. Typical amino acid residues used for linking are tyrosine, cysteine, lysine, glutamic and aspartic acid, or the like. In addition, a subject polypeptide can differ, unless otherwise specified, from the natural sequence of CT by the sequence being modified by terminal-$NH_2$ acylation, e.g., acetylation, or thioglycolic acid amidation, by terminal-carboxlyamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

When coupled to a carrier to form what is known in the art as a carrier-hapten conjugate, a CT polypeptide of the present invention is capable of inducing antibodies that immunoreact with CT. In view of the well established principle of immunologic cross-reactivity, the present invention therefore contemplates antigenically related variants of the polypeptides disclosed herein. An "antigenically related variant" is a subject polypeptide that is capable of inducing antibody molecules that immunoreact with homologous polypeptides and preferably with CT.

Any peptide of the present invention may also be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A CT polypeptide can be used, inter alia, in the diagnostic and cell culture methods and systems of the present invention. A CT polypeptide can also be used to prepare an inoculum as described herein for the preparation of antibodies that immunoreact with epitopes on CT. In addition, a CT polypeptide can be used in vitro to enhance cell culturing techniques and to promote cell attachment, growth, elongation, and/or spreading. A CT polypeptide of this invention can also be used in the therapeutic methods of the present invention as disclosed hereinbelow.

D. Nucleic Acid Molecules and Vectors

1. Nucleic Acid Molecules

DNA segments (i.e., synthetic oligonucleotides) that encode CT can easily be synthesized by chemical techniques, for example, the phosphotriester method of Matteucci, et al., (*J. Am. Chem. Soc.* 103: 3185–3191 (1981)) or via using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence. Furthermore, DNA segments consisting essentially of structural genes encoding CT can be obtained from recombinant DNA molecules containing a gene that defines CT, and can be subsequently modified, as by site directed mutagenesis, to introduce the desired substitutions.

A nucleic acid molecule according to the present invention may be produced by enzymatic techniques. Thus, restriction enzymes which cleave nucleic acid molecules at predefined recognition sequences can be used to isolate nucleic acid fragments from larger nucleic acid molecules containing the desired nucleic acid molecules such as the DNA (or RNA) that codes for the CT protein. Typically, DNA fragments produced in this manner will have cohesive, "overhanging" termini, in which single-stranded nucleic acid sequences extend beyond the double-stranded portion of the molecule. The presence of such cohesive termini is generally preferred over blunt-ended DNA molecules. The isolated fragments containing the desired coding sequence can then be ligated (cloned) into a suitable vector for amplification and expression.

Using PCR, it is possible to synthesize useful polypeptide-encoding polynucleotide sequences which may then be operatively linked to a vector and used to transform or transfect an appropriate cell and expressed therein. Particularly preferred methods for producing large quantities of recombinant CT polypeptides and proteins of the present invention rely on the use of preselected oligonucleotides as primers in a polymerase chain reaction (PCR) to form PCR reaction products as described herein.

If the DNA products described above are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among the preferred gene's plus (or coding) strands. To produce coding DNA homologs, first primers are therefore chosen to hybridize to (i.e. be complementary to) conserved regions within the gene(s) of choice.

Second primers become part of the coding (plus) strand and hybridize to a nucleotide sequence conserved among minus strands. To produce the coding DNA homologs, second primers are therefore chosen to hybridize with a conserved nucleotide sequence at the 5' end of the coding gene such as in that area coding for the leader or first framework region. It should be noted that in the amplification of the coding DNA homologs the conserved 5' nucleotide sequence of the second primer can be complementary to a sequence exogenously added using terminal deoxynucleotidyl transferase as described by Loh et al., *Science* 243: 217–220 (1989). One or both of the first and second primers can contain a nucleotide sequence defining an endonuclease recognition site (restriction site). The site can be heterologous to the gene being amplified and typically appears at or near the 5' end of the primer.

In PCR, each primer works in combination with a second primer to amplify a target nucleic acid sequence. The choice of PCR primer pairs for use in PCR is governed by various considerations, as discussed herein. That is, the primers have a nucleotide sequence that is complementary to a sequence conserved in the gene of choice. Useful priming sequences are disclosed hereinafter.

The strategy used for cloning the selected genes will depend, as is well known in the art, on the type, complexity, and purity of the nucleic acids making up the various genes. Other factors include whether or not the genes are to be amplified and/or mutagenized.

In using PCR technology herein, a DNA primer molecule encoding one or more of the aforementioned amino acid residue sequences is preferably utilized. However, additional nucleotide sequences can be utilized or revealed by cloning the cDNA or genomic DNA encoding CT and smaller amino acid residue sequences thereof. A DNA probe molecule encoding a CT amino acid residue sequence identical to or derived from (e.g., a sequential subset of) a CT amino acid residue sequence (such as that of SEQ ID NO 5) is preferred.

It should also be understood that the use of mixed, redundant primers that encode a targeted amino acid residue sequence utilizing different codons for the same amino acid residue is also contemplated. The PCR reaction is performed using any suitable method.

After producing various polypeptide-encoding DNA homologs for one or a plurality of different genes or DNA molecules, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, 4,683,195 and 4,965,188 (the disclosures of which are incorporated by reference herein), and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers for use as disclosed herein are also described in Nilsson, et al., *Cell* 58: 707 (1989), Ennis, et al., *PNAS USA* 87: 2833–7 (1990), and Zemmour, et al., *Immunogenetics* 33: 310–20 (1991), for example.

In particular, for amplifying nucleotide sequences for use in this invention, it is preferred to design primers from comparison of 5' and 3' untranslated regions of known allelic forms (if any), with selection of conserved sequences. Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

In preferred embodiments only one pair of first and second primers is used per amplification reaction. The amplification reaction products obtained from a plurality of different amplifications, each using a plurality of different primer pairs, are then combined. However, the present invention also contemplates DNA homolog production via co-amplification (using two pairs of primers), and multiplex amplification (using up to about 8, 9 or 10 primer pairs).

The present invention thus includes a variety of novel and useful nucleic acid molecules. In one embodiment, a nucleic acid molecule according to the present invention has a sequence identified herein as SEQ ID NO 1 or SEQ ID NO 3, or a nucleotide sequence substantially homologous thereto. In another variation, a nucleic acid molecule according to the present invention encodes a protein homologous to the protein identified herein as SEQ ID NO 2 or 4. In alternative embodiments, a nucleic acid sequence may comprise a molecule encoding a polypeptide comprising one or more sequential subsets of the protein identified herein as SEQ ID NO 2, or the protein identified as SEQ ID NO 4. In other embodiments, a nucleic acid molecule of the present invention encodes a polypeptide identified herein as having SEQ ID NO 5, 6, 7, 8, 9, or 10, or identified as CTfn3, CTfn6, or CTfn306, to name a few preferred embodiments.

Still other preferred nucleic acid molecules comprise nucleic acid molecules encoding an amino acid residue sequence identical to, or substantially homologous to, one of the CT proteins or polypeptides identified herein as SEQ ID NOS 5–10 or sequential subsets or derivatives thereof. In one embodiment, a nucleic acid molecule encodes a polypeptide or protein up to about 250 amino acid residues in length. In another embodiment, the nucleic acid molecule encodes a polypeptide or protein of up to about 150 amino acids in length. In yet another embodiment, the nucleic acid molecule encodes a polypeptide or protein up to about 100 amino acids in length. In another variation, the nucleic acid molecule encodes a polypeptide up to about 50 amino acids in length. In various preferred embodiments, a nucleic acid molecule of the present invention encodes a polypeptide at least 3 amino acids in length, more preferably at least 5 amino acids in length, and even more preferably at least 10 amino acids in length.

Another set of DNA molecules of the present invention encode a polypeptide identified herein as CTegf, CTfn1–2, CTfn3, CTfn4, CTfn5, CTspl, CTfn6, CTfn3–6, CTfg, or combinations thereof. In other preferred embodiments, a nucleic acid molecule according to the present invention encodes a chimeric protein or polypeptide, a fusion protein or polypeptide, or a conjugate, wherein the amino acid sequence encoded by said nucleic acid molecule includes the sequence identified herein as SEQ ID NO 2 or SEQ ID NO 4, or one or more sequential subsets thereof. In still other embodiments, the amino acid sequence encoded by said nucleic acid molecule is substantially homologous to SEQ ID NOS 2 or 4, or one or more sequential subsets thereof.

An especially preferred nucleic acid molecule of the present invention comprises a polynucleotide molecule encoding a protein at least 75% homologous to the protein represented by SEQ ID NO 2, or the protein represented by SEQ ID NO 4. Alternatively, a polynucleotide molecule of the present invention encodes a polypeptide that is 75–100% homologous to a portion of the proteins identified herein as SEQ ID NO 2 or 4. Two preferred nucleotide sequences are identified herein as SEQ ID NOS 1 and 3.

As noted hereinabove, proteins and polypeptides of the present invention may be synthesized (or otherwise modified) using recombinant techniques. Albeit DNA constructs are described herein as exemplary, it is expressly to be understood that RNA molecules are also contemplated for use as disclosed herein. For example, a protein or polypeptide of the present invention may be prepared and expressed as described in Example 1 hereinbelow.

When recombinant techniques are employed to prepare a polypeptide of the present invention, a nucleic acid (e.g., DNA) molecule or segment encoding the polypeptide is preferably used. A preferred DNA molecule contemplated by the present invention is operatively linked to a vector that is subsequently expressed in a suitable host. The molecule is "operatively linked" to the vector as used herein when it is ligated (covalently bound) thereto, according to common usage. The present invention also encompasses RNA molecules equivalent to the instantly-disclosed DNA molecules.

Nucleic acid molecules according to the present invention may readily be synthesized via chemical techniques, e.g., by the well-known phosphotriester method. (See, e.g., Matteuci et al., *JACS* 103: 3185 (1981).) By chemically synthesizing nucleic acid molecules, any desired substitution, insertion or deletion of an amino acid residue or sequence from a template polypeptide, e.g., the native protein, can be readily provided by simply making the corresponding changes in the nucleotide sequence of the DNA molecule.

Whenever an RNA molecule encoding a polypeptide of the present invention is used, the RNA molecule including the polypeptide coding molecule is transcribed into complementary DNA (cDNA) via a reverse transcriptase. The cDNA molecule can then be transcribed and translated as described herein to generate a desired polypeptide.

In a preferred aspect of the invention, a DNA nucleotide sequence (molecule) encoding at least one of the amino acid residue sequences of CT identified herein (e.g., SEQ ID NO 2) is operatively linked to a larger DNA molecule. The resultant DNA molecule is then transformed or transfected into a suitable host and expressed therein.

A nucleic acid molecule encoding an amino acid residue sequence according to the present invention can be provided with start and stop codons, or one or both of the start and stop codons can be provided by a larger nucleic acid molecule (e.g., a vector) operatively linked to the nucleic acid molecule so that only the corresponding polypeptide is generated. Alternatively, a nucleic acid sequence encoding additional amino acid residues can be provided at the 3' and/or 5' ends of the nucleic acid molecule so that a larger polypeptide is expressed having an amino acid residue sequence at either or both of its N-terminal and C-terminal ends in addition to an amino acid residue sequence of (or derived from) the CT molecule.

2. Vectors

Expression of recombinant CT polypeptides and proteins of this invention is accomplished through the use of expression vectors into which the PCR amplified CT sequences described above have been inserted. The expression vectors may be constructed utilizing any of the well-known vector construction techniques. Those techniques, however, are modified to the extent that the translatable nucleotide sequence to be inserted into the genome of the host cell is flanked "upstream" of the sequence by an appropriate promoter and/or enhancer sequence.

The choice of vector to which a nucleotide segment of the present invention is operatively linked depends directly, as is well known in the art, on the functional properties desired, e.g., protein expression, and the host cell to be transformed or transfected, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

Thus, the present invention contemplates a vector that can be operatively linked to a nucleic acid molecule of the present invention to provide a self-replicating recombinant DNA molecule that encodes an instantly-disclosed CT protein or polypeptide, preferably expressing one or more of the CT protein or polypeptide sequences identified herein. The recombinant molecule can be used to transform or transfect suitable host cells so that the host cells express the desired polypeptide. Hence, a preferred nucleic acid molecule may be regarded as self-replicating.

The choice of vector to which a nucleic acid molecule of the present invention is operatively linked depends, as is well known in the art, on the functional properties desired, e.g., efficiency of expression, the transformation or transfection host cell, and the like. However, a vector of the present invention is at least capable of directing the replication, and preferably also expression, of a nucleic acid molecule encoding an instant polypeptide or protein.

In many preferred embodiments, the vector also contains a selectable marker. After expression, the product of the translatable nucleotide sequence may then be purified using antibodies against that sequence. One example of a selectable marker is antibiotic resistance. A plasmid encoding ampicillin or tetracycline resistance (or both) may be included in each transfection such that a population of cells that express the gene(s) of choice may be ascertained by growing the transfectants in selection medium. Examples of such vectors including such markers are pUC18, pUC19, pKK233-2, and pKK388-1 (Clontech, Palo Alto, Calif.).

In various embodiments, the translatable nucleotide sequence may be incorporated into a plasmid with an appropriate controllable transcriptional promoter, translational control sequences, and a polylinker to simplify insertion of the translatable nucleotide sequence in the correct orientation, and may be expressed in the host cells. Useful host cells include eukaryotic insect cells, such as *Spodoptera frugiperda*, or prokaryotic cells, such as *Escherichia coli*. As described in the Examples herein, prokaryotic cells are particularly preferred. Preferably, there are 5' control sequences defining a promoter for initiating transcription and a ribosome binding site operatively linked at the 5' terminus of the upstream translatable DNA sequence. Examples of useful expression vectors including promoters such as tac, trc, or $P_L$, for example, include pTrc99A (Pharmacia, Piscataway, N.J.), pKK223-3 (Clontech), and pDR540tac.

Prokaryotic gene fusion vectors, which have the ability to express cloned genes as fusion proteins, are also useful according to the present invention. For example, protein A vectors pRIT2T or pEZZ18 (Pharmacia) use protein A as the fusion partner and IgG Sepharose 6FF for affinity purification. Phagemid EZZ18 (Pharmacia) allows for the secretion of fusion proteins from *E. coli* into the surrounding culture medium.

Another useful protein fusion and purification system is one available from New England Biolabs (Beverly, Mass.), which uses pMAL vectors. In this system, the cloned gene is inserted into a pMAL vector downstream from the malE gene, which encodes maltose-binding protein (MBP). This results in the expression of an MBP-fusion protein. (See, e.g., Guan, et al., *Gene* 67: 21–30 (1987).) The technique uses the strong $P_{tac}$ promoter and the translation initiation signals of MBP to express large amounts of the fusion protein. The fusion protein is then purified by a one-step affinity purification for MBP (Kellerman and Ferenci, *Meth. Enzymol*. 90: 459–463 (1982)). (Also see Riggs, et al. (eds.), *Current Protocols in Molecular Biology*, Greene Assoc./

Wiley Interscience, NY (1990) and the manufacturer's instructions accompanying the pMAL kit.)

A particularly useful system for cloning and expression is the GST gene fusion system (Pharmacia, Piscataway, N.J.), use of which is described in the Examples herein (e.g., Example 1). In general, however, prokaryotic expression vectors useful therein include pTrc99A, pKK223-3, and pDR540tac. Useful prokaryotic gene fusion vectors include pGEX-1λT, pGEX-2T, pGEX-3X, pGEX-4T-1, pGEX-4T-2, pGEX-4T-3, pGEX-5X-1, pGEX-5X-2, pGEX-5X-3, and pGEX-2TK; and useful protein A vectors include pRIT2T or pEZZ18 (Pharmacia, Piscataway, N.J.). Kits for cloning and expression are also commercially available and include the GST Gene Fusion System available from Pharmacia (Piscataway, N.J.).

To achieve high levels of gene expression in transformed or transfected cells—for example, *E. coil*—it is necessary to use not only strong promoters to generate large quantities of mRNA, but also ribosome binding sites to ensure that the mRNA is efficiently translated. In *E. coli*, for example, the ribosome binding site includes an initiation codon (AUG) and a sequence 3–9 nucleotides long located 3–11 nucleotides upstream from the initiation codon (Shine et al., *Nature* 254: 34 (1975)). The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors, including (1) the degree of complementarity between the SD sequence and 3' end of the 16S tRNA; and (2) the spacing and possibly the DNA sequence lying between the SD sequence and the AUG. (See, e.g., Roberts et al., *PNAS USA* 76: 760 (1979a); Roberts et al., *PNAS USA* 76: 5596 (1979b); Guarente et al., *Science* 209: 1428 (1980); and Guarente et al., *Cell* 20: 543 (1980).)

Optimization is generally achieved by measuring the level of expression of genes in plasmids in which this spacing is systematically altered. Comparison of different mRNAs shows that there are statistically preferred sequences from positions –20 to +13 (where the A of the AUG is position 0; see, e.g., Gold et al., *Ann. Rev. Microbiol.* 35: 365 (1981). Leader sequences have also been shown to influence translation dramatically (Roberts et al., 1979 a, b supra). Binding of the ribosome may also be affected by the nucleotide sequence following the AUG, which affects ribosome binding. (See, e.g., Taniguchi et al., *J. Mol. Biol.* 118: 533 (1978).)

Vectors for use in producing large quantities of the recombinant polypeptides and proteins of this invention may be designed for the expression of proteins in bacteria, in mammalian cells or in insect cells. For expression in bacterial *E. coli*, the expression vectors are preferably utilized in conjunction with bacterial "host" cells adapted for the production of useful quantities of proteins or polypeptides. Such vectors may include a prokaryotic replicon i.e., a nucleotide sequence having the ability to direct autonomous replication and maintenance of the recombinant DNA molecule extra-chromosomally in a prokaryotic host cell, such as a bacterial host cell, transformed therewith. Such replicons are well known in the art. In addition, those embodiments that include a prokaryotic replicon may also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable nucleotide sequences.

The prokaryotic expression vectors also contain promoters which can be used in the microbial organism for expression of its own proteins. Those promoters most commonly used include the beta-lactamase and lactose promoter systems and the tryptophan promoter system as described in the European Patent Application No. 0125023, the relevant disclosures of which are incorporated by reference herein.

Promoter sequences compatible with bacterial hosts, such as a tac promoter, are typically provided in plasmid vectors having convenient restriction sites for insertion of a DNA molecule of the present invention. Promoter sequences compatible with bacterial hosts are typically provided in plasmid vectors containing convenient restriction sites for insertion of a DNA segment of the present invention. Exemplary prokaryotic expression vectors include the plasmids pUC8, pUC9, pUC18, pBR322, and pBR329 available from Bio-Rad Laboratories (Richmond, Calif.), pPL and pKK223 available from Pharmacia (Piscataway, N.J.), and pBS, M13mp19, pNH8a, pNH16A, pNH18a, and pNH46a (Stratagene, La Jolla, Calif.). Other exemplary vectors include pCMU (Nilsson, et al., *Cell* 58: 707 (1989)). Other appropriate vectors may also be synthesized, according to known methods; for example, vectors pCMU/K$^b$ and pCMUII are modifications of pCMUIV (Nilsson, et al., supra).

Exemplary cloning and expression vector systems for use according to the within-described methods include those described in Example 1 herein. For example, the pGEX system is particularly useful according to the within-disclosed methods.

Successfully transformed or transfected cells, i.e., cells that contain a rDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.* 98: 503 (1975) or Berent et al., *Biotech.* 3: 208 (1985).

In addition to directly assaying for the presence of rDNA, successful transformation or transfection can be confirmed by well known immunological methods for the presence of expressed protein. For example, cells successfully transformed or transfected with an expression vector produce proteins which then can be assayed directly by immunological methods or for the presence of the function of the expressed protein.

It will be understood that this invention, although described herein in terms of various preferred embodiments, should not be construed as limited to the host cells, expression vectors and expression vectors systems exemplified. Other expression vector systems, well known to one of ordinary skill in the art and described by Kaufman, et al., in *Current Protocols in Molecular Biology*, Ausubel et al., eds., Unit 16, New York (1990), are contemplated for preparing recombinant CT polypeptides and proteins for use in this invention.

Expression vectors compatible with eukaryotic cells, preferably those compatible with vertebrate cells, can also be used to form a recombinant DNA molecule as described above. Eukaryotic cell expression vectors are well known in the art and are available from several commercial sources. Typically, such vectors are provided with convenient restriction sites for insertion of the desired DNA molecule. Typical of such vectors are pSVL and pKSV-10 (Pharmacia), pBPV-1pML2d (International Biotechnologies, Inc.), pXT1 and pSG5 (Stratagene, La Jolla, Calif.) and pTDT1 (ATCC, #31255). Other useful vectors include the pREP series vectors and pEBVhis, which are available from Invitrogen (San Diego, Calif.); vectors pTDT1 (ATCC #31255), pCP1 (ATCC #37351) and pJ4W (ATCC #37720), available from the American Type Culture Collection (ATCC); and other, similar expression vectors. A preferred drug resistance marker for use in vectors compatible with is eukaryotic cells is the neomycin phosphotransferase (neo) gene. (Southern et al., *J. Mol. Appl. Genet.* 1: 327–341 (1982)).

Retroviral expression vectors capable of generating the recombinant DNA of the present invention are also contemplated. The construction and use of retroviral vectors for generating desired DNA molecules have been described by Sorge, et al., *Mol. Cell. Biol.* 4: 1730–37 (1984).

A number of methods are available to operatively link DNA to vectors via complementary cohesive termini. For instance, complementary homopolymer tracts can be added to the DNA molecule to be inserted and to the vector DNA. The vector and DNA molecule are then allowed to hybridize by hydrogen bonding between the complementary homopolymer tails to form recombinant duplex DNA molecules.

Alternatively, synthetic linkers containing one or more restriction sites can be used to join the DNA molecule to vectors. When the DNA molecule is generated by endonuclease restriction digestion, as described earlier, it is treated with bacteriophage T4 DNA polymerase of *E. coli* DNA polymerase I which removes protruding 3' single-stranded termini and fills in recessed 3' ends. Blunt-ended DNA molecules are thereby generated.

Blunt-ended DNA molecules are incubated with a large molar excess of linker molecules in the presence of an enzyme that is able to catalyze the ligation of blunt-ended DNA molecules, such as bacteriophage T4 DNA ligase. Thus, the products of the reaction are DNA molecules bonded at their ends to linker sequences having restriction sites therein. The restriction sites of these DNA molecules are then cleaved with the appropriate restriction enzyme and the molecules ligated to an expression vector having termini compatible with those of the cleaved DNA molecule. Synthetic linkers containing a variety of restriction endonuclease sites are commercially available from a number of sources including International Biotechnologies, Inc. (New Haven, Conn.).

3. Transformation/Transfection of Hosts

The present invention also relates to host cells transformed or transfected with a recombinant DNA molecule of the present invention. The host cell can be either prokaryotic or eukaryotic. Preferred prokaryotic host cells are strains of *E. coli*, e.g., the *E. coli* strain NM522 available from Stratagene (La Jolla, Calif.). Preferred eukaryotic host cells include yeast and mammalian cells, preferably vertebrate cells such as those from mouse, rat, monkey or human fibroblastic cell line. Preferred eukaryotic host cells also include Chinese hamster ovary (CHO) cells, such as those available from the ATCC as CCL61, and NIH Swiss mouse embryo cells NIH/3T3 available from the ATCC as CRL 1658.

Transformation or transfection of appropriate cell hosts with a recombinant DNA molecule of the present invention is accomplished by well known methods that typically depend on the type of vector used. With regard to transformation of prokaryotic host cells, see, for example, Maniatis et al., *Molecular Cloning. A Laboratory Manual*, Cold Spring Harbor Laboratory, Cold Spring Harbor, N.Y. (1982). With regard to transfection of vertebrate cells with retroviral vectors containing RNA encoding the instant polypeptides and a reverse transcriptase, see, e.g., Sorge et al., *Mol. Cell. Biol.* 4: 1730–37 (1984).

Successfully transformed or transfected cells, i.e., those containing a recombinant DNA molecule of the present invention, can be identified by well known techniques. For example, transformed or transfected cells can be cloned to produce monoclonal colonies. Cells from those colonies can be harvested, lysed and their DNA content examined for the presence of the desired DNA molecule using a method such as that described by Southern, *J. Mol. Biol.* 98: 503 (1975).

In addition to directly assaying for the presence of the desired DNA molecule, successful transformation or transfection can be confirmed by well known immunological methods when the DNA directs expression of the polypeptides of the present invention. Samples of cells suspected of being transformed or transfected are harvested and assayed for antigenicity by antibodies that specifically bind to the instant polypeptides.

In addition to the transformed or transtected host cells themselves, also contemplated by the present invention are cultures of those cells. Nutrient media useful for culturing transformed or transfected host cells are well known in the art and can be obtained from several commercial sources. In embodiments wherein the host cell is mammalian a "serum-free" medium is preferably used.

Methods for recovering an expressed protein from a culture are well known in the art. For instance, gel filtration, gel chromatography, ultrafiltration, electrophoresis, ion exchange, affinity chromatography and related techniques can be used to isolate the expressed proteins found in the culture. In addition, immunochemical methods, such as immunoaffinity, immunoadsorption, and the like, can be performed using well known methods, as exemplified by the methods described herein.

E. Hybridomas

1. Hybridomas

Hybridomas of the present invention are those which are characterized as having the capacity to produce an antibody, including a monoclonal antibody, of the present invention. Particularly preferred antibodies as disclosed herein include anti-CT antibodies, anti-CT polypeptide antibodies, and anti-(CT idiotype) antibodies, to name a few examples.

Methods for producing hybridomas producing (secreting) antibody molecules having a desired immunospecificity, i.e., having the ability to immunoreact with a particular protein, an identifiable epitope on a particular protein and/or a polypeptide, are generally well known in the art. For example, useful methods are described by Niman et al., *PNAS USA* 80: 4949–4953 (1983), and by Galfre et al., *Meth. Enzymol.* 73: 3–46 (1981). Other methods are described in U.S. Pat. Nos. 5,180,806, 5,114,842, 5,204,445, and RE 32,011, the disclosures of which are incorporated by reference herein.

A hybridoma cell is typically formed by fusing an antibody-producing cell and a myeloma or other self-perpetuating cell line. Such a procedure was described by Kohler and Milstein, *Nature* 256: 495–497 (1975). It is preferred that the myeloma cell line be from the same species as the lymphocytes. A mouse of the strain 129 GIX$^+$ is one preferred mammal. Suitable mouse myelomas for use in the present invention include the hypoxanthine-aminopterin-thymidine-sensitive (HAT) cell lines P3X63-Ag8.653, and Sp2/O-Ag14 that are available from the American Type Culture Collection, Rockville, Md., under the designations CRL 1580 and CRL 1581, respectively.

Typically, hybridomas of the present invention are produced by using, in the above techniques as an immunogen, a substantially pure CT protein, CT homolog, a CT polypeptide, a CT ligand, a CT receptor, or any other CT derivative of the present invention. Methods of generating antibodies via preparation of hybridomas are further described in Subsection 3 below.

2. Inocula

In another embodiment, a protein or polypeptide of this invention, an antigenically related variant thereof, or a protein or polypeptide at least 75% homologous to at least a portion of the CT protein identified herein as SEQ ID NO 2 or SEQ ID NO 4, or a CT polypeptide identified herein as SEQ ID NOS 5–10, is used in a pharmaceutically acceptable aqueous diluent composition to form an inoculum that, when administered in an effective amount, is capable of inducing antibodies that immunoreact with a CT protein or polypeptide. The word "inoculum" in its various grammatical forms is used herein to describe a composition containing a CT protein or polypeptide of this invention as an active ingredient used for the preparation of antibodies against a CT protein or polypeptide.

When a polypeptide is used to induce antibodies it is to be understood that the polypeptide can be used alone, or linked to a carrier as a conjugate, or as a polypeptide polymer, but for ease of expression, the various embodiments of the polypeptides of this invention are collectively referred to herein by the term "polypeptide", and its various grammatical forms. For a polypeptide that contains fewer than about 35 amino acid residues, it is preferable to use the peptide bound to a carrier for the purpose of inducing the production of antibodies as already noted.

As previously noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis*., 147. 318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol*. Vol. 8, Suppl. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, and cholera toxoid, as well as polyamino acids such as poly (D-lysine: D-glutamic acid), and the like. The choice of carrier is more dependent upon the ultimate use of the inoculum and is based upon various criteria. For example, a carrier that does not generate an untoward reaction in the particular animal to be inoculated should be selected.

The present inoculum contains an effective, immunogenic amount of a CT protein or polypeptide of this invention; as noted above, a smaller polypeptide may be used as a conjugate (i.e., linked to a carrier). The effective amount of polypeptide or protein per unit dose depends, among other things, on the species of animal inoculated, the body weight of the animal, and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "dose" or "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared by dispersing a polypeptide, polypeptide-conjugate, or protein in a physiologically tolerable (acceptable) diluent or vehicle such as water, saline or phosphate-buffered saline to form an aqueous composition. For example, inocula containing CT protein are typically prepared from substantially pure CT protein by dispersion in the same physiologically tolerable diluents. Such diluents are well known in the art and are discussed, for example, in *Reminaton's Pharmaceutical Sciences*. 16th Ed., Mack Publishing Company, Easton, Pa. (1980) at pages 1465–1467.

Inocula may also include an adjuvant as a component of the diluent. Adjuvants such as complete Freund's adjuvant (CFA), incomplete Freund's adjuvant (IFA) and alum are materials well known in the art, and are available commercially from several sources.

F. Antibodies and Antibody Compositions

The present invention also discloses antibodies (including anti-idiotype antibodies) and antibody compositions, which immunoreact with an instant protein, polypeptide, or antibody. An antibody composition of the present invention preferably comprises antibody molecules capable of immunoreacting with CT proteins or polypeptides of the present invention, or with CT receptors. Thus, an antibody composition binds to one or more epitopes presented by the CT protein or polypeptide in cellular or cell-free environments.

One preferred antibody composition of the invention immunoreacts with a CT protein or polypeptide. Particularly preferred antibody compositions in this regard are monoclonal, although polyclonal antibodies are also useful as disclosed herein. Other preferred compositions include antibodies that immunoreact with anti-CT protein or polypeptide antibodies; i.e., they are anti-idiotype antibodies. Briefly, a preferred antibody composition is generated by immunizing animals (e.g., mice) with avian or mammalian CT or a CT-derived polypeptide of this invention. The antibodies generated are screened for binding affinity for a CT protein or polypeptide of the instant invention. Isolated CT or CT polypeptides may be used for screening the antibodies.

Many of the instantly-disclosed Abs immunoreact with CT proteins, polypeptides, or both. As a result, the present invention also contemplates methods for inhibiting the binding of CT proteins or polypeptides to CT receptors. Anti-CT polypeptide Abs may also be used to inhibit CT or CT polypeptide function; for example, anti-CTfn3 and anti-CTfn6 Abs interfere with the stimulatory effects of Ctfn3 and CTfn6.

A preferred antibody composition as contemplated herein is typically produced by immunizing an animal (typically, a mammal) with an inoculum containing avian or mammalian CT, a CT polypeptide, or a CT derivative of the present invention, thereby inducing in the mammal antibody molecules having the appropriate immunospecificity for the immunogenic agent. The antibody molecules are then collected from the mammal, screened and purified to the extent desired using well known techniques such as, for example, immunoaffinity purification using the immunogen immobilized on a solid support. The antibody composition so produced can be used, inter alia, in the diagnostic and therapeutic methods and systems of the present invention.

A monoclonal antibody composition (mAb) is also contemplated by the present invention, as noted before. The instantly-disclosed mAb compositions thus typically display a single binding affinity for any antigen with which they immunoreact. However, a given monoclonal antibody composition may contain antibody molecules having two different antibody combining sites, each immunospecific for a different antigenic determinant, i.e., a bispecific monoclonal antibody.

An instant mAb is typically composed of antibodies produced by clones of a single cell that produces one kind of antibody molecule. Preferred hybridomas and methods of preparing same are described in Section E and Examples 2–4 herein. In general, however, the present invention contemplates a method of forming a monoclonal antibody molecule that immunoreacts with a CT protein, polypeptide, derivative or antibody of the present invention. One method comprises the steps of:

(a) Immunizing an animal with an immunogenic agent of this invention. Use of at least a portion of CT as the immunogen is preferred. The immunogen may be a protein taken directly from a subject animal species. However, the antigen can also be linked to a carrier protein such as keyhole limpet hemocyanin, particularly when the antigen is small, such as a polypeptide consisting essentially of a sequential subset of the a.a. residue sequence identified herein as SEQ ID NO 2 or 4. The immunization is typically performed by administering the sample to an immunologically competent mammal in an immunologically effective amount, i.e., an amount sufficient to produce an immune response. Preferably, the mammal is a lagomorph such as a rabbit, or a rodent, such as a rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein-Barr virus (EBV), simian virus 40 (SV40), polyoma virus and the like, RNA viruses such as Moloney murine leukemia virus (Mo-MuLV), Rous sarcoma virus and the like, myeloma cells such as P3X63-Ag8.653, Sp2/O-Ag14 and the like.

In preferred embodiments, treatment with the transforming agent results in the production of an "immortalized" hybridoma by fusing the suspended spleen cells with mouse myeloma cells from a suitable cell line, e.g., SP-2, by the use of a suitable fusion promoter. The preferred ratio is about 5 spleen cells per myeloma cell in a suspension containing about 108 splenocytes. A preferred fusion promoter is polyethylene glycol having an average molecule weight from about 1000 to about 4000 (commercially available as PEG 1000, etc.); however, other fusion promoters known in the art may be employed. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that does not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 0.3–0.5) in each separate container (e.g., each well of a microtiter plate). The medium is one (e.g., HAT medium) that does not sustain the drug-resistant (e.g., 8-azaguanine resistant) unfused myeloma cell line.

(e) The tissue culture medium of the cloned transformants is analyzed (immunologically assayed) to detect the presence of antibody molecules that preferentially react with the instant CT-related proteins or polypeptides or—in the case of anti-idiotype antibodies—with antibodies to CT proteins or polypeptides. This may be accomplished using well known immunological techniques.

(f) A desired transformant is then selected and grown in an appropriate tissue culture medium for a suitable length of time, followed by recovery (harvesting) of the desired antibody from the culture supernatant by well known techniques. A suitable medium and length of culturing time are also well known or are readily determined.

A monoclonal anti-CT protein or polypeptide antibody contains, within detectable limits, only one species of antibody combining site capable of effectively immunologically binding a CT protein or polypeptide and displays a single binding affinity for a CT protein or polypeptide. It should also be understood that the present invention contemplates "humanized" antibodies, which may be prepared via a variety of well-known methods.

To produce a much greater concentration of slightly less pure monoclonal antibody, the desired hybridoma can be transferred by injection into mice, preferably syngenic or semisyngenic mice. The hybridoma causes formation of antibody-producing tumors after a suitable incubation time, which results in a high concentration of the desired antibody (about 5–20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8: 396 (1959)) supplemented with 4.5 gm/l glucose, 20 mM glutamine, and 20% fetal calf serum. A preferred inbred mouse strain is Balb/c.

Methods for producing the instant hybridomas which generate (secrete) the antibody molecules of the present invention are well known in the art and are described further herein. Particularly applicable descriptions of relevant hybridoma technology are presented by Niman et al., *PNAS USA* 80: 4949–4953 (1983), and by Galfre et al., *Meth. Enzymol.* 73: 3–46 (1981). Monoclonal anti-CT protein or polypeptide antibody compositions may also be produced using methods well known in the art. See, for example, *Antibodies: A Laboratory Manual*, Harlow and Lane, eds., Cold Spring Harbor, N.Y. The disclosures of the foregoing articles are incorporated herein by reference.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in prokaryotic and eukaryotic hosts are disclosed in the following, the disclosures of which are incorporated by reference herein: Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.* 4: 1730–1737 (1984); Beher et al., *Science* 240: 1041–1043 (1988); Skerra et al., *Science* 240: 1030–1041 (1988); and Orlandi et al., *PNAS U.S.A.* 86: 3833–3837 (1989). Typically the nucleic acid codes for all or part of an immunoglobulin variable region that binds a preselected antigen (ligand). Sources of such nucleic acids are well known to one skilled in the art and, for example, can be obtained from a hybridoma producing a monoclonal antibody that binds the preselected antigen, or the preselected antigen can be used to screen an expression library coding for a plurality of immunoglobulin variable regions, thus isolating the nucleic acid.

A further preferred method for forming the instant antibody compositions involves the generation of libraries of Fab molecules using the method of Huse et al., *Science* 246: 1275 (1989). In this method, mRNA molecules for heavy and light antibody chains are isolated from the immunized animal. The mRNAs are amplified using polymerase chain reaction (PCR) techniques. The nucleic acids are then randomly cloned into lambda phage to generate a library of recombined phage particles. The phage are used to infect an expression host such as *E. coli*. The *E. coli* colonies and corresponding phage recombinants can then be screened for those producing the desired Fab fragments. Preferred lambda phage vectors include λgt11, λzap II, and pComb3.

An antibody molecule-containing composition according to the present invention can take the form of a solution or suspension. The preparation of a composition that contains antibody molecules as active ingredients is well understood in the art. Typically, such compositions are prepared as liquid solutions or suspensions, however, solid forms suitable for solution in, or suspension in, liquid can also be prepared. The preparation can also be emulsified. The active therapeutic ingredient is often mixed with excipients which do not interfere with the assay and are compatible with the active ingredient. Suitable excipients are, for example, water, saline, dextrose, glycerol, ethanol, and the like, and combinations thereof. In addition, if desired, the composition may contain minor amounts of auxiliary substances such as wetting or emulsifying agents, pH buffering agents and the like, which enhance the effectiveness of the active ingredient.

An antibody molecule composition may further be formulated into a neutralized acceptable salt form. Acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Antibodies and antibody compositions of the present invention include monoclonal and polyclonal antibodies, and further include anti-peptide antibodies, anti-CT-derivative antibodies, anti-peptide antibodies, anti-CT protein or polypeptide antibodies, anti-CT receptor binding site-specific antibodies, and anti-(CT idiotype) antibodies. Methods of preparing the foregoing types of antibodies are generally disclosed hereinabove and in Examples 2–4 below. In general, depending on the type of immunogen used, it is anticipated that antibodies with the desired specificity may be produced and isolated.

For example, the present invention contemplates an antibody comprising antibody molecules (or fragments thereof) that immunoreact with CT at a preselected or predetermined receptor binding site. Stated differently, the antibody is specific for one or more of the receptor binding sites on CT as defined herein, and is referred to as an anti-CT receptor binding site specific antibody.

An anti-CT receptor binding site specific antibody is capable of immunologically binding with a CT protein or polypeptide but does not specifically bind molecules lacking the epitope recognized by the antibody. For example, a CTfn6 receptor binding site-specific antibody binds the CTfn6 binding site present on CT or on a CT polypeptide including the CTfn6 segment and thus inhibits the binding of the CT protein or polypeptide to its cognate receptor at said site. It is expressly to be appreciated that the specified CT binding site—e.g., a CTfn3 or CTfn6 binding site—is that portion of CT that is bound by its cognate receptor. Fragments derived from or homologous to CT may also contain a CT binding site (e.g., a CTfn3 binding site, a CTfn6 binding site, or both).

In preferred embodiments an, an anti-CT receptor binding site specific antibody of this invention comprises antibody molecules that immunoreact with (a) CT, and (b) a CT polypeptide of this invention. Preferably, an anti-CT receptor binding site specific antibody of the present invention does not immunoreact with CTfn3 or CTfn6, or with one or more of the polypeptides identified herein as SEQ ID NOS 5–10. In another embodiment, an anti-CT receptor binding site specific antibody of the present invention immunoreacts with CTfn3 or with CTfn6, but not both.

In various preferred embodiments, a composition containing an anti-CT receptor binding site specific antibody of the present invention is substantially free of antibody molecules that immunoreact with epitopes other than a CT binding site. Antibody reactivity with a CT polypeptide can be measured by a variety of immunological assays known in the art. Exemplary immunoreaction assays are described herein.

An anti-CT receptor binding site specific antibody of the present invention is typically produced by immunizing an animal with an inoculum containing a CT polypeptide of this invention and thereby induce in the animal antibody molecules having immunospecificity for the immunizing polypeptide. The antibody molecules are then collected from the animal and isolated to the extent desired by well known techniques such as, for example, by using DEAE Sephadex to obtain the IgG fraction. Exemplary antibody preparation methods using CT polypeptides in the immunogen are described herein.

The preparation of antibodies against proteins or polypeptides is well known in the art. (See, e.g., Staudt et al., *J. Exp. Med.* 157: 687–704 (1 983)). In order to generate anti-CT receptor binding site-specific antibodies, then, a laboratory animal is inoculated with an immunologically effective amount of a CT protein or polypeptide, typically as present in a vaccine of the present invention. The anti-CT polypeptide antibody molecules induced thereby are then collected from the animal and are isolated to the extent desired by well known techniques including, without limitation, immunoaffinity chromatography.

To enhance their specificity, the antibodies are preferably purified by immunoaffinity chromatography using solid phase-affixed immunizing protein or polypeptide. The antibody is contacted with the solid phase-affixed immunizing agent for a period of time sufficient for the agent to immunoreact with the antibody molecules to form a solid phase-affixed immunocomplex. The bound antibodies are separated from the complex by standard techniques.

The word "inoculum" in its various grammatical forms is used herein to describe a composition containing a CT protein or polypeptide of this invention as an active ingredient used for the preparation of antibodies of this invention. When a protein or polypeptide is used in an inoculum to induce antibodies, it is to be understood that the protein or polypeptide can be used in various embodiments, e.g., alone, or linked to a carrier as a conjugate or as a polypeptide polymer.

For ease of expression, the various embodiments of the proteins and polypeptides of this invention may henceforth be collectively referred to herein by the term "polypeptide" and its various grammatical forms.

In embodiments of the present invention wherein a CT-derived polypeptide contains fewer than about 35 amino acid residues, it is preferable to use the peptide bound to a carrier for the purpose of inducing the production of antibodies. One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.* 8 (*Suppl.* 7): 7–23 (1978) and U.S. Pat. No. 4,493,795, U.S. Pat. No. 3,791,932 and U.S. Pat. No. 3,839,153, the disclosures of which are incorporated herein by reference. In addition, a site directed coupling reaction can be carried out so that any loss of activity due to polypeptide orientation after coupling can be minimized. See, for example, Rodwell et al., *Biotech.* 3: 889–894 (1985), and U.S. Pat. No. 4,671,958, incorporated by reference herein.

Exemplary additional linking procedures include the use of Michael addition reaction products, di-aldehydes such as glutaraldehyde (see, e.g., Klipstein, et al., *J. Infect. Dis.* 147: 318–326 (1983)) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) propionatel) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid, polyamino acids such as poly (D-lysine: D-glutamic acid), and the like.

The choice of carrier is generally dependent upon the ultimate use of the inoculum, as is understood in the art. For example, a carrier that does not generate an untoward reaction in the particular animal to be inoculated should be selected.

The present inoculum contains an effective, immunogenic amount of a CT protein, polypeptide, or derivative of this invention, typically as a conjugate linked to a carrier. The effective amount of protein or polypeptide per unit dose sufficient to induce an immune response to the immunizing agent depends, among other things, on the species of animal inoculated, the body weight of the animal, and the chosen inoculation regimen, as is well known in the art. Inocula typically contain protein or polypeptide concentrations of about 10 micrograms ($\mu$g) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition. Inocula can also include an adjuvant as part of the diluent. Adjuvants such as complete Freund's adjuvant (CFA), incomplete Freund's adjuvant (IFA) and alum are materials well known in the art, and are available commercially from several sources.

The anti-CT antibodies so produced can be used, inter alia, in the diagnostic methods and systems of the present invention to detect CT proteins or polypeptides present in a sample such as a body fluid sample. In addition, anti-CT antibodies can be used in therapeutic methods, e.g., for inhibiting receptor binding to CT proteins or polypeptides, based on the ability of the antibody to specifically bind the CT receptor binding site and block CT protein or polypeptide binding. In various embodiments, polyclonal or monoclonal anti-CT antibodies are preferred and can be produced as previously described using the CT proteins or polypeptides of this invention in the inoculum.

5. Anti-Idiotype Antibodies

Anti-idiotype antibodies are antibodies that have the internal image of a particular entity and therefore express antigenic determinants or epitopes that are immunochemically similar or identical to the epitopes found on an external antigen. For example, an anti-(CT idiotype) antibody is an anti-idiotype antibody that contains the internal image of the portion of CT that binds to the cellular receptor that recognizes a specific binding site on CT. Since different receptors recognize distinct sites on the intact CT protein molecule, the present invention contemplates a variety of anti-(CT idiotype) antibodies.

Thus, in one embodiment, the present invention contemplates methods and compositions employing an anti-idiotype antibody. In preferred variations, the anti-idiotype antibody is an anti-(CT idiotype) antibody.

One species of anti-(CT idiotype) antibody is able to mimic the function of a CT protein or polypeptide of the present invention. For example, one preferred anti-idiotype antibody is able to mimic the function of CTfn3, i.e., it is capable of stimulating cell attachment, growth, elongation, or neurite outgrowth, or a combination of the foregoing. Another exemplary anti-idiotype antibody is able to mimic the function of CTfn6, i.e., it is also able to stimulate cell attachment, growth, elongation, or neurite outgrowth, or a combination of same. Anti-(CT idiotype) antibodies may also be engineered to inhibit these activities in the appropriate contexts.

Another species of anti-(CT idiotype) antibody of the present invention preferably contains a paratope whose structure is defined by the ability to: (1) bind to the CTfn3 binding site to form a CTfn3 binding site/anti-(CT idiotype) antibody complex, and (2) immunoreact with an anti-CT protein or polypeptide antibody as defined herein.

Yet another species of anti-(CT idiotype) antibody of the present invention preferably contains a paratope whose structure is defined by the ability to: (1) bind to the CTfn6 binding site to form a CTfn6 binding site/anti-(CT idiotype) antibody complex, and (2) immunoreact with an anti-CT protein or polypeptide antibody as defined herein.

An anti-(CT idiotype) antibody binds to a CT binding site and forms a CT binding site/anti-(CT idiotype) antibody complex if it competes with a CT protein or polypeptide for binding to the selected CT binding site in a competition assay that, for example, employs a labelled CT protein or polypeptide.

An anti-(CT idiotype) antibody immunoreacts with an anti-CT protein or peptide antibody. Various immunoassays for detecting the formed immunoreaction product or complex are well known and include radio-immunoassays and enzyme-linked immunoassays. See, for example, *Antibodies: A Laboratory Manual*. Harlow and Lane, eds., Cold Spring Harbor, N.Y. (1988).

An anti-(CT idiotype) antibody of the present invention can be distinguished from other antibodies that may block CT binding to its cognate receptors because anti-(CT idiotype) antibodies immunoreact with anti-CT antibodies while such other antibodies do not.

An anti-(CT idiotype) antibody is prepared using methods and procedures well known in the art. See, e.g., Benjamini et al., "Immunogens and Improved Methods of Making Immunogens", Published International Application No. WO 88/00472, published Jan. 28, 1988; Standt et al., *J. Exp. Med.* 157:.687–704 (1983); Reagan et al., *J. Virol.* 48: 660–666 (1983), and Ardman et al., *J. Exp. Med.* 161: 669–686 (1985), the disclosures of which are incorporated by reference herein. Briefly, to produce an anti-(CT idiotype) antibody composition of this invention, an anti-CT protein or polypeptide antibody is first produced by inoculating a laboratory animal with an immunologically effective amount of a CT protein or polypeptide, typically present in a vaccine to produce an anti-CT protein or polypeptide antibody.

For example, a vaccine useful for preparing anti-idiotype antibodies of the present invention comprises immunologically effective amounts of both a CT protein or polypeptide and an immunopotentiator suitable for use in animals, preferably mammals. An immunopotentiator is a molecular entity that stimulates maturation, differentiation and function of B and/or T lymphocytes. Immunopotentiators are well known in the art and include T cell stimulating polypeptides such as those described in U.S. Pat. No. 4,426,324 and the C8-substituted guanine nucleosides described by Goodman et al., *J. Immunol.* 135: 3284–88 (1985) and U.S. Pat. No. 4,643,992, the disclosures of which are incorporated by reference herein.

A vaccine can also include an adjuvant as part of the excipient. Adjuvants such as complete Freund's adjuvant (CFA) and incomplete Freund's adjuvant (IFA) for use in laboratory animals are well known in the art. Pharmaceutically acceptable adjuvants such as alum can also be used. An exemplary vaccine thus comprises one ml of phosphate buffered saline (PBS) containing about 1 mg to about 5 mg CT protein or polypeptide adsorbed onto about 0.5 mg to about 2.5 mg of alum. A preferred vaccine comprises 1 ml of PBS containing 1 mg CT protein or polypeptide adsorbed onto 2.5 mg of alum. The phrases "suitable for use in animals" and "pharmaceutically acceptable" refer to molecular entities and compositions that do not produce an allergic or similar untoward reaction when administered to an animal.

The anti-CT protein or polypeptide antibodies produced by the above vaccination method or via the methods described in Section E herein are collected from the animal and those immunospecific for the CT protein or polypeptide are isolated to the extent desired by well known techniques such as, for example, immunoaffinity chromatography.

The monoclonal or polyclonal anti-CT protein or polypeptide antibody produced according to within-disclosed methods is used to prepare an anti-(CT idiotype) antibody by inoculating a laboratory animal (preferably an animal) with an effective amount of the anti-CT protein or polypeptide antibody produced above to produce anti-(CT idiotype) antibodies. The anti-(CT idiotype) antibodies capable of binding an anti-CT protein or polypeptide antibody are isolated, to the extent desired by well known techniques such as, for example, immunoaffinity chromatography.

Anti-(CT idiotype) antibodies capable of binding an anti-CT protein or polypeptide antibody are then assayed for their ability to bind to the appropriate, preselected CT binding site indicating that these anti-idiotype antibodies have the internal image of a CT protein or polypeptide. Anti-(CT idiotype) antibodies that bind their respective CT binding sites are selected and are useful in practicing this invention. For example, one species of anti-(CT idiotype) antibody is assayed for its ability to bind to the CTfn3 binding site by a competition assay with a labelled CT protein or a CTfn3-derived polypeptide. An anti-(CT idiotype) antibody that competes in this competition assay is then selected.

Suitable anti-(CT idiotype) antibodies in monoclonal form, typically whole antibodies, can also be prepared using hybridoma technology such as that described in Section E herein. Another useful technique is described in Reagan et al., *PNAS* 84: 3891–95 (1987).

Splenocytes are typically fused with myeloma cells using polyethylene glycol (PEG) 1500. Fused hybrids are selected by their sensitivity to HAT. Hybridomas secreting the anti-idiotype antibody molecules of this invention are identified using serological methods such as a commercially available enzyme linked immunosorbent assay (ELISA) diagnostic assay for detecting antibodies to an anti-CT protein or polypeptide antibody. Once the hybridoma is shown to be secreting an anti-idiotype antibody that binds an anti-CT protein or polypeptide antibody, these antibodies are further screened for their ability to compete with a CT protein or polypeptide for binding to the appropriate, preselected CT binding site.

A monoclonal anti-idiotype antibody composition of the present invention can be produced by initiating a monoclonal hybridoma culture comprising a nutrient medium containing a hybridoma that secretes antibody molecules of the appropriate anti-(CT idiotype) specificity. The culture is maintained under conditions and for a time period sufficient for the hybridoma to secrete the antibody molecules into the medium. The antibody-containing medium is then collected. The anti-(CT idiotype) antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8: 396 (1959)) supplemented with 4.5 gm/1 glucose, 20 mm glutamine, and 20% fetal calf serum. An exemplary inbred mouse strain is the Balb/c.

G. Assay Methods

1. Cell Attachment Assays

The present invention also contemplates various assay methods, including methods of determining the presence of, and degree of, cell attachment to a particular compound, composition, or substrate. Related kits and components thereof are also disclosed. In various embodiments, the composition, composition or substrate is one according to the present invention and includes various proteins, polypeptides and antibodies described herein.

For example, in one embodiment, substrates for the cell attachment assays are prepared by binding said substrate (e.g., a protein or polypeptide) to a solid support—for example, a polystyrene dish. The amount of bound substrate is quantitated in order to determine the relationship between the number of cells attached to the substrate with the molar amount of substrate present.

To assist in interpretation of assay results, a substrate compound or composition is preferably labeled. For example, a protein of the present invention may be radiolabeled, e.g., with $^{125}I$. A variety of other useful labels (e.g., biotin) are known in the art.

Solid supports (also described as solid surfaces or solid substrates) useful according to the present invention include supports made of glass, plastic, nitrocellulose, cross-linked dextrans (e.g., SEPHADEX; Pharmacia, Piscataway, N.J.), agarose in its derivatized and/or cross-linked form, polyvinyl chloride, polystyrene, cross-linked polyacryiamide, nitrocellulose- or nylon-based webs such as sheets, strips or paddles, tubes, plates, the wells of a microtiter plate such as those made from polystyrene or polyvinylchloride, and the like, and may take the form of a planar surface or microspheres (e.g., Enzymobeads, Bio-Rad Laboratories, Richmond, Calif.), to name a few variations.

Proteins or polypeptides according to the present invention are then admixed with trace amounts of labeled protein or polypeptide and are spotted on solid supports (e.g., polystyrene dishes) and adsorbed thereto, and nonspecific binding sites blocked according to methods known in the art. The substrate-coated support is then cut into small sections and the amount of radioactivity associated with each spot is determined.

To ensure that differences in cell attachment to compounds or compositions of the present invention is not due to differences in amounts adsorbed to the support, the amount of protein or peptide bound per spot is preferably determined for each protein or polypeptide, and cell attachment is then assessed per mole of protein or polypeptide.

Subsequently, a predetermined amount of preselected cells is added to the substrate formed when a protein, polypeptide, or other composition of the present invention is adsorbed onto a solid support, and is allowed to incubate for a predetermined period of time under appropriate assay conditions. After incubation, the cell culture is preferably washed and the number of bound cells determined according to well-known methods. For example, visual observation—e.g., using a 10× objective with an eyepiece reticle—is an appropriate means of determining the number of cells bound. Preferably, repeat measurements are obtained and the number of bound cells is expressed as the average of the number of measurements±standard deviation (SEM).

Cell attachment inhibition assays may also be useful according to the present invention. An exemplary method is disclosed in Example 5.C. herein.

The present invention further contemplates assay methods and kits for the detection of neurite outgrowth, including methods for detecting the stimulation and inhibition of neurite outgrowth. Various proteins, polypeptides, and antibodies disclosed herein are useful according to the within-disclosed methods and may be included in the kits that are also described herein.

The substrates used in the neurite outgrowth assays are essentially the same as those used in the cell attachment assays, as described hereinabove. Any cells adhering to the substrates were examined for sprouting and neurite length as defined herein. Substrates used in the neurite outgrowth assays may be prepared as described above.

Appropriate cells are prepared for use in the neurite outgrowth assay. For example, the preparation of dorsal root ganglia cells is described in Example 5.A.4. Before beginning the assay, the cells may be resuspended, added to substrate-coated dishes, and placed under predetermined assay conditions for a preselected period of time. After the attachment and growth period, the dishes may be rinsed to remove unbound cells, fixed, and viewed—e.g., by phase contrast microscopy.

Preferably, a plurality of cells are analyzed for each substrate spot. Cells are then "judged" based on predetermined criteria. For example, cells may be considered neurite-bearing if the length of the processes are greater than one cell diameter. The percent of cells that are sprouting neurites is preferably determined, as is the average neurite length. A particularly preferred neurite outgrowth assay method is disclosed in Example 6 hereinbelow.

H. Therapeutic Compositions and Methods

The various proteins and polypeptides disclosed herein are useful in a variety of applications, including therapeutic ones. Therapeutic compositions of the present invention may alternatively contain a physiologically tolerable carrier together with at least one species of anti-CT antibody (or an anti-(CT idiotype) antibody) of this invention as described herein, dispersed therein as an active ingredient. In a preferred embodiment, the therapeutic composition is not immunogenic when administered to a human patient for therapeutic purposes.

For the sake of simplicity, the active agent of the therapeutic compositions described herein shall be referred to as a "CT derivative". It should be appreciated that this term is intended to encompass CT proteins, polypeptides, anti-CT antibodies, and anti-(CT idiotype) antibodies, as well as derivatives thereof.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

A therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a CT derivative of the present invention, typically an amount of at least 0.1 weight percent of CT derivative per weight of total therapeutic composition. A weight percent is a ratio by weight of CT derivative to total composition. Thus, for example, 0.1 weight percent is 0.1 grams of CT derivative per 100 grams of total composition.

A therapeutically effective amount of a CT derivative-containing composition, or beneficial compound therein, is a predetermined amount calculated to achieve the desired effect, i.e., to effectively benefit the individual to whom the composition is administered, depending upon the benefit to be conferred. Thus, an effective amount can be measured by improvements in one or more symptoms associated with tumors (e.g., glioma) occurring in a patient.

Effective amounts may also be measured by improvements in neuronal or ganglion cell survival, axonal regrowth, and connectivity following axotomy (see, e.g., Bray, et al., "Neuronal and Nonneuronal Influences on Retinal Ganglion Cell Survival, Axonal Regrowth, and Connectivity After Axotomy", *Ann. N.Y. Acad. Sci.*: 214–228 (1991)). Improvements in neuronal regeneration in the CNS and PNS are also indicators of the effectiveness of treatment with the disclosed compounds and compositions, as are improvements in nerve fiber regeneration following traumatic lesions. (See, e.g., Cadelli, et al., *Exp. Neurol.* 115: 189–192 (1992), and Schwab, *Phil. Trans. R. Soc. Lond.* 331: 303–306 (1991).)

Thus, the dosage ranges for the administration of the anti-CT antibody of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted by the individual physician in the event of any complication.

The compositions are administered in a manner compatible with the dosage formulation, and in a therapeutically effective amount. A therapeutic amount of an anti-CT antibody composition of this invention is an amount sufficient to produce the desired result, and can vary widely depending upon the disease condition and the potency of the therapeutic compound. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

It is further contemplated that counter-receptor ligands for CT, whether it is in soluble or cell-surface associated form, may be useful according to the within-disclosed diagnostic and therapeutic methods. For example, antibodies or polypeptides which prevent the binding of CT to its cognate receptor are useful diagnostic and therapeutic compounds. Useful antibodies which prevent the binding of CT may include antibodies such as anti-CTfn3, anti-CTfn6, and the like, molecules that are substantially homologous to said antibodies, and molecules which mimic the activity of anti-CT antibodies.

Useful polypeptides which inhibit the binding of CT to its receptor(s) include CTfn3, CTfn6, and CTfn3–6. Proteins and polypeptides useful as disclosed herein also include CT derivatives that are substantially homologous to CT, whether it is derived from human, avian, or other mammalian sources.

In addition, it is contemplated that CT derivatives will be useful in diagnostic and therapeutic methods according to the present invention. CT derivatives useful in this context include the within-disclosed proteins, polypeptides and homologs thereof, as well as antibodies, such as anti-CT antibodies and anti-(CT idiotype) antibodies.

A variety of useful compositions, including bioabsorbable materials (e.g., collagen gels) may be used in conjunction with the CT derivatives of the present invention in a variety of therapeutic applications. For example, CT derivatives may be used to coat the interior of tubes used to connect severed neurons; they may be added directly to suture materials or incorporated in bioabsorbable materials in and on sutures; further, they may be utilized on/in implants and prosthetic devices, either alone or in conjunction with other bioabsorbable and supporting materials.

The terms "therapeutically effective" or "effective", as used herein, may be used interchangeably and refer to an amount of a therapeutic composition of the present invention—e.g., one containing an anti-CT monoclonal antibody. For example, a therapeutically effective amount of an anti-CT antibody-containing composition, or beneficial compound therein, is a predetermined amount calculated to achieve the desired effect, i.e., to effectively benefit the individual to whom the composition is administered, depending upon the benefit to be conferred.

The antibodies and compounds of the present invention are typically administered as a pharmaceutical composition in the form of a solution or suspension. However, therapeutic compositions of the present invention may also be formulated for therapeutic administration as a tablet, pill, capsule, aerosol, sustained release formulation or powder.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration.

Alternatively, continuous intravenous infusion sufficient to maintain therapeutically effective concentrations in the blood are contemplated. Therapeutically effective blood concentrations of antibody molecules of the present invention (including anti-CT idiotype) antibodies) are in the range of about 0.01 $\mu$M to about 100 $\mu$M, preferably about 0.1 $\mu$M to about 10 $\mu$M, and more preferably about 0.1 $\mu$M to about 1.0 $\mu$M.

It is further contemplated that the various CT derivatives (including proteins, polypeptides, and antibodies) as described herein can be used therapeutically in a variety of applications. For example, as described above, a variety of useful compositions, including bioabsorbable materials may be used in conjunction with the CT derivatives of the present invention to coat the interior of tubes used to connect severed neurons; they may be added directly to suture materials or incorporated in bioabsorbable materials in and on sutures; further, they may be utilized on/in implants and prosthetic devices, either alone or in conjunction with other bioabsorbable and supporting materials. As always, the administration of therapeutically effective amounts of physiologically tolerable compositions containing a CT derivative of this invention to a patient in need of treatment is preferred.

As described previously, a therapeutically effective amount of a CT derivative of the present invention is a predetermined amount calculated to achieve the desired effect, i.e., to promote neurite outgrowth. In the case of in vivo therapies, an effective amount can be measured by improvements in neuronal regeneration, to name one example.

Thus, the dosage ranges for the administration of a CT derivative of the invention are those large enough to produce the desired effect in which the symptoms of disease—e.g., neuronal degeneration—are ameliorated or decreased. The dosage should not be so large as to cause adverse side effects, although none are presently known. Generally, the dosage will vary with the age, condition, and sex of the patient, as well as with the extent and severity of the disease in the patient, and can be determined by one of skill in the art. The dosage can be adjusted by the individual physician in the event of any complication.

A therapeutically effective amount of a CT derivative of this invention is typically an amount such that when it is administered in a physiologically tolerable composition, it is sufficient to achieve a plasma or local concentration of from about 1 picomolar (pM) to 1,000 nanomolar (nM), preferably about 100 pM to about 50 nM, and most preferably about 1 to 30 nM. The CT derivatives of the invention can be administered parenterally by injection or by gradual infusion over time. For example, anti-CT antibodies of the invention can be administered intravenously, intraperitoneally, intramuscularly, parenterally, subcutaneously, intracavity, transdermally, or dermally, and they may also be delivered by peristaltic means. In general, intravenous, intraperitoneal, or subcutaneous administration is preferred.

The therapeutic compositions containing a CT derivative of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

I. Diagnostic Systems and Methods

The present invention also contemplates methods for detecting conditions identifiable via expression of levels of CT in excess of a predetermined control value. For example, anti-CT antibodies of the present invention are useful in detecting the presence of tumors (e.g., glioma), as well as detection of metastasis or angiogenesis.

Diagnostic assays of the present invention may also be used to detect cell surface receptors that bind CT, as well as anti-CT antibodies. The assay may be made specific for CT or any of the within-described CT derivatives by a proper selection of antibody specificity. Also, an assay of the invention may be used to identify polypeptide receptors homologous to portions of CT as well as "free" receptors—i.e., polypeptides or proteins unassociated with any particular cell structure, polypeptides homologous to CT, or polypeptide portions thereof. Typically, the assay methods involve detecting intact CT, although assays for detecting CT polypeptides or anti-CT antibodies are also contemplated.

A method for detecting an antigenic protein or polypeptide of the present invention preferably comprises formation of an immunoreaction product between the protein or polypeptide and an anti-polypeptide antibody molecule, as disclosed herein. The antigen to be detected may be present in a body fluid or tissue sample. The immunoreaction product is detected by methods well-known to those skilled in the art. Numerous clinical diagnostic chemistry procedures may be utilized to form the detectible immunocomplexes.

Alternatively, a protein or polypeptide ligand (non-antibody composition) for an instant CT receptor or polypeptide may be used in the assay method. An exemplary ligand in this aspect of the invention is a labelled CT polypeptide (e.g., SEQ ID NO 5). Thus, while exemplary assay methods are described herein, the invention is not so limited.

A preferred assay method of the present invention involves determining the presence of CT in a sample, and thereby ascertaining the level of CT expression in an individual or sample. Various heterogeneous and homogeneous assay protocols may be employed, either competitive or non-competitive, for detecting the presence and preferably amount of CT in a body sample, preferably fluid sample.

One useful method comprises admixing a body sample, preferably one obtained from a human donor or patient, containing cells and/or fluid to be analyzed with one of the within-described antibody compositions that are capable of immunoreacting with CT proteins or polypeptides. The cell sample may also be washed prior to the admixing step. The immunoreaction admixture thus formed is maintained under appropriate assay conditions—e.g., biological assay conditions—for a time period sufficient for any cells expressing the antigen, or for any soluble antigen, to immunoreact with antibodies in the antibody composition to form an antibody-receptor immunocomplex. The immunoreaction product (immunocomplex) is then separated from any unreacted antibodies present in the admixture. The presence, and if desired, the amount of immunoreaction product formed is then determined. The amount of product formed may then be correlated with the amount of receptors expressed by the cells, or with the amount of soluble antigen expressed.

Determination of the presence or amount of immunoreaction product formed depends upon the method selected for identifying the product. For instance, a labelled antibody may be used to form a labelled immunocomplex with a receptor molecule of the present invention (e.g., CT). The labelled immunocomplex may be quantitated by methods appropriate for detecting the respective label—e.g., fluorescent labels, radioactive labels, biotin labels and the like—as discussed herein. Alternatively, an unlabelled antibody may be used to form an unlabelled immunocomplex, which is subsequently detected by immunoreacting a labelled antibody recognizing the unlabelled antibody with the unlabelled immunocomplex. The immunocomplex thereby becomes labelled and may be detected as described above.

Biological conditions used in the instant assays are those that maintain the biological activity of the antibody, the CT molecule, CT proteins, CT polypeptides, and other CT derivative molecules of this invention. Those conditions include a temperature range of about 4° C. to about 45° C., preferably about 37° C., at a pH value range of about 5 to about 9, preferably about 7, and an ionic strength varying from that of distilled water to that of about one molar sodium chloride, preferably about that of physiological saline. Methods for optimizing such conditions are well known in the art.

In a preferred embodiment, a body sample to be analyzed is withdrawn from a donor or patient and apportioned into aliquots. At least one aliquot is used for the determination of antigen expression using an antibody composition of the present invention. If desired, a second aliquot may be used for determining reactivity of a control antibody with the sample. The analyses may be performed concurrently but are usually performed sequentially.

In a further aspect of the invention, data obtained in the instant assays are recorded via a tangible medium, e.g., computer storage or hard copy versions. The data can be automatically input and stored by standard analog/digital (A/D) instrumentation that is commercially available. Also, the data can be recalled and reported or displayed as desired for best presenting the instant correlations of data. Accordingly, instrumentation and software suitable for use with the present methods are contemplated as within the scope of the present invention.

The antibody compositions and methods of the invention also afford a method of monitoring treatment of patients afflicted with tumors or with neurodegenerative and other diseases in which expression of CT receptors is correlated with the disease state. Accordingly, a method of monitoring a patient's response to treatment is contemplated in which a marker for the disease is detectable and/or detected. The method comprises admixing a body sample containing cells to be assayed for CT marker with an antibody composition of the present invention, according to an assay method as described above. The admixture is maintained for a time period sufficient to form an immunoreaction product under predefined reaction conditions. The amount of immunoreaction product formed is correlated to an initial disease state. These steps are repeated at a later time during the treatment regimen, thereby permitting determination of the patient's response to treatment.

Diagnostic systems for performing the described assays are also within the scope of the present invention. A diagnostic system of the present invention is preferably in kit form and includes, in an amount sufficient for at least one assay, a composition containing antibody molecules of the present invention (or fragments thereof) as a separately packaged reagent. The antibody molecules may be labelled, or a labeling reagent may be separately packaged and included within the kit, wherein the label is capable of indicating whether or not an immunoreaction product is present. Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

In one embodiment, a diagnostic system is contemplated for assaying for the presence of CT receptors expressed on cells in a cell-containing sample. In another embodiment, a diagnostic system is contemplated for use in assaying for the presence of CT proteins and/or polypeptides, or CT antibodies.

A preferred kit is typically provided as an enclosure (package) comprising a container for anti-CT antibodies capable of immunoreacting with CT-related receptor molecules on cells in a cell sample. Typically, the kit also contains a labelled antibody probe that immunoreacts with the immunocomplex formed when an anti-CT antibody and a CT receptor, protein, or polypeptide immunoreact.

In another variation, a preferred kit is provided as an enclosure (package) that comprises a container including anti-CT antibodies capable of immunoreacting with CT receptor molecules, whether or not the receptor molecules are attached to, or free of, cellular material in the test sample. Typically, the kit also contains a labelled antibody probe that immunoreacts with the immunocomplex of the anti-CT antibody and the CT receptor.

The label may be any of those commonly available, including, without limitation, fluorescein, phycoerythrin, rhodamine, $^{125}$I, and the like. Other exemplary labels include $^{111}$In, $^{99}$Tc, $^{67}$Ga, and $^{131}$I and nonradioactive labels such as biotin and enzyme-linked antibodies. Any label or indicating means that may be linked to or incorporated in an antibody molecule is contemplated as part of an antibody or monoclonal antibody composition of the present invention. A contemplated label may also be used separately, and those atoms or molecules may be used alone or in conjunction with additional reagents. Many useful labels of this nature are known in clinical diagnostic chemistry.

The linking of labels to polypeptides and proteins is also well known. For instance, antibody molecules produced by a hybridoma may be labelled by metabolic incorporation of radioisotope-containing amino acids provided as a component in the culture medium. See, for example, Galfre et al., *Meth. Enzymol.* 73: 3–46 (1981)., The techniques of protein conjugation or coupling through activated functional groups are particularly applicable. See, for example, Aurameas, et al., *Scand. J. Immunol.*, Vol. 8, Suppl. 7: 7–23 (1978), Rodwell et al., *Biotech*. 3: 889–894 (1984), and U.S. Pat. No. 4,493,795 (the latter of which is incorporated by reference herein).

An instant diagnostic system may also include a specific binding agent. A "specific binding agent" is a chemical species capable of selectively binding a reagent species of the present invention but is not itself an antibody molecule of the present invention. Exemplary specific binding agents are antibody molecules, complement proteins or fragments thereof, protein A and the like that react with an antibody molecule of this invention when the antibody is present as part of the immunocomplex described above.

In preferred embodiments the specific binding agent is labelled. However, when the diagnostic system includes a specific binding agent that is not labelled, the agent is typically used as an amplifying means or reagent. In these embodiments, a labelled specific binding agent is capable of specifically binding the amplifying means when the amplifying means is bound to a complex containing one of the instant reagents.

For example, a diagnostic kit of the present invention may be used in an "ELISA" format to detect the presence or quantity of a CT protein or polypeptide in a body sample or body fluid sample such as serum, plasma or urine or a detergent lysate of cells, e.g., a 10 mM CHAPS lysate. “ELISA” refers to an enzyme-linked immunosorbent assay that employs an antibody or antigen bound to a solid phase and an enzyme-antigen or enzyme-antibody conjugate to detect and quantify the amount of antibody or antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which patent disclosures are incorporated herein by reference.

In preferred embodiments, the antibody or antigen reagent component may be affixed to a solid matrix to form a solid support that is separately packaged in the subject diagnostic systems. The reagent is typically affixed to the solid matrix by adsorption from an aqueous medium, although other modes of affixation well known to those skilled in the art may be used, such as specific binding methods. For example, an instant anti-CT antibody may be affixed to a surface and used to assay a solution containing CT molecules or cells expressing CT receptors. Alternatively, CT, CT homologs, polypeptide fragments of CT or CT homologs, and whole or partially lysed cells expressing CT may be affixed to the surface and used to screen a solution for antibody compositions that immunoreact with the affixed species.

Useful solid matrix materials in this regard include the derivatized cross-linked dextran available under the trademark SEPHADEX from Pharmacia Fine Chemicals (Piscataway, N.J.), agarose in its derivatized and/or cross-linked form, polystyrene beads about 1 micron to about 5 millimeters in diameter (available from Abbott Laboratories of North Chicago, Ill.), polyvinyl chloride, polystyrene, cross-linked polyacrylamide, nitrocellulose- or nylon-based webs such as sheets, strips or paddles, tubes, plates, the wells of a microtiter plate such as those made from polystyrene or polyvinylchloride, and the like.

The reagent species, labelled specific binding agent or amplifying reagent of any diagnostic system described herein may be provided in solution, as a liquid dispersion or as a substantially dry powder, e.g., in lyophilized form. Where the indicating means is an enzyme, the enzyme's substrate may also be provided in a separate package of a kit or system. Usually, the reagents are packaged under an inert atmosphere. A solid support such as the before-described microtiter plate and one or more buffers may also be included as separately packaged elements in this diagnostic assay system.

The diagnostic system is usually contained in a conventional package. Such packages include glass and plastic (e.g., polyethylene, polypropylene and polycarbonate) bottles, vials, plastic and plastic-foil laminated envelopes and the like.

J. Cell Culture Methods and Kits

Proteins and polypeptides of the present invention are also useful in a variety of applications relating to cell and tissue cultures. For example, in one embodiment, a method of promoting the attachment of cells to a solid surface (or substrate) comprises the steps of (1) immobilizing on the substrate a CT protein or polypeptide exhibiting cell attachment activity; and (2) providing free cells for attachment to said substrate. The CT protein or polypeptide may be selected from the group consisting of SEQ ID NOS 2 and 4–10; in another embodiment, a CT protein or polypeptide is selected from the group consisting of CT, CTfn3, CTfn6, CTfn3–6, and CTfg.

In another embodiment, the invention discloses a method of preparing substrates for the attachment of cells thereto, comprising obtaining a CT protein or polypeptide exhibiting cell attachment activity and treating solid substrates having a surface to which cell attachment is desired with said polypeptide. In various disclosed embodiments, the solid support or substrate may comprise glass, agarose, a synthetic resin material (e.g., nitrocellulose, polyester, polyethylene, and the like), long-chain polysaccharides, and other similar substances.

The invention also discloses compositions comprising CT proteins or polypeptides exhibiting a cell-attachment activity in substantially pure form. In various embodiments, the polypeptides are derived from segments of the CT protein identified herein as SEQ ID NO 2 or 4. Polypeptides identified herein as SEQ ID NOS 5–10, CTfn3, CTfn6, CTfn3–6, and CTfg are also useful in this regard.

In another embodiment, a composition according to the present invention comprises a CT protein or polypeptide exhibiting a cell-attachment activity in substantially pure form, attached to a solid support or substrate. The solid support may be a prosthetic device, implant, or suturing device designed to have a surface in contact with neuronal cells or the like; further, it may be designed to lessen the likelihood of immune system rejection, wherein said surface of said device is coated with a polypeptide exhibiting a cell-attachment activity.

The present invention also discloses a substantially pure polypeptide derived from CT, wherein said polypeptide has cell-attachment-promoting activity. In various embodiments, the polypeptide is selected from the group consisting of CTfn3, CTfn6, CTfn3–6, and CTfg. In other variations, the polypeptide is linked to a solid support or substrate to form a useful composition.

A CT-derived polypeptide having cell attachment-promoting activity according to the present invention is preferably not more than 100 amino acid residues in length. In various preferred embodiments, a CT polypeptide is at least three (3) amino acids in length; in another variation, a CT polypeptide is fewer than 50 amino acid residues in length. A CT polypeptide is preferably selected from the group consisting of CTfn3, CTfn6, CTfn3–6, and CTfg. In another embodiment, a CT polypeptide may be linked to a solid support or substrate.

EXAMPLES

The following examples are given for illustrative purposes only and do not in any way limit the scope of the invention.

Example 1

Preparation of Fusion Proteins and Polypeptides

CT is a multidomain protein which has several different functions in vivo. These functions comprise cell attachment followed by cell spreading and neurite outgrowth. In order to associate the various functions of CT with specific CT domains, recombinant protein fragments of CT were made which contain specific regions spanning almost the entire CT molecule. Cell attachment, morphology, percent sprouting, and neurite outgrowth of cells plated on substrata coated with each of the CT fragments were then analyzed.

A. Descrnntion of CT Fusion Proteins and Polypeptides

Ten different protein expression vectors were constructed to express CT fusion polypeptides. Five of these constructs, CTegf, CTfn–2, CTfn3, CTfn7–8, and CTfg were made in the pGEX-2T and pGEX-3X vectors (Pharmacia, Uppsala, Sweden) (Prieto, et al., *J. Cell Biol.* 119: 663–678 (1992) and Prieto, et al., *Proc. Natl. Acad. Sci. USA* 90: 10154–10158 (1993)). Five of these constructs, CTfn4, CTfn5, CTfn6, Ctfnspl, and Ctfn3–6 (a construct comprising the CTfn3 and CTfn6 regions) were made in the pGEX-4T2 vector (Pharmacia, Uppsala, Sweden).

When DNA encoding the CT polypeptide is inserted into the pGEX vectors in the same translational frame as the DNA encoding the glutathione-S-transferase (GST) protein domain, a fusion protein consisting of the carboxy-terminal portions of GST fused to the CT polypeptide is expressed. GST provides a means for the purification of the CT:GST fusion protein from the other *E. coli* cellular components.

The CT:GST fusion proteins are designated and can be described based on the portion of CT that they encode, as shown in Table 1. The amino acid residues of chicken CT (SEQ ID NO 4) which correspond to the amino acid residues of each CT:GST fusion proteins is indicated in Table 1. Roman numerals were used to designate the individual chicken fibronectin (fn) type III repeats as illustrated in FIG. 1. The fibronectin (fn) type III repeat designations correspond to those originally used in the literature by Jones, et al., *PNAS* 85: 2186–2190 (1988); Jones, et al., *PNAS* 86: 1905–1909 (19891; Weller, et al., *J. Cell Biol.* 112: 355–362 (1991). In addition, five amino acids from both the preceding and the following fn type III repeats were included in the fn type III constructs CTfn1–2 and CTfn3 to facilitate proper folding of the individual CT type III protein domains. CTegf contains all the EGF-like repeats, CTfn1–2 contains the proximal fibronectin type III repeats (I–II); CTfn3 contains the fibronectin type III repeat (III); CTfn4 contains the fibronectin type III repeat (IV); CTfn5 contains the fibronectin type III repeat (V); CTspl contains the alternatively spliced fibronectin type III repeats (VaVbVc); CTfn6 contains the fibronectin type III repeat (VI); CTfn3–6 contains the fibronectin type III repeats (III and VI); CTfn7–8 contains the last two fibronectin type III repeats with the exception of the 13 amino-terminal amino acids of repeat VIII (VII and VIII); and CTfg contains the entire fibrinogen domain and includes the 13 amino-terminal amino acids of fibronectin repeat VIII.

TABLE 1

| Clone Designation | SEQ ID NO | Region | Amino Acid Residue |
|---|---|---|---|
| egf | 4 | EGF repeats | 1–591 |
| fn1–2 | 4 | I-II | 592–773 |
| fn3 | 4 | III | 774–864 |
| fn4 | 4 | IV | 866–956 |
| fn5 | 4 | V | 957–1044 |
| fn6 | 4 | VI | 1318–1398 |
| spl | 4 | VaVbVc | 1045–1317 |
| fn7–8 | 4 | VII-VIII | 1132–1569 |
| fn3–6 (or fn3/6) | 29 | III/VI | 774–864/1318–1398 |
| fg | 4 | VIII-fg | 1570–1810 |

B. Construction of CT Fusion Protein Expression Vectors

Fusion proteins comprising a preselected portion of CT and the GST domain were expressed from pGEX vectors (Pharmacia, Piscataway, N.H.). The pGEX plasmids are designed for inducible, high-level intracellular expression of genes or gene fragments as fusions with *Schistosoma japonicum* glutathione S-transferase (GST) (Smith, et al., *Gene* 67: 31 (1988)). The CT:GST fusion proteins are purified from bacterial Iysates by affinity chromatography using glutathione-Sepharose 4B. Elution from the glutathione-Sepharose 4B using reduced glutathione provides very mild elution conditions for the release of the CT:GST fusion protein from the affinity matrix, thereby minimizing effects on functional activity of the fusion protein.

The multiple cloning sites of the pGEX vectors provide for the unidirectional insertion of cDNA inserts. The primary differences between the various PGEX vectors used herein—i.e., pGEX-2T, pGEX-3X, and pGEX-4T2—are the restriction sites and the reading frame of the restriction sites present in the multiple cloning site. The strategies described herein which were used to generate the pGEX vectors to express the CT:GST fusion proteins were adapted to insert the CT-DNA homologs into the appropriate vector to place the CT and GST DNA coding regions in the same translational reading frame.

1. Preparation of CT-DNA Homologs

The detailed construction of the vectors for the expression of CTegf, CTfn7–8, and CTfg is described in Prieto, et al., J. Cell Biol. 119: 663–678 (1992). CTfn7–8, as described in Prieto et al., was renamed CTfn3 for use in this invention. The CT cDNA fragments corresponding to the fn type III repeats were excised from pEC802 (Jones, et al., PNAS 85: 2186–2190 (1988)) and pEC801 (Jones, et al., PNAS 86: 1905–1909 (1989); Prieto, et al., J. Cell Biol. 119: 663–678 (1992)) by restriction digestion to generate the CT-encoding DNA fragments. The CT-encoding DNA fragments were then inserted into one of the pGEX expression vectors to express a fusion protein consisting of a CT fragment fused to GST (CT:GST fusion protein).

Four different templates were used as sources of CT-encoding cDNA. The plasmid vectors with CT-encoding cDNA inserts were pEC801 (Jones, et al., PNAS 86: 1905–1909 (1989); Prieto, et al., J. Cell Biol. 119: 663–678 (1992)), pEC802 (Jones, et al., PNAS 85: 2186–2190 (1988)), pEC803 (Jones et al., PNAS 89:2019–2095 (1992)); and pCG2 (Jones, et al., PNAS 86: 1905–1909 (1989). The CT-encoding cDNA inserts comprise alternatively spliced CT-encoding cDNA inserts and different portions of the CT-encoding cDNA. pEC802 and pEC803 contain cDNA encoding a part of CT as described in Jones et al., PNAS 85:2186–2190 (1988). pCG2 contains the 3' region of the cDNA encoding CT which spans bp 4,515 to bp 6,061. All base pair numbering is as given in Jones et al., PNAS 85: 2186–2190 (1988).

The plasmid pEC801 was used as the template for the preparation of the pGEX-2T vector which expresses an EGF:GST fusion protein. The plasmid pEC801 contains a CT-encoding cDNA which comprises the EGF and fn type III regions of CT including the alternatively spliced region VaVbVc (Jones et al., PNAS 86: 1905–1909 (1989)). To prepare the EGF-encoding DNA fragment, 10 µg of the λgt11 bacteriophage DNA was incubated in 1×restriction digest buffer (150 mM NaCl, 8 mM Tris-HCl, pH 7.5, 6 mM MgSO$_4$, 1 mM DTT, 200 µg/ml BSA) with the restriction enzyme EcoRI (30 units) and incubated at 37° C. for 2 hours. The resulting fragment spanned the EGF-like repeats of CT from base pair (bp) 830 to 2182. After gel electrophoresis of the digest products, the region of the gel containing the EGF-encoding DNA fragment of the appropriate number of base pairs was excised, the DNA purified by standard methods, and ethanol precipitated and re-suspended in a TE solution containing 10 mM Tris-HCl, pH 7.5 and 1 mM EDTA at a final concentration of 100 ng/µl. The resulting EGF-DNA homologs have cohesive termini adapted for directional ligation to the vector pGEX-2T.

The prepared EGF-DNA homolog was then directly inserted by directional ligation into the pGEX-2T expression vector. The pGEX-2T expression DNA vector was prepared for insertion of the EGF-DNA homolog by admixing 1 µg of the pGEX-2T vector DNA to a solution containing 10 units of the restriction endonuclease EcoRI and a buffer recommended by the manufacturer. This solution was maintained at 37° C. for 2 hours. The digestion product was purified by extracting the solution with a mixture of phenol and chloroform followed by ethanol precipitation. The pGEX-2T expression vector was then ligated to the EGF-DNA homologs prepared as described above.

The EGF-DNA homolog was directly inserted into the pGEX-2T expression vector by ligating approximately three moles of EGF-DNA homolog insert with each mole of the pGEX-2T expression vector at 4° C. for 16 hours in the presence of T4 DNA ligase under conditions recommended by the manufacturer. The ligation mixture containing the EGF-DNA homologs inserted into the pGEX-2T vector were transformed into the E. coli strain NM522 (Stratagene, La Jolla, Calif.) according to the manufacturer's specifications. An NM522 colony containing the pGEX vector construct which expresses an EGF:GST fusion protein was selected by plating the transformation mixture on agar plates containing L-broth and ampicillin (Maniatis, Molecular Cloning: A Laboratory Manual, Cold Spring Harbor Laboratory, Cold Spring Harbor, N.Y. (1982)).

The pGEX-2T expression vector, which expresses a CTfg:GST fusion protein, was prepared by digestion of the plasmid pCG2 with BglII and XmnI to excise a 1,020-bp cDNA insert. The resulting 1,280-bp insert spans bp 5,013 at the BglII site to 6,033 at the XmnI site. The overhanging ends of the cDNA insert were filled in to generate blunt ends by incubation with 1 Unit of T4 DNA polymerase in 1×buffer (30 mM tris-acetate, pH 8.0; 70 mM potassium acetate; 10 mM magnesium acetate; 0.5 mM dithiothreitol; 0.1 mg/ml bovine serum albumin; 10 µM of each dNTP) and incubating at 37° C. for 15 minutes (Maniatis, Molecular Ctonina: A Laboratory Manual, Cold Spring Harbor Laboratory, Cold Spring Harbor, N.Y. (1982)). The cDNA insert was then inserted into the pGEX-2T vector which had been digested with the SmaI restriction enzyme as described above. The blunt ends of the cDNA inserts generated by Kienow fill-in reaction were ligated to the SmaI digest-generated ends of pGEX-2T. The ligated pGEX-2T and CTfg inserts were transformed into NM522 and a colony containing the pGEX vector construct which expresses a CTfg fusion protein was identified using the same methods described above. The orientation of CTfg cDNA insert in the same translational reading frame as the GST protein domain and which would express the fg:GST fusion protein from the pGEX-2T vector was determined by digestion with additional restriction enzymes.

The pGEX-3X expression vector which expresses a CTfn7–8:GST fusion protein was prepared by digestion of pEC803 (Jones et al., PNAS 89: 2091–2095 (1992)) with EcoRI and BglII to excise a 500-bp CTfn7–8-encoding DNA fragment. The EcoRI and BglII ends were filled in using T4 DNA polymerase to generate blunt ends as described in Maniatis, Id., (1982). The blunt ended cDNA fragment, from bp 4513 at the EcoRI site to bp 5013 at the BglII site of CT, was then ligated with pGEX-2T that had been digested with the restriction enzyme SmaI. The ligated pGEX-3X and CTfn7–8 cDNA insert were then transformed into NM522 and ampicillin resistant colonies containing the pGEX vector construct with a CTfn7–8:GST cDNA insert in the orientation which would express a CTfn7–8:GST fusion protein were selected using the same methods described above.

The next set of PGEX vectors to express CT:GST fusion proteins were generated by PCR amplification of specific regions of the CT cDNA molecule. The restriction sites EcoRI and BamHI were incorporated into the 5' and 3' PCR primers, respectively. The PCR primers were designed to generate a CT cDNA insert in the correct translational frame and orientation so that a CT:GST fusion protein would be expressed from the PGEX vector.

Figure 1:
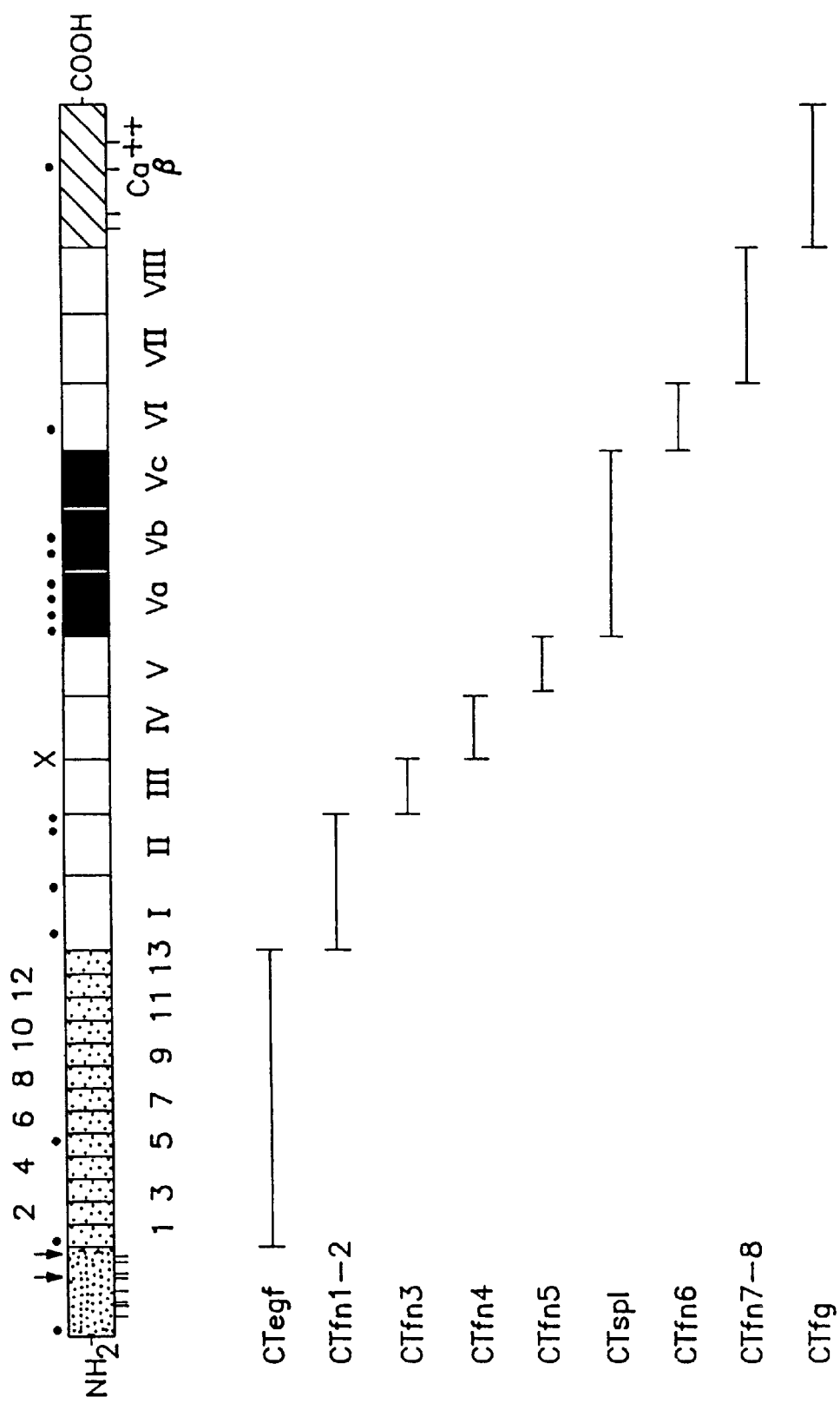
FIG. 1 illustrates a model of cytotactin (CT) and the regions of CT which were examined in the pGEX protein expression system as described in Example 1. The complete nucleotide and amino acid residue sequences of chicken CT, including the alternatively spliced region VaVbVc, are given in SEQ ID Nos 3 and 4, respectively. The primary structure of CT is shown at the top of the figure. CT consists of several protein domains and are given in order from the amino- to the carboxy-terminus: amino-terminal region (▨). EGF-like repeats (▨), fn type III repeats (□), alternatively spliced repeats (VaVbVc) (■), and fibrinogen region (□). The dots above the structure represent potential glycosylation sites, small lines below the structure denote cysteine residues. The arrows are potential glycosaminoglycan addition sites and the Arg-Gly-Asp (RGD) site is represented by a cross. A $Ca^{2+}$ site in the region of the fibrinogen β chain is also indicated below the structure.

The cDNA regions that were amplified corresponded in the chicken to fn type III repeats numbered according to Jones, et al., PNAS 86: 1905–1909 (1989)): EGF repeats, I–II, III, IV, V, VaVbVc, VI, VII–VIII, and fg (FIG. 1).

The polynucleotide primers for use in the PCR reactions can be prepared using any suitable method, such as, for example, the phosphotriester or phosphodiester methods. (See Narang et al., Meth. Enzymol. 68: 90 (1979); U.S. Pat. No. 4,356,270; and Brown et al., Meth. Enzymol. 68: 109 (1979), the disclosures of which are incorporated by reference herein.) All primers and synthetic polynucleotides described herein were synthesized on an Applied Biosystems DNA synthesizer, model 381A, following the manufacturer's instructions.

The nucleotide sequences of the PCR primers used to generate the cDNA-encoding specific regions of CT are given in Table 2. The cDNA regions that were amplified are designated in Table 2 under the CT column. The corresponding SEQ ID NO and the nucleotide sequence of the primers is given from the 5' to 3' direction. When preparing the Ctfn3/6 construct, the primers having SEQ ID NOS 22, 26, 27 and 28 are preferably used, although some alternates are also useful, as shown.

Various restriction sites were incorporated into the primers to facilitate insertion of the CT-encoding cDNA into the appropriate pGEX vector. The EcoRI sites are shown with single underlining; the BamHI sites are double-underlined; and the XhoI restriction sites are shown in bold type.

agarose gel electrophoresis. The amplified CT-coding DNA homolog was seen as a major band of the expected size. The CT-encoding DNA homolog prepared above is then inserted into pGEX-4T2 vector and the encoded CT:GST fusion protein is expressed.

2. Insertion of CT-DNA Homologs into DGEX Protein Expression Vectors

The PCR products were subcloned in the appropriate restriction sites of pGEX-2T, pGEX-3X, or pGEX-4T2 (Pharmacia) to generate in-frame constructs for expression of a CT:GST fusion protein. To construct a pGEX expression vector, CT-DNA homologs were prepared according to Example 1.B.1. using the primers shown in Table 2. The resulting PCR-amplified products (2.5 $\mu$g/30 $\mu$l of 150 mM NaCl, 8 mM Tris-HCl, pH 7.5, 6 mM $MgSO_4$, 1 mM DTT, 200 $\mu$g/ml BSA) are digested at 37° C. with restriction enzymes EcoRI (20 units) and BamHI (20 units). The CT-DNA homologs are purified on a 1% agarose gel using

TABLE 2

| CT (SEQ ID NO) | Nucleotide Sequence |
|---|---|
| 5'fn1-2 (13) | 5' TAATTGGGATCCGGGATCGACTGTTCTGATGTGTCT 3' |
| 3'fn1-2 (14) | 5' TAATTGGAATTCAGGGGCATCGAGTTTTGTG GTTAT 3' |
| 5'fn3 (15) | 5' TAATTGGAGTCCGAGTGATAACCCAAAACTCGATGC 3' |
| 3'fn3 (16) | 5' TAATTGGAATTCTGGAGCATCCAAGTCTGTGACAAA 3' |
| 5'fn4 (17) | 5' GCGGGATCCGACTTGGATGCTCCACG 3' |
| 3'fn4 (18) | 5' GCGGAATTCAGTGCCAGCATTAATGGTAGC 3' |
| 5'fn5 (19) | 5' GCGGGATCCGATCTTGATAACCCCAAGGAC 3' |
| 3'fns (20) | 5' GCGGAATTCAGTCGAACCCTTGATGGT 3' |
| 5'fn6 (21) | 5' GCGGATCCGTTGTGGGATCTCCCAAG 3' |
| 3'fn6 (22) | 5' GCGCTCGAGTGTTTTCAGAATTCCAGAAATGGGTTCGC 3' |
| 5'fnspl (23) | 5' TAATTGGATCCCGAGGAAGAACCTGAGCTTGGAAACTTA 3' |
| 3'fnspl (24) | 5' TAAATTGAATTCTGTGGTTGCTACTGAATTTATGGGTTG GGAGCG 3' |
| 3'fn3 (26) | 5' GCGGGATCCAAACTCGATGCCCCTAGC 3' |
| 5'fn3 (27) | 5' GCGCTCGAGTGTGACAAAGACCTT 3' |
| 5'fn6 (28) | 5' GCGCTCGAGGTTGTGGGATCTCCCAAG 3' |

PCR amplification was performed using two different plasmids, pEC802 and pEC803, as the CT-encoding template. The complete nucleotide and amino acid residue sequences of the CT-encoding cDNA, including the VaVbVc region, are given in SEQ ID NO 3 and 4, respectively. CTfn3, CTfn4, CTfn5, and CTfn6 were prepared using pEC802 as the source of the CT-encoding cDNA template. CTfnspl was prepared using pEC803 as the source of the CT-encoding cDNA template. The nucleotide sequences of the 5' and 3' primers which correspond to each of the CT regions amplified are shown in Table 2. For example, 5'fn3 refers to the 5' primer used to amplify the CT region fn3.

PCR amplification is performed in a 100 $\mu$l reaction containing approximately 100 nanograms (ng) of the chicken CT cDNA template, 100 ng of 3' primer, 100 ng of the 5' primer (Table 2), 200 mM of a mixture of dNTP's, 50 mM KCl, 10 mM Tris-HCl pH 8.3, 1.5 mM $MgCl_2$, 0.001% gelatin and 2.5 units of Thermus aquaticus (Taq) DNA polymerase. The reaction mixture is overlaid with mineral oil and subjected to 30 cycles of amplification. Each amplification cycle includes denaturation at 93° C. for 1 minute, annealing at 48° C. for 1 minute and polynucleotide synthesis by primer extension (elongation) at 72° C. for 2 minutes. The amplified CT-coding DNA homolog-containing samples are then extracted twice with phenol/chloroform, once with chloroform, ethanol precipitated and are stored at −70° C. in 10 mM Tris-HCl, pH 7.5, and 1 mM ethylenediaminetetraacetic acid (EDTA).

CT-coding DNA homolog synthesis and amplification from the chicken CT DNA template was visualized by a standard technique as described in Maniatis, Id., (1982). After gel electrophoresis of the digested PCR amplified CT-DNA homologs, the region of the gel containing DNA fragments of the appropriate number of base pairs is excised, purified by a standard technique, ethanol precipitated and re-suspended in a solution containing 10 mM Tris-HC1, pH 7.5 and 1 mM EDTA (TE) to a final concentration of 100 ng/$\mu$l. The resulting CT-DNA homologs have cohesive termini adapted for directional ligation to the vectors pGEX-2T, pGEX-3X, and pGEX-4T2 (pGEX). These prepared CT-DNA homologs are then directly inserted by directional ligation into linearized pGEX expression vectors which were prepared as described below.

The pGEX expression DNA vectors were prepared for insertion of a DNA homolog by admixing 10 $\mu$g of the pGEX vector DNA to a solution containing 20 units each of the restriction endonucleases EcoRI and BamHI and a buffer recommended by the manufacturer. This solution was maintained at 37° C. for 2 hours. The DNA was purified by extracting the solution with a mixture of phenol and chloroform followed by ethanol precipitation. The pGEX expression vector was ready for ligation to the CT-DNA homologs prepared in the above example. These prepared CT-DNA homologs were then directly inserted into the EcoRI and BamHI restriction digested PGEX expression vector that was prepared above by ligating approximately three moles of CT-DNA homolog inserts with each mole of the PGEX expression vector in the presence of T4 DNA ligase using the manufacturer's recommended conditions.

The ligation mixtures containing the CT-DNA homologs were transformed into the E. coli strain NM522 (Stratagene, La Jolla, Calif.) according to the manufacturer's specifications and selected with ampicillin.

3. Nucleotide Sequence Determination of the CT-DNA Homologs

The nucleotide sequence of the CT-DNA homologs was confirmed by the dideoxynucleotide chain-termination method using Sequenase (United States Biochemical, Columbus, Ohio) (Sanger, et al., PNAS 74: 5463–5467 (1977)) and the 5' pGEX sequencing primer (5'- GGGCTG-GCAAGCCACGTTTGGTG -3')(SEQ ID NO: 30) (Pharmacia). No nucleotide changes were observed in the PCR products.

C. Expression and Purification of CT Fusion Proteins

The fusion proteins consisting of a portion of the CT molecule and GST (CT:GST fusion protein) were expressed in E. coli NM522 cells (Stratagene, La Jolla, Calif.) from the PGEX protein expression vectors constructed in Example 1.B.1. Although the GST domain can be removed from the CT:GST fusion protein to generate a protein encoding only CT during the purification procedure, previous experiments had indicated that GST alone did not contribute to cell adhesion (Prieto et al., J. Cell Biol. 119: 663–678 (1992)). Therefore, removal of the GST domain was not performed in these assays; however, the GST domain was expressed from the pGEX-2T vector and included in these assays. The CT:GST fusion and GST proteins were then purified from other cellular components by selectively binding the CT:GST fusion protein in a cell lysate to glutathione-Sepharose 4B via the GST portion of the fusion protein. The bound protein was extensively washed to remove E. coli cellular components and the purified CT:GST fusion or GST protein was specifically eluted from the glutathione-Sepharose 4B as described below.

An ampicillin-resistant NM522 colony containing the PGEX vector which expresses one of the CT:GST fusion proteins was used to inoculate 100 ml of LA-broth (L-broth with 50 μg/ml ampicillin) and incubated at 37° C. with agitation for 10 hours. These cultures were then used to inoculate 900 ml of LA-broth and incubated for 3 to 4 hours at 25° C. with agitation until an optical density of 1.0 at 650 nm was reached. Expression of the fusion protein was then induced by the addition of 0.1 millimolar (mM) isopropyl-β-D-thiogalactopyranoside (IPTG, Sigma, St. Louis, Mo.) and incubation for 20 hours at 25° C. with agitation.

The bacteria were harvested by centrifuging at 9,000 rpm in a GSA rotor for 10 minutes. The bacterial pellet was resuspended in a lysis buffer (50 mM tris-HCl, pH 7.5; 0.1% NP-40; and 1 mM $MgCl_2$). The bacterial resuspension was then lysed by french press and clarified by centrifugation at 10,000 rpm in an SS34 rotor for 20 minutes to pellet the bacterial debris. The clarified supernatant containing the CT:GST fusion or GST protein was incubated with 14 ml of glutathione-Sepharose 4B beads (Pharmacia) at 4° C. for 1 hour with gentle rotation. The fusion or GST protein bound to the glutathione-Sepharose 4B beads was then washed extensively with a washing buffer (20 mM tris-HCl, pH 7.5 and 1 mM dithiothreitol) to remove unbound bacterial debris.

The fusion or GST protein was specifically eluted from the glutathione-Sepharose 4B beads serially three times with two bead volumes of elution buffer by incubation in elution buffer (50 mM tris-HCl, pH 8.0 and 1 mM reduced glutathione). The eluate was dialyzed against distilled water and lyophilized. The lyophilized CT:GST fusion or GST protein was dissolved in sterile phosphate buffered saline (PBS), the protein concentration determined, and aliquots of the protein stored at −70° C.

The molecular weight and purity of the eluted proteins was determined by sodium dodecyl sulfate-polyacrylamide gel electrophoresis (SDS-PAGE). The GST was not cleaved from the CT:GST fusion protein during purification, therefore, the molecular weight of the fusion protein includes 26,000 kDa of the GST protein. Three pg of the purified CT fusion proteins were admixed with an equal volume of 2×SDS-PAGE load buffer (200 mM tris-HCl, pH 8.6; 0.005% (w/v) bromophenol blue, 20% (v/v) glycerol) and the proteins separated electrophoretically on a single-well 10% SDS-PAGE with 1×SDS-PAGE running buffer (25 mM tris-base, 192 mM glycine, pH 8.5). The separated proteins were visualized by staining the proteins with Coomassie Blue and the apparent molecular weight ($M_r$) determined by comparison to protein molecular weight standards (Table 3). The GST was not cleaved from the CT:GST fusion protein during purification, therefore, the molecular weight of the fusion protein indicated in Table 3 includes 26,000 kDa of the GST protein. The GST protein, expressed from pGEX-2T, has an $M_r$ of 26,000 kDa.

TABLE 3

| CT:GST Fusion Protein | Predicted M, (kDa) |
|---|---|
| CTegf | 72,600 |
| CTfn1–2 | 50,500 |
| CTfn3 | 36,500 |
| CTfn4 | 36,500 |
| CTfn5 | 36,500 |
| CTfn6 | 36,100 |
| CTfn7–8 | 44,400 |
| CTfnsp1 | 56,000 |
| CTfg | 63,300 |

The results, as demonstrated by SDS-PAGE analysis, indicate that the CT:GST fusion proteins isolated, eluted, and electrophoresed on a 10% SDS-PAGE gel, according to the aforementioned procedure, had relative molecular weights at the anticipated apparent Mr. Therefore, results of the Coomassie Blue-stained SDS-PAGE gels indicated that CT:GST fusion proteins of the appropriate weights were expressed and purified. Results of the SDS-PAGE analysis indicate that samples CTfn3, CTfn6, and CTfn7–8 contained more than one protein. These sample proteins represent the CT:GST fusion protein and degradation products of the CT:GST fusion protein. Sufficient amounts and purity of the CT:GST fusion proteins were isolated via this procedure for use according to the within-disclosed methods and procedures.

Example 2

Preparation of Monoclonal Antibodies

Briefly, BALB/c mice are immunized via sequential intraperitoneal immunizations with 50 μg of immunogen (preferably purified) in CFA (complete Freund's adjuvant; Calbiochem, San Diego, Calif.). As described previously, immunogens are selected from SEQ ID NOS 2 and 4–10. Polypeptides identified herein as CTfn3, CTfn6, and CTfn3–6 are also useful as immunogens, as are proteins and polypeptides substantially homologous thereto.

Subsequently, hybridomas are generated according to the methods described in Section E.1. hereinabove. (Also see Ausubel, et al. (eds.), Current Protocols in Molecular Biology, John Wiley & Sons, NY (1994), Chp. 11, for a description of useful methods of generating, identifying, and purifying monoclonal antibodies.)

Screening strategy for antibody selection generally comprises analysis of the reactivity of hybridoma culture fluids with immunogen (if a polypeptide is used) as well as with intact cytotactin (CT). Hybridomas reacting with the immunogen (e.g., CTfn3) are selected for antibody production and are preferably established by two to four times sequential subclonings by limiting dilution. A variety of screening methods for the detection, purification, and characterization of specific antibodies are available in the art. For example, a variety of direct and indirect ELISA methods, RIA methods, immunoaffinity and Western blotting methods are described in Ausubel, et al. (eds.), *Current Protocols in Molecular Biology*, John Wiley & Sons, NY (1994) (see esp. Chp. 11).

IgG fractions from the hybridomas may be purified by affinity chromatography using the MAPS II system (Monoclonal Antibody Purification System, BioRad, Richmond, Va.) or hydroxylapatite columns (Bio-Rad). Purification of antibodies from ascites fluid by affinity chromatography on protein A-sepharose CL4B (Pharmacia, Uppsala, Sweden) is another useful method. Monoclonal antibody affinity columns for use therewith are prepared by coupling isolated IgG to CNBr-activated Sepharose 4B (Pharmacia) to a final concentration of 2 mg IgG per ml resin.

Monoclonal antibodies may also be purified via FPLC, according to established protocols. Immunopurified antibodies may be isolated from purified CT immobilized on Affigel 15 (BioRad, Richmond, Calif.) according to the manufacturer's directions.

Immunoscreening of monoclonal antibodies may be performed via radioimmunoassay (RIA), ELISA, or various other methods. For example, solid-phase RIA may be performed essentially as follows.

Tissue culture supernatants from wells appearing to contain viable hybridomas after about 14 days of culturing are screened by RIA for the presence of anti-CT protein or polypeptide antibody molecules. Briefly, 100 microliters ($\mu$l) of phosphate-buffered saline (PBS) containing either 1 $\mu$g/ml of immunogen (e.g., CT) or another protein (control) are admixed into the wells of flat-bottom 96-well polyvinyl microtiter plates as solid phase matrix. The plates are then maintained for about 16–20 hours at 4° C. to permit the immunogen or control protein to adsorb onto the surface of the wells to form a solid support. The coating solution is removed by shaking, the wells are rinsed, and 100 $\mu$l of blocking solution (PBS containing 5% normal goat serum) is admixed into each well to block excess protein binding sites.

The wells are maintained for about 30–60 minutes at 37° C. and then the blocking solution is removed. Into each well is then admixed 100 $\mu$l of either (a) hybridoma tissue culture supernatant diluted 1:10 in PBS, or (b) hybridoma supernatant diluted 1:10 in PBS containing 100 $\mu$g/ml immunogen (e.g., CT) as a competitive inhibitor. The immunoreaction admixtures thus formed are maintained at room temperature for about 16–20 hours or at 37° C. for about 1–2 hours, to permit the formation of a solid phase-bound immunoreaction product and a liquid phase, including any non-bound monoclonal antibody molecules.

To each well is then admixed 100 $\mu$l of $^{125}$I-labeled goat anti-mouse IgG. The labeling immunoreaction admixture thus formed is maintained about 6–20 hours at 4° C. to permit formation of a $^{125}$I-labeled second solid-phase immunoreaction product. The solid and liquid phases are separated to remove any non-bound $^{125}$I-goat anti-mouse IgG.

The amount of $^{125}$I-bound to each well is determined by gamma scintillation.

The presence of at least about 3 times the amount of non-specifically bound $^{125}$I, as determined from the control wells and an immunogen-coated well, indicate the presence of anti-immunogen antibodies in a tissue culture supernatant. A reduction of solid-phase bound $^{125}$I by no more than about 15% by the presence of liquid-phase immunogen (e.g., CT) competitor in the immunoreaction admixture indicates the presence of an anti-immunogen antibody in the tissue culture supernatant.

Alternatively, following the formation of a first solid-liquid phase immunoreaction admixture, fifty $\mu$l of $^{125}$I-labeled immunogen prepared as described above is admixed into each well to form a second solid-liquid phase immunoreaction admixture. The wells are maintained for 2 hours at 37° C. and then rinsed three times to isolate the solid-phase bound $^{125}$I-immunogen-containing immunoreaction products. Excess liquid is removed by aspiration and the wells are allowed to dry. Individual wells are cut apart and the $^{125}$I contained in each well is determined with a gamma counter.

Another useful procedure is that described in Husmann, et al., *J. Cell. Biol.* 116: 1475–1486 (1992), which procedure may be described essentially as follows. Lou x Sprague Dawley F1 hybrid female rats are immunized with immunogen (e.g., any one of SEQ ID NOS 2 or 4–10). The rats are immunized for the first time with 50 $\mu$g of immunogen in 1 ml PBS, pH 7.4, mixed with an equal volume of complete Freund's adjuvant and three or four times subsequently with 50 $\mu$g immunogen in incomplete Freund's adjuvant at time intervals of 3–5 weeks, all subcutaneously.

Animals with serum titers between 1:5,000 and 1:10,000 dilution as determined by ELISA (see below) are chosen for fusion. The rats receive two final intraperitoneal injections, each with 20 $\mu$g of the immunogen in PBS, 4 and 3 days before the fusions. Fusions are carried out with the mouse myeloma clone X-Ag8-653 (Kearney, et al., *J. Immunol.* 123: 1548–1550 (1979)) following established procedures (Lagenaur, et al., *Dev. Biol.* 79: 367–378 (1980)) with minor modifications (Faissner and Kruse, *Neuron* 5: 627–637 (1990)).

Hybridoma culture supernatants are screened by ELISA using purified immunogen and are further tested by Western blot analysis. Competition ELISA is used to identify antibodies that recognize epitopes different from each other. Corresponding hybridoma cells are then subcloned twice by limiting dilution (see, e.g., Lagenaur, et al., Id. (1980)).

For ELISA, wells of micro-test flexible assay plates (Falcon 3912; Becton Dickinson Labware, Oxnard, Calif.) are coated overnight at 4° C. with polypeptide immunogen or CT (100 $\mu$l/well at 0.5 $\mu$g/ml 0.1 M NaHCO$_3$). Wells are washed with PBS, incubated for 1 hour at 37° C. with 0.1 M NaHCO$_3$ containing 5 mg/ml BSA, washed three times with PBS, and incubated for 3 hours at 37° C. with hybridoma supernatants and mAbs. After three washes with PBS, wells are incubated for 2 hours at 37° C. with HRP-coupled goat anti-rat IgG and IgM polyclonal antibodies, washed three times, and developed with 1 mg/ml ABTS (2, 2'-azino-di-[3-ethylbenzthiazoline sulfonate (6)]; Boehringer Mannheim Biochemicals) in 100 mM Na-acetate, 50 mM Na-phosphate (pH 4.2), and 0.01% H$_2$O$_2$. The optical density is measured at 405 nm with an ELISA reader (e.g., Titertek Multiskan MKII, Flow).

Competition assays may be conducted according to the method of Friguet, et al. (*J. Immunol. Methods* 60: 351–358

(1983)), essentially as follows. Hybridoma supernatants of mAbs to be compared are incubated together with CT coated onto assay plates as described for the ELISA. In parallel, wells are incubated individually with each antibody. Hybridoma supernatants of mAbs indicating an increase in absorbance when incubated together in comparison to being incubated individually are taken to recognize different epitopes on the CT molecule. As a positive control, mAbs known to recognize different epitopes may be incubated together. As a negative control, a twofold amount of hybridoma supernatants or mAbs is incubated.

Larger quantities of mAbs are obtained by growing the hybridoma clones in RPMI 1640 (Gibco Labs, Grand Island, N.Y.) supplemented with 1% (vol/vol) Nutridoma (Boehringer Mannheim Biochemicals, Indianapolis, Ind.). Culture supernatants are concentrated by ammonium sulfate precipitation and dialyzed against PBS. Purification may be confirmed via SDS-PAGE.

Example 3

Preparation of Polyclonal Antibodies

The various immunogens used herein are prepared as described in Example 2 above. Immunizations and procedures for the collection and screening of polyclonal antisera are also conducted in the manner disclosed in Example 2 herein, or according to other accepted protocols. An exemplary protocol is essentially as follows.

Add 2 ml complete Freund's adjuvant to 2 ml purified immunogen (1–2 mg/ml in PBS). Emulsify the mixture according to standard protocols and administer the emulsion to an animal (e.g., a rabbit) via intramuscular, subcutaneous, or intraperitoneal means. Boost the rabbit intramuscularly about 4 weeks later with 1 mg antigen emulsified in incomplete Freund's adjuvant (1:1). Repeat the booster immunization two weeks after the initial boost.

Bleed the animal from the marginal vein of the ear 10 days after the second booster immunization. Allow the blood to stand at room temperature several hours before placing it overnight at 4° C. Once formed, gently loosen the clot from the sides of the tube and remove it. Transfer the serum into an appropriate centrifuge tube and pellet any remaining RBCs and debris via centrifugation (10 min. at 5,000×g).

Administer further booster immunizations at 2-week intervals, bleeding the animal 10 days after each boost. Determine the specific antibody titer of the antiserum by ELISA or RIA, according to standard protocols. (See, e.g., Ausubel, et al., Id. (1994).) If desired, purify the specific antibody population following standard procedures (Id.).

The preparation and characterization of a variety of rabbit anti-CT polyclonal antibodies is also described in Hoffman, et al., *J. Cell Biol.* 106: 519–532 (1988); Wehrle and Chiquet, *Development* 110: 401–415 (1990); Lochter, et al., *J. Cell Biol.* 113: 1159–1171 (1991); and Wehrle-Haller, et al., *Develooment* 112: 627–637 (1991), the disclosures of which are incorporated by reference herein.

Typically, purification of polyclonal antibodies is accomplished as described above with regard to monoclonal antibodies. Purified 1g fractions of anti-CT rabbit polyclonal antiserum may be prepared by ammonium sulfate fractionation and chromatography on DEAE Sephadex. Immunopurified antibodies are isolated from purified CT immobilized on Affigel 15 (BioRad, Richmond, Calif.) according to the manufacturer's directions.

Alternatively, purification of the antibodies may be accomplished following the standard protocols described in Ausubel, et al. (eds.), *Current Protocols in Molecular Biology*, John Wiley & Sons, NY (1994), (see esp. Chp. 11), the disclosures of which are incorporated by reference herein. For example, the antibodies may be precipitated with saturated ammonium sulfate or fractionated by chromatography on DEAE-Affi-Gel Blue (Bio-Rad), according to the manufacturer's instructions.

Example 4

Preparation of Anti-Idiotype Antibodies

An appropriate immunogen—e.g., an anti-CTfn3 antibody—is prepared and administered as described in Example 2 above. Typically, emulsions (200–400 µl/mouse) of equal volumes PBS containing 25–100 µg immunogen and complete Freund's adjuvant are prepared and injected into the animal to be immunized—e.g., a mouse. Following subsequent boosting, the animal is bled and antibody is collected. Once the titer is sufficient, cell fusion is performed subsequently, followed by standard screening, cloning, and isolation protocols. After the isolation and expansion of clones, ascites fluids are collected and monoclonal antibodies purified therefrom. (See, e.g, Ausubel, et al. (eds.), *Current Protocols in Molecular Biology*, John Wiley & Sons, NY (1994), Chp. 11.)

Immunoaffinity chromatography of the immunogen may also be performed according to the method of Greve and Gottlieb, *J. Cell. Biochem.* 18: 221–229 (1982), or McMaster and Williams, *Immunol. Rev.* 47: 117–137 (1979), the disclosures of which are incorporated by reference herein. Also, while monoclonal anti-idiotype antibodies are particularly preferred, polyclonal anti-idiotype antibodies may be prepared according to the methods disclosed in Section E and Example 3 herein.

Immunoscreening procedures used to identify useful anti-idiotype antibodies are those described in Example 2. Alternatively, the methods of Laemmli and Favre, *J. Mol. Biol.* 80: 576–600 (1973) or Greve and Gottlieb, Id. (1982) (the disclosures of which are incorporated by reference herein) may be used. Purification of anti-idiotype antibodies is performed as described above and in Example 2.

Example 5

Cell Attachment Assays

In the cell attachment assays, a single cell suspension was allowed to settle for a fixed period of time onto a solid support that has been coated with the different CT-derived proteins to be tested for cell attachment (Friedlander, et al., *J. Cell Biol.* 107: 2329–2340 (1988)). After removing the unbound and loosely bound cells by washing, the attachment and morphology of those cells remaining on the dish were analyzed.

A. Solid Support Preparation

Solid supports for the cell attachment assays were prepared by binding the fusion proteins to a solid support, such as a polystyrene dish. The amount of bound fusion protein was quantitated in order to determine the relationship between the number of cells attached to the fusion protein with the number of picomoles of fusion protein bound to the solid support.

1. Quantitation of Bound Fusion Proteins

To quantitate the amount of fusion protein bound to the solid support, an aliquot of each of the fusion proteins was radiolabeled, admixed with unlabeled fusion protein, and allowed to bind to the solid support. The unbound fusion protein was removed by washing and the amount of bound fusion protein quantitated in order to determine the amount of fusion protein bound to the solid support.

The fusion proteins were radiolabeled with $^{125}$I using enzymatic iodination with a mixture of lactoperoxidase and glucose oxidase immobilized onto hydrophilic microspheres (Enzymobeads; Bio-Rad Laboratories, Richmond, Calif.). Approximately 0.2 milligrams (mg) of fusion proteins were iodinated at a time. To a solution of 10 mg/ml of fusion protein (500 μl) in 0.2 M phosphate buffer, pH 7.5, 350 μl of Enzymobead reagent was added, followed by 125 μl of 2% glucose and 2 to 3 milliCuries (mCi) of Na[$^{125}$I] (New England Nuclear, Boston, Mass.) (100 mCi/ml). The iodination was allowed to proceed at room temperature for 40 minutes and the reaction was terminated by passing the mixture through a gel filtration column, PH-19 Sephadex G-25M (Pharmacia). The iodinated protein was eluted with 6 ml of PBS. The first 2 ml of PBS were discarded and the next 4 ml were collected in 1 ml aliquots. The samples were dialyzed against PBS at 4° C. for 8 hours, with three changes of four liters each. The iodinated proteins were stored at 4° C. and the protein concentration was determined by the modified Lowry method (Lowry, et al., *J. Biol. Chem.* 193: 265–275 (1951) to determine the specific activity. The purity of each preparation was assessed by SDS-PAGE using 10–12% gels (Laemmli, *Nature (Lond.)* 1 227: 680–685 (1970)) under reducing conditions, followed by autoradiography.

The ability of cells to attach to different proteins depends strongly on the amount of protein bound to the solid support. To ensure that differences in cell attachment to fusion proteins were not due to differences in amounts of protein adsorbed to the solid support, the amount of protein bound per spot was determined for each fusion protein and cell attachment was assessed per mole of protein. 200 μg of fusion proteins were iodinated as described above.

Fusion proteins admixed with trace amounts of labeled protein were spotted on and adsorbed to polystyrene dishes and nonspecific binding sites blocked as described above. The dishes were cut into small sections and the amount of radioactivity associated with the spot determined. The amount of fusion protein bound to the polystyrene dish was as follows: CTfn3 96 picomole (pmol)/mm$^2$; CTfn4 123 pmol/mm$^2$; CTfn5 116 pmol/mm$^2$; and CTfn6 100 pmol/mm$^2$. Quantification of the amount of fusion protein bound demonstrated that the amount of bound fusion protein was directly proportional to the concentration of fusion protein in the coating mixture in each case.

2. Preparation of Solid Support with Bound Fusion Proteins

Solid supports, consisting of a circular array of CT or CT:GST fusion proteins bound to a dish, were prepared as follows for the cell attachment assay.

For the initial study, non tissue-culture treated polystyrene plates (Falcon 1008) were spotted with 2 μl of a 0.5 to 1.5 μM solution of CT in PBS for 30 minutes to coat a specific area on the dish with CT. CT was isolated from chicken brain or from fibroblast culture supernatant as described in Crossin, *PNAS* 88: 11403–11407 (1991) and Hoffman et al., *J. Cell Biol.* 106: 519–532 (1988). CT was placed in a circular array near the center of the dish and incubated at 37° C. for 30 minutes. After CT had adsorbed to the dish, the central portion of the dish was washed once with 250 μl of 20% (w/v) BSA in PBS. Non-specific binding sites on the dish were then blocked with 250 μl of 20% (w/v) BSA in PBS by incubation for 2 to 3 hours at room temperature.

For the subsequent study with the CT:GST fusion proteins, non tissue-culture treated polystyrene plates (Falcon 1008) were spotted with 2 μl of a 0.5 to 1.5 μM solution of CT:GST fusion protein in PBS as prepared in Example 5.A.2 or GST in PBS for 30 minutes to coat a specific area on the dish with CT:GST fusion protein or GST. The proteins to be tested were placed in a circular array near the center of the dish and incubated at 37° C. for 30 minutes. After the proteins adsorbed to the dish, the central portion of the dish was washed once with 250 μl of 20% (w/v) BSA in PBS. Non-specific binding sites on the dish were then blocked with 250 μl of 20% (w/v) BSA in PBS by incubation for 2 to 3 hours at room temperature.

3. Fibrobtast Cell Preparation

The chicken fibroblast cell line SL29 (ATCC CRL 1590) was grown to confluence in Dulbecco's Minimum Essential Medium (DMEM; Gibco-BRL, Gaithersburg, Mass.) with 10% (v/v) fetal calf serum (FCS; Gibco-BRL) with penicillin and streptomycin. The cells were passaged the night prior to the assay and seeded at a density of 1:2. Cells were harvested in calcium, magnesium-free Hank's balanced salt solution (CMF-HBSS, Gibco-BRL) with 20 mM Hepes buffer and 5 mM EDTA. Harvested cells were washed in attachment buffer (CMF-HBSS with 10 mM Hepes, 1 mM CaCl$_2$, 1 mM MgCl$_2$, 0.1 mM MnCl$_2$, and 2% (w/v) bovine serum albumin (BSA)) three times. The number of cells was quantitated by counting the cells in a hemocytometer. The cells were resuspended in attachment buffer to a density of 6×10$^5$ cells/ml.

4. Dorsal Root Ganolia Neuronal Cell Preparation

Dorsal root ganglia (DRG) cells or forebrain neurons were prepared for the cell attachment assays as follows. DRG from day 6 chicken embryos or forebrains from day 7 chicken embryos were dissected into HBSS. The tissue was pelleted by centrifugation and resuspended in CMF-HBSS and incubated at 37° C. for 10 minutes. The tissue was pelleted again and resuspended in CMF-HBSS containing 0.08% trypsin and allowed to trypsinize for 20 minutes at 37° C. An equal volume of DMEM/F12, 10% FCS, 20 ng/ml nerve growth factor (NGF) (for DRG cells only), 10 μg/ml gentamycin (10% medium) was added, and the tissue was pelleted and resuspended in 2 ml of the 10% medium. The cells were triturated with a fire-polished Pasteur pipette for 15 strokes, and the cells were washed and resuspended in 10 ml of 10% medium. DRG cells were plated in a 10 cm tissue culture dish and incubated for 1 hour at 37° C. in 5% CO$_2$, to allow for attachment of contaminating fibroblasts.

After replating, the cells were harvested, pelleted and washed three times in DMEM/F12, 1% fetal calf serum (FCS), 20 ng/ml NGF (for DRG cells only), 10 μg/ml gentamycin (1% medium), and the number of cells determined using a hemocytometer. The DRG were resuspended to a density of 6×10$^5$ cells/ml in attachment buffer. The neurons were resuspended to a density of 2×10$^4$ cells/ml in 1% medium and added to substrates and placed at 37° C., 5% CO$_2$ for 15 hours.

After the growth period, the dishes were gently rinsed with PBS to remove unbound cells, fixed with 1% glutaraldehyde, and viewed by phase contrast microscopy. Ten to forty cells were analyzed for each substrate. Cells were judged as neurite-bearing if the length of the processes was greater than one cell diameter. All cells with neurites were photographed with a 20× objective and total neurite length per neurite-bearing cell was derived from the photographic prints. Percentage of neuronal sprouting was calculated from at least six experiments. Neurite length was calculated from at least three experiments.

B. Cell Attachment Assay

1. Cell Attachment Assay to CT

The effects of intact CT on cell attachment in vitro have been characterized. A number of cell types can attach to CT-coated solid supports although the cellular morphology remains rounded. Attachment activities of CT have been mapped to the proximal fibronectin type III repeats and the fibrinogen domain (Prieto, et al., *J. Cell Biol.* 119: 663–678 (1992)).

Chicken fibroblasts, DRG, and solid supports (dishes) coated with CT for use in the cell attachment assays were prepared as described in Examples 5.A.2–4, respectively. The chicken fibroblasts and DRG at a density of $6 \times 10^5$ cells/ml were added to the prepared dishes and incubated at 37° C. in 5% $CO_2$ for 1 hour. The dishes were then washed three times in PBS with gentle swirling to remove unattached cells, fixed in 1% glutaraldehyde in PBS, and viewed by phase contrast microscopy. The number of bound cells was determined using a 10x objective with an eyepiece reticle. The number of cells was determined in four fields for each fusion protein dot as the number of cells bound per 384 $\mu M^2$. CT was tested in triplicate. The number of cells bound for CT was expressed as the average of the twelve measurements±standard deviation (SEM).

CT, coated at a concentration of 20 $\mu$g/ml, was used as a solid support for SL29 fibroblast attachment. The fibroblasts readily attached to the CT solid support as shown in FIG. 2. To determine which domains of CT mediated the individual cell attachment activities demonstrated above with intact CT, fusion proteins spanning the entire length of the molecule were generated and tested for cell attachment activity. Fragments of CT were generated using the pGEX fusion protein system, as described in Example 1. The cell attachment assay was performed essentially as described above for the cell attachment assay to intact CT.

Results of the cell attachment assays using fragments of CT indicate that when the CT:GST fusion proteins CTfn3, CTfn6, and CTfg were coated on plastic at 0.75 $\mu$M concentration, robust SL29 cell attachment was supported. In contrast, GST and the CT:GST fusion proteins CTegf, CTfn1–2, CTfn4, CTfn5, and CTfn7–8, when coated on plastic at three times the concentration used for the other fragments that demonstrate binding activity, did not display significant attachment activity.

This lack of significant attachment activity is defined as less than 1 cell per field. While robust cell attachment was supported by CTfn3, CTfn6, and CTfg, only CTfn3 also exhibited cell spreading.

The next step in defining the nature of the fibroblast cell interaction with CT was to examine the receptors mediating the attachment of these cells to CT by a cell attachment inhibition assay.

C. Cell Attachment Inhibition Assay

Chicken CT contains a single Arg-Gly-Asp (RGD) tripeptide, located in the third fibronectin type III repeat, which is present in both CTfn1 and CTfn2. RGD tripeptides have well-characterized binding activity to the integrin family of cell surface receptors (Hynes, *Cell* 48: 549–554 (1987)). RGD-dependent binding of cells to CT has previously been reported (Bourdon, et al., *J. Cell Biol.* 108:1149–1155 (1989) and Friedlander, et al., *J. Cell Biol.* 107: 2329–2340 (1988)) and further studies reported that CT binds to two members of the integrin family, $\alpha\beta$, (Mendler, et al., *J. Cell Biol.* 115: 137 (1992)) and $\alpha_2\beta_3$ (Joshi, et al., *J. Cell Biol.* 115: 134 (1992) and Mendler, et al., *J. Cell Biol.* 115: 137 (1992)) and that cell attachment can be inhibited by peptides containing the RGD sequence. It should be noted that the RGD sequence in CT is not conserved among species. It is absent from the mouse (Weller, et al., *J. Cell Biol.* 112: 355–362 (1991)), and newt (Onda et al., *Dev. Biol.* 148:219–232 (1991)) sequences, but is present in the human (Gutcher et al., *PNAS* 86: 1588–1592 (1989)) and chicken (Jones et al., *PNAS* 86: 1905–1909 (1989) and Spring et al., *Cell* 59: 325–334 (1989)) sequences.

The synthetic peptide Arg-Gly-Asp-Ser (RGDS) (SEQ ID NO 25) mimics the cell attachment signal of fibronectin and inhibits attachment of cells to fibronectin (Pierschabacher, et al., *Nature* 309: 30–33 (1984)) but not cell attachment to collagen (Hayman et al., *J. Cell Biol.* 100: 1948–1954 (1985)). Further, the peptide Gly-Arg-Gly-Asp-Thr-Pro (GRGDTP) (SEQ ID NO 12) has been shown to be an active inhibitor of cell attachment to type I collagen while the peptide Gly-Arg-Gly-Asp-Ser-Pro (GRGDSP) (SEQ ID NO 11) is far less effective inhibitor of cell attachment (Dedhar, et al., *J. Cell Biol.* 104: 585–593 (1987)).

Recently, the third fibronectin type III repeat (CTfn3) has been shown to be a ligand for $\alpha v\beta 3$, $\alpha_v\beta_6$, (Prieto, et al., *PNAS* 90: 10154–10158 (1993)) and $\alpha 9\beta 1$ integrins. It was also shown that CTfn3 can mediate RGD-dependent cell attachment via the cellular integrins $\alpha_v\beta_3$ and $\alpha_v\beta_6$. Binding of intact CT to a cellular $\beta_1$ integrin has also been demonstrated; however, the CT binding site responsible for this interaction had not been determined.

In order to determine the nature of the receptors mediating attachment of the fibroblasts to CT, specific inhibitors of attachment, including RGD-containing peptides of differing specificities, were added to the cells before plating on CT.

In the cell attachment inhibition assay, a single cell suspension was incubated with a potential inhibitor and then allowed to settle for a fixed period of time onto a solid support that has been coated with the different proteins to be tested (Friedlander, et al., *J. Cell Biol.* 107: 2329–2340 (1988)). After removing the unbound and loosely bound cells by washing, the attachment and morphology of those cells remaining on the dish were analyzed.

In the cell attachment inhibition assays, cells were incubated with soluble RGD peptides and/or a monoclonal antibody prior to incubation with solid support.

The inhibitors tested were the RGD-containing soluble peptides, GRGDSP and GRGDTP and the mAb JG22 (Developmental Studies Hybridoma Bank at Department of Pharmacology and Molecular Sciences, Johns Hopkins University School of Medicine, Baltimore, Md.). JG22 is a mouse hybridoma which binds to many types of chicken cells, including fibroblasts and muscle, and is specific to chicken (Greve, et al., *J. Cell. Biochem.* 18: 221–229 (1982)). JG22 is known to perturb cell attachment to extracellular matrix proteins and disrupts the function of the $\beta_1$ integrin.

The cell attachment inhibition assay was performed essentially as described for the cell attachment assay in Example 5.B., but with the following modifications.

The solid support and cells were prepared as described in Example 5.B. Again, the initial assay was performed using only intact CT for the preparation of the solid support. The inhibitors tested, GRGDSP, GRGDTP, and the mAb JG22, were admixed with separate aliquots of the chicken fibroblast SL29 and DRG cells prior to addition to the solid support containing intact CT. The RGD-containing peptides were added at a final concentration of 1 mg/ml. The mAb JG22 was added at a final concentration of 50 $\mu$g/ml. A combination of each of the RGD-containing peptides and mAb JG22 were also incubated with the fibroblast and DRG cells. The cells and potential inhibitors were incubated for 10 minutes at room temperature and then added to the solid support. Fibroblast and DRG cells without inhibitors were also added to the solid support.

After incubation at 37° C. in 5% $CO_2$ for 1 hour, the solid supports were washed three times in PBS with gentle swirling to remove unattached cells. The cells attached to the solid support were fixed in 1% (v/v) glutaraldehyde in PBS and viewed by phase contrast microscopy. The attached cells were counted using a 10× objective and with an eyepiece reticle. Cells were counted in four fields per adsorbed protein spot. Each protein was tested in three separate spots. The number of cells bound was expressed as the average of the twelve measurements±the standard deviation.

Results of the cell attachment inhibition assay to determine the effect of RGD peptides and a $\beta_1$ mAb on the attachment of chicken fibroblasts and DRG cells to intact CT indicate that both of the soluble RGD peptides tested, GRGDSP and GRGDTP, could only partially inhibit attachment to CT by 73% and 70%, respectively (FIG. 2). JG22, a function-blocking monoclonal antibody against the $\beta_1$ integrin, caused a 22% decrease in cell attachment. Cell attachment activity was completely abolished, however, when either RGD peptide and JG22 were added in combination. These results are consistent with previous studies showing that two integrin binding sites exist on CT (Prieto et al., PNAS 90: 10154–10158 (1993)).

A further analysis of attachment of SL29 fibroblasts to intact CT/TN was conducted in the presence and absence of soluble GRGDTP peptide or the mAb JG22 to localize the site in CT/TN responsible for interaction with $\beta_1$ integrins. SL29 fibroblasts bound well to CT/TN-coated substrates; this attachment was inhibited 33% in the presence of 1 mg/ml GRGDTP peptide. Although antibody JG22 alone had little effect on fibroblast attachment to CT/TN, the combination of this antibody with GRGDTP peptide resulted in complete inhibition of attachment to CT/TN. This suggests that intact CT/TN has at least two discrete integrin binding activities, one which is RGD-dependent but not A integrin-mediated and one in which $\beta_1$ integrin is involved but is not RGD-dependent.

In studies to identify the specific regions within CT/TN that mediated the RGD-dependent and $\beta_1$ integrin-dependent responses to CT/TN, each of the fusion proteins spanning the entire length of the CT/TN protein was coated onto plastic dishes and cell attachment was quantitated in the presence of RGD-containing peptides and anti-$\beta_1$ integrin antibodies as inhibitors. Cells readily attached to CTfn3, CTfn5–6, and CTfg, but not to any of the other fusion proteins, including the differentially spliced region. A fibroblast attachment activity previously localized to the fourth through sixth FN type III repeats (Prieto et al., Id. (1993)) was more precisely localized within a fusion protein spanning the fifth and sixth FN type III repeats. The amount of protein bound to the substrate was measured as described previously herein so that equimolar amounts of protein were bound to the substrate for these comparative assays. When soluble GRGDTP peptide was added before plating the cells, attachment to CTfn3 was completely inhibited, while attachment to CTfn5–6 and CTfg was unaffected. Monoclonal antibody JG22 inhibited binding to CTfn5–6 by 77% but had no effect on attachment to CTfn3 and only a slight effect on attachment to CTfg. When the fifth and sixth FN type III repeats were generated as separate fusion proteins, the fibroblast attachment activity was localized to the sixth repeat and no cell attachment was observed to the fifth repeat (not shown). The sixth repeat was therefore used in subsequent studies.

The cell attachment inhibition assay was repeated as described above but using all of the CT:GST fusion proteins in place of intact CT for the preparation of the solid support as described in Example 1.

When chicken fibroblast and DRG cell attachment to surfaces coated with each of the CT:GST fusion proteins at the same molar concentration was compared, differences were observed among the different inhibitors. While soluble GRGDSP peptide completely inhibited attachment to CTfn3, attachment to CTfn6 was only partially inhibited and attachment to CTfg was unaffected. In contrast, GRGDTP peptide selectively inhibited attachment to CTfn3 but was not effective at inhibiting cell attachment to CTfn6. GRGDTP peptide has been shown previously to inhibit binding to collagen I while GRGDSP had no effect (Dedhar et al., J. Cell Biol. 104: 585–593 (1987)). The monoclonal antibody JG22 only affected cell attachment to Ctfn6.

These results suggest that two separate integrin receptors mediate cell attachment to both CTfn3 and CTfn6. Cell attachment to CTfn3 is selectively inhibited by an RGD-containing peptide variant which had previously been shown to have altered specificity. In addition, one site for $\beta_1$ integrin binding in CT is localized to the sixth fibronectin type III repeat.

While neither the GRGDTP peptide nor the JG22 MAb could completely inhibit cell attachment to intact CT, a combination of the two abolished all attachment activity, suggesting that the receptors that bind CTfn3 and CTfn6 can also bind the intact molecule (FIG. 2).

To determine whether the same fragments that supported fibroblast attachment also support attachment of neurons, two primary neuronal cell types were tested for attachment to CT/TN and CT/TN fragments in the presence and absence of mAb JG22. Since CT/TN has previously been shown to increase neurite elongation of neurons from both the PNS and CNS, we tested the attachment of neurons from chick dorsal root ganglia and chick forebrain as examples of each neuronal type. As was observed for fibroblasts, only three fragments—CTfn3, CTfn6, and CTfg—were able to support DRG neuron attachment (not shown). Whereas the three fragments appeared to be equivalent for fibroblast attachment, fewer DRG cells attached to CTfn3 compared to CTfn6 and CTfg. When DRG cells were preincubated with JG22, attachment to CTfn6 was inhibited by 38%. A decrease in attachment to CTfg (19%) was also observed but attachment to CTfn3 was completely unaffected by this antibody. Attachment to intact CT/TN was inhibited 40% in the presence of JG22. Thus, it appears that DRG neurons bind to the same three sites in CT/TN as do fibroblasts.

D. DRG Neurite Outgrowth on CTfn3, CTfn6, and CTfg

In order to assess the effect to the cell binding regions of CT/TN on the outgrowth of neurites from PNS neurons, DRG cells were cultured for 40 hours on popylysine, CTfn3, CTfn6, CTfg, and CTfn3-CTfn6 mixed substrates. The cultures were then fixed and the cell and neurite morphology was analyzed by phase contrast microscopy. The cells were plated on plastic substrates coated with the same concentrations of CTITN and fusion proteins used in the attachment assay.

All of the cell binding regions of CT/TN supported some level of neurite outgrowth from these cells, but their effects were not identical (data not shown). DRG cells plated on CTfn3 showed long fasciculated processes and cell bodies that tended to aggregate, compared with cells plated on polylysine, which showed a basal level of outgrowth as did cells plated on CTfg. Occasionally, an isolated neuron with long processes was found on CTfn3, but neurons on this substrate were generally clumped together. In contrast, CTfn6 supported the outgrowth of moderately long neurites from cell bodies that were more isolated. When DRG cells were plated on a mixed substrate of CTfn3 and CTfn6, however, a much more elaborate network of neurites was formed. On this substrate, cell bodies remained even more isolated when-compared to neurons plated on either CTfn3 or CTfn6. On CTfn3–CTfn6 mixed substrates, or substrates plated with the Ctfn3/6 construct, the neurites appeared to be much longer and less fasciculated than neurites on CTfn3 or CTfn6 alone.

This extensive neurite outgrowth after 40 hours made quantitation of the percentage of neurite-bearing cells and neurite length difficult. To analyze quantitatively the effect of CT/TN fusion proteins on DRG neurite outgrowth, DRG cells were therefore plated at low density on CT/TN or CT/TN fragments and analyzed after 15 hours in culture for the percentage of cells that sprouted neurites greater than one cell diameter and for the everage neurite length per neuron. These conditions enhanced the number of isolated cells and discouraged the cell-cell interactions and fasciculation that occurred in the long-term cultures. On GST control substrates, a few cells per field remained bound after fixation in long-term culture, although no cells attached to this protein in the short-term attachment assays (not shown). No neurite-bearing cells were ever found on GST substrates.

DRG cells plated on CT/TN fragments CTegf, CTfn1–2, CTfn4, CTfn5, CTspl, and CTfn7–8 also did not extend neurites and were indistinguishable from cells plated on the GST control (data not shown). In contrast, fragments CTfn3, CTfn6, and CTfg showed distinct effects on neurite promotion. As illustrated in Table 4, the percentage of neurite-bearing CRG cells plated on CTfn3 and CTfg was comparable to the number on polylysine-coated substrates. In contrast, on CTfn6-coated substrates the number of neurite bearing cells was 82% greater than on the polylysine control substrate. When neurons were plated on an equimolar mixture of CTfn3 and CTfn6, almost 50% of the cells grew long neurites, a 188% increase over polylysine. DRG cells plated on intact CT/TN (see Table 4) also showed a high level of cells that sprouted neurites (30%), which was comparable to that on CTfn6-coated substrates.

TABLE 4

Quantitation of Neurite Outgrowth on CT/TN and CT/TN Fragments

| Cell Type | Substrate | % Sprouting | Neurite Length |
|---|---|---|---|
| DRG | PLL | 17 ± 2 | 91 ± 38 |
| " | CTfn3 | 12 ± 2 | 260 ± 141** |
| " | CTfn6 | 31 ± 2*** | 153 ± 124 |
| " | CTfg | 8 ± 3 | 82 ± 23 |
| " | CTfn3 + 6 | 49 ± 4*** | 453 ± 160*** |
| " | CT/TN | 30 ± 3*** | 332 ± 177*** |
| FB | PLL | 3.2 ± 0.6 | ND |
| " | CTfn3 | 0 | " |
| " | CTfn6 | 8.7 ± 1.9* | " |
| " | CTfg | 2.2 ± 0.5 | " |
| " | CTfn3 + 6 | 4.5 ± 0.4* | " |
| " | CT/TN | 0 | " |

Comparison of neurite outgrowth of ERG and forebrain neurons on CT/TN and CT/TN fragments. Neurite length is given in microns. Asterisks denote activity significantly greater than polylysine control: * = $p < 0.001$;  = $p < 0.005$; * = $p < 0.05$.

The lengths of neurites from DRG cells cultured on CTfn6 and CTfg were not statistically different from those on the polylysine control. Neurites on CTfn3 were significantly longer than those on polylysine, even though few cells sprouted neurites on either of these substrates. As observed in the longer-term cultures, when CTfn3 and CTfn6 were combined on the same substrate, an increase in neurite length was observed that was greater than that observed on either CTfn3 or CTfn6 substrates alone. The average neurite length on CTfn3 and CTfn6 mixed substrates was 1.7 times longer than neurites on CTfn3 alone and almost 5 times longer than neurites on the polylysine control.

Representative morphologies of DRG neurons demonstrate the dramatic differences in neurite length between DRG neurons on polylysine or CTfn6 substrates compared with neurons on CTfn3 and CTfn6 mixed substrates (not shown). Surprisingly, the anti-$\beta_1$ integrin mAb JG22 or the peptide GRGDTP both inhibited neurite outgrowth on CTfn3 or CTfn6 substrates, but not on polylysine-coated substrates (data not shown). This result contrasts with the ability of these agents to inhibit differentially the short-term attachment of DRG neurons and fibroblasts on CTfn3 and CTfn6. Nevertheless, these experiments clearly show that CTfn3 and CTfn6 have different neurite promoting activities; one enhances neuronal sprouting and the other enhances neurite elongation. When combined (either via mixing on substrates or combined into a single construct, e.g., CTfn3/6), they stimulate a significant increase both in the percentage of neurite-bearing cells and in neurite elongation.

E. CNS Neurote Outgrowth on CT/TN. CTfn3 and CTfn6

To investigate whether CNS neurons could also extend neurites on CT/TN and CT/TN fragments, neurons from chick forebrain were plated at low density on CT/TN, CT/TN fragments and polylysine, and analyzed for neurite outgrowth after a 7 hour growth period (a time period found to be optimal for stable neurite outgrowth from these cells). Quantitation of the percentage of forebrain cells with neurites in respnose to CT/TN and CT/TN fragments is given in Table 4 above. The lengths of neurites on substrates that supported sprouting were essentially the same for the forebrain neurons and were therefore not quantitated further. Substrates coated with CTfn6 or a mixture of CTfn3 and CTfn6 supported a significant increase in the number of cells sprouting neurites over the polylysine control. The percentage of cells with neurites on CTfg was not significantly different from that of the polylysine control. CTfn3 did not support forebrain cell attachment and therefore also had no effect on neurite outgrowth. Intact CT/TN supported a low level of attachment of forebrain cells after the seven hour growth period, but did not support sprouting of neurites. We concluded that CTfn6 promotes attachment and neurite outgrowth from forebrain neurons, but that unlike DRG neurons, neurite extension from forebrain neurons shows no synergistic effect on mixtures of CTfn3 and CTfn6.

Example 6

Neurite Outgrowth Assays

A. Descrintion of Adhesion Proteins

The proteins used in the neurite outgrowth assays are the same as those used in the cell attachment assays. Even those CT:GST fusion proteins which did not exhibit significant cell attachment activity were examined in the neurite outgrowth assays. In addition, poly-L-lysine was adsorbed to the solid support. Poly-L-lysine (PLL) has been shown to promote cell attachment of various cell types and is suitable for use in short-term assays, such as those described herein, to determine the basal level of neurite outgrowth. Any cells adhering to the solid support were examined for sprouting and neurite length as defined herein.

B. Preparation of the Proteins Adsorbed to the Solid Support

Proteins used in the neurite outgrowth assays were prepared as described in Example 5.A.2. An additional adhesion molecule, poly-L-lysine, which has been shown to promote cell attachment of various types of cells was also prepared as described in Example 5.A.2. and used to coat the solid support.

C. Two-Dimensional Neurite Outgrowth Assays

Dorsal root ganglia (DRG) from day 6 chicken embryos were prepared as described in Example 5.A.4. For the neurite outgrowth assays, the DRG were resuspended at a density of $2 \times 10^4$ cells/ml in 1% medium, added to solid support, and placed at 37° C. in 5% $CO_2$ for 15 hours. After the attachment and growth period, the dishes were gently rinsed with PBS to remove unbound cells, fixed with 1% (v/v) glutaraldehyde, and viewed by phase contrast microscopy. Ten to thirty cells were analyzed for each adsorbed protein spot. Cells were judged as neurite-bearing if the length of the processes were greater than one cell diameter. All cells with neurites were photographed with a 40× objective and the total neurite length per neurite-bearing cell was derived from the prints. The percent of cells that were sprouting and the average neurite length was derived from six and three independent experiments, respectively. Results are shown in Table 5 and illustrated in FIGS. 3A and 3B, respectively.

TABLE 5

| Adhesion Molecule poly-L-lysine | Percent Sprouting | Neurite Length (in microns) |
|---|---|---|
|  | 17 ± 2 | 91 ± 38 |
| CTfn3 | 12 ± 2 | 260 ± 141** |
| CTfn6 | 31 ± 2*** | 154 ± 124 |
| CTfg | 8 ± 3 | 83 ± 23 |
| CTfn3 + CTfn6 | 49 ± 4*** | 453 ± 160*** |
| CT | 30 ± 3 | 332 ± 177*** |

The asterisks denote activity, which is significantly greater than poly-L-lysine, wherein: signifies that p = 0.005 and *signifies that p = 0.001.

About 50% of the DRG plated on CT showed neurites greater than one cell diameter. Approximately 10–15 cells per dot area remained bound after fixation of cells attached to GST adsorbed to the solid support. This background attachment of cells to GST is presumably due to the low levels of serum present in the plating medium. Despite the low level attachment of DRG cells to the GST-coated solid support, neurite-bearing cells were not found on the GST-coated solid support. DRG cells plated on CT:GST fusion proteins CTegf, CTfn1–2, CTfn4, CTfn5, CTspl, and CTfn7–8 were all indistinguishable from the GST control. In contrast, CT:GST fusion proteins CTfn3, CTfn6 and CTfg did show neurite promoting activity.

As shown in FIG. 3A and Table 5, DRG cells plated on CTfn3 and CTfg gave a percentage of neurite-bearing cells comparable to the poly-L-lysine-coated solid support. In contrast, neurons plated on CTfn6-coated solid support showed a 57% increase in the number of neurite-bearing cells over poly-L-lysine. When neurons were plated on an equimolar mixture of CTfn3 and CTfn6, almost 50% of the cells grew neurites. Although CTfn3 did not promote additional neurite sprouting above that of poly-L-lysine, the neurites that did form were 3 times longer than those of poly-L-lysine. Neurite lengths on CTfn6 and CTfg were statistically indistinguishable from those of poly-L-lysine. When CTfn3 and CTfn6 were combined on the same spot on the solid support, a dramatic increase in neurite length was observed. The average neurite length on CTfn3 +CTfn6 was 1.7 times longer than that of neurites on CTfn3 alone and almost 5 times longer that neurites on the poly-L-lysine. Thus, both CTfn3 and CTfn6 have individual neurite promoting activities, and when combined, result in a synergistic increase in neurite elongation.

Herein described is a fusion protein which spans the sixth fibronectin repeat (CTfn6) which supports both fibroblast and neuronal cell attachment. This attachment is mediated by the bind of CTfn6 to a $\beta_1$ integrin. All of the CT fragments prepared in this invention were tested for their ability to support neurite outgrowth. The CTfn6-coated solid support promoted an increase in neurite outgrowth over poly-L-lysine as demonstrated by both the percentage of neurite-bearing cells and in the total neurite length per cell. While the percentage of neurite-bearing cells on CTfn3-coated solid supports was the same as on poly-L-lysine, total neurite length per neurite-bearing cell was longer on CTfn3-coated solid support than on poly-L-lysine or CTfn6-coated solid supports (Table 5 and FIGS. 3A and 3B). None of the other fragments demonstrated any significant neurite-promoting activity in this assay.

When neurons were plated on a solid support coated with a mixture of CTfn3 and CTfn6, a dramatic increase in both percent sprouting and neurite length was observed, which more closely resembled the activity of intact CT. These results suggest that different sites in CT mediate specific cell binding activities through distinct cell surface receptors. In combination, these sites can generate enhanced cellular responses, such as the promotion of neurite outgrowth, which may account for the activity of the intact molecule.

Example 7

Inhibition of Neurite Outgrowth by Fusion Proteins and Monoclonal Antibodies

Additional confirmation of the ability of CTfn3 and CTfn6 to promote cell attachment and neurite outgrowth, as defined herein, can be determined by the use of mAbs which immunoreact with CTfn3 and CTfn6 and block these functions. Examples of such mAbs have been described in Section E and Example 2. Inhibition of cell attachment and neurite outgrowth in the presence of mAbs that immunoreact with CTfn3 and CTfn6 can also be demonstrated in the presence of soluble CTfn3 and CTfn6.

A. Competition Binding Assay Using Monoclonal Antibodies with CTfn3 and CTfn6 in Solid Phase A method which can be used to confirm the ability of CTfn3 and CTfn6 to promote cell attachment and neurite outgrowth is one which either or both CTfn3 and CTfn6 are bound in the solid phase. The regions of these fragments that promote attachment of cells and their subsequent neurite outgrowth are then immunoreacted with mAbs. The formation of an immunoreactive complex between CTfn3 and CTfn6 and their respective mAbs inhibits cell attachment and neurite outgrowth.

1. Purification of Monoclonal Antibody

The mAbs which immunoreact with CTfn3 and CTfn6 have been described in Example 2. Such mAbs for use in the herein described inhibition assays can be purified by various methods including those described in Example 2.

2. Inhibition of Neurite Outgrowth by Fusion Proteins

The method of demonstrating inhibition of cell attachment to CTfn3 and CTfn6 in the presence of soluble CTfn3 and CTfn6 is similar to that described in Example 5.C. for inhibition cell attachment with soluble RGD peptides. The inhibition of neurite outgrowth is determined in the same manner as the neurite outgrowth assays described in Example 6.C., however, the assay is performed in the presence of the potential inhibitors of neurite outgrowth, soluble CTfn3 and CTfn6.

The solid supports are prepared by immobilizing CT:GST fusion proteins to polystyrene dishes. Single cell suspensions of neuronal cells are prepared as described in Example 5.A.4. and incubated with either soluble CTfn3 or CTfn6. If the soluble CTfn3 has interacted with the site on the neuronal cell which mediates attachment of the cell to the immobilized CTfn3, the presence of the CTfn3 will block the cell attachment site and thereby inhibit cell attachment to the immobilized CTfn3. The inhibition assay may also be performed with soluble CTfn6 in the same manner to confirm that the soluble CTfn6 has blocked the cell attachment site on the neuronal cell and inhibits neuronal cell attachment to immobilized CTfn6.

To demonstrate inhibition of cell attachment to immobilized CT:GST fusion proteins in the presence of the soluble CT:GST fusion protein, solid supports and cells are prepared as described in Examples 5.A.2. and 5.A.B., respectively. Prior to incubation with proteins or adhesion molecules adhered to a solid support, neuronal cells are incubated a concentration of soluble CTfn3 which is sufficient to saturate all of the CTfn3 binding sites on the neuronal cell. A preferred concentration of soluble CTfn3 is from about 1 to 10 mg/ml. The cells are incubated in the presence of soluble CTfn3 for a period of time which is sufficient for the binding reaction of the soluble CTfn3 to the binding site on the neuronal cell to occur. A preferred amount of time is from about 10 to 60 minutes. The neuronal cells which have bound to the soluble CTfn3 are then incubated in the presence of a solid support with immobilized CTfn3 for an amount of time which is adequate for cell attachment and neurite outgrowth to occur. A preferred amount of incubated time is from about 15 to 30 hours. After the attachment and growth period, the number of cell attached, the number of cells sprouting, and the length of the neurites is determined as described in Example 6.C. The assay may also be performed with other soluble proteins, such as CTfn6, to determine their affect on cell attachment and subsequent neurite outgrowth.

The effect of soluble CTfn3 and any other soluble protein, such as CTfn6, or adhesion molecule, such as poly-L-lysine, on cell attachment and neurite outgrowth on a solid support can thus be determined using the methods herein described.

3. Inhibition of Neurite Outgrowth by Antibodies

The method of demonstrating inhibition of cell attachment to CTfn3 and CTfn6 in the presence of mAbs which immunoreact with CTfn3 and CTfn6 is similar to that described in Example 5.C. for inhibition of cell attachment with the mAb JG22. The inhibition of neurite outgrowth is determined in the same manner as the neurite outgrowth assays described in Example 6.C., however, the assay is performed in the presence of potential inhibitors of neurite outgrowth.

The solid support is prepared by immobilizing CT:GST fusion proteins to polystyrene dishes. The solid support is then incubated in the presence of the mAbs which immunoreact with the CTfn3 or CTfn6 fusion proteins. The mAb which immunoreacts with CTfn3, as described in Example 2, and the CTfn3 fusion protein immobilized on the dish form an immunoreaction product. Single cell suspensions of neuronal cells are then incubated with the immunoreaction products. If the mAb has immunoreacted with the site on CTfn3 which the cell attaches to, the presence of the mAb will block the cell attachment site and thereby inhibit cell attachment to the immobilized CTfn3. The inhibition assay may also be performed with a mAb which immunoreacts with CTfn6 in the same manner to confirm that the mAb immunoreacts with the site on CTfn6 which mediates cell attachment to CTfn6.

To demonstrate inhibition of cell attachment to immobilized CT:GST fusion proteins in the presence of mAbs which immunoreact with CTfn3 or CTfn6, solid supports and cells are prepared as described in Examples 5.A.2. and 5.A.B., respectively. The solid support is then incubated with a concentration of mAb, from about 50 to 500 $\mu$g/ml, which is sufficient to immunoreact with all of the CTfn3 fusion proteins which form the neuronal cell binding sites. The solid support is incubated in the presence of the mAb for a period of time, from about 10 to 60 minutes, which is sufficient for the immunoreaction reaction of the CTfn3 and mAb is to occur. The solid support which has bound to the mAb is then incubated with a single cell suspension of neuronal cells for about 15 to 30 hours, an amount of time which is adequate for cell attachment and neurite outgrowth to occur. After the attachment and growth period, the number of cell attached, the number of cells sprouting, and the length of the neurites is determined as described in Example 6.C.

The assay may also be performed with mAbs which are immunoreactive with other CT proteins, such as CTfn6, to determine the affect of the mAb on cell attachment and subsequent neurite outgrowth.

The effect of mAbs which immunoreact with CTfn3 and any other soluble protein, such as CTfn6, on cell attachment and neurite outgrowth on solid supports can thus be determined using the methods herein described.

Example 8

Immunoassays to Detect CT

The concentration of CT in a sample can be determined by an immunoassay wherein a mAb which is immunoreactive with CT is in the solid phase.

A. ELISA with Anti-CT in Solid Phase

The mAbs which immunoreact with CTfn3 and CTfn6 as described in Example 2 can also be used to determine the concentration of CT in a given sample by ELISA. For this assay, individual wells of a microtiter plate (Costar 3690) are incubated overnight at 4° C. with 25 $\mu$l of 1 $\mu$g/ml mAb prepared as described in Example 2 in PBS to allow the mAb to adhere to the walls of the microtiter wells. The wells are washed with water and blocked by completely filling the well with 3% (w/v) bovine serum albumin (BSA) in phosphate buffered saline (PBS) and maintaining the plate at 37° C. for one hour. After the blocking solution is shaken out, 50 $\mu$l of the sample containing an unknown concentration of CT is admixed to each well, and the plate is maintained for two hours at 37° C. to allow the formation of immunoreaction products between the immobilized mAb and CT. Following the maintenance period, the wells are washed ten times with PBS-Tween 20 to remove unbound CT and then maintained with a 25 $\mu$l of a 1:500 dilution of a secondary Ab which immunoreacts with CT and incubated again at 37° C. for 2 hours. The second antibody is a polyclonal antibody which has been prepared in goat and forms an immunoreaction product with CT. After the incubation period, the wells are washed ten times with PBS-Tween 20 to remove any unbound Ab and then incubated in with a 1:500 dilution of a secondary rabbit anti-goat IgG conjugated to alkaline phosphatase diluted in PBS and containing 1% BSA. The secondary rabbit anti-goat IgG does not detect the antibody, prepared as described in Example 2, which is adsorbed to the dish in the first step. The wells are maintained at 37° C. for one hour after which the wells are washed ten times with water followed by color development with 50 µl of p-nitrophenyl phosphate (PNPP). Color development is monitored at 405 nm to measure the amount of bound secondary rabbit anti-goat IgG antibody.

B. Immunohistochemistry with Anti-CT

The mAbs of this invention which immunoreact with CTfn3 and CTfn6 can also be used to directly detect expression of CT in tissues by immunohistochemistry. For immunohistochemistry, tissues are generally treated with a suitable fixative, for example paraformaldehyde, to preserve the morphology of the tissue, the tissue is then cryoprotected with sucrose, and frozen. The tissues are thinly sliced while still frozen using a cryostat and placed on microscope slides. Tissue sections are reacted with a mAb which specifically detects the presence of a given antigen, such as CT, and the reaction is visualized by the use of a secondary antibody which is attached to a label, such as alkaline phosphatase. Alternatively, the mAb which immunoreacts with CT can be labeled directly.

CT expression at various developmental stages can be studied by examining animals at different ages. The use of immunohistochemical methods offers the advantage of being able to visualize the cell types within a given tissue which interact with CT and the effect of CT on their attachment and neurite outgrowth. The neuronal cell types can be identified by specific reactivity with mAbs, for example, astrocytes can be identified by immunoreactivity with mAbs to glial fibrillary acidic protein (GFAP). The specifically reacted tissues are then visualized by fluorescent microscopy. When high resolution visualization of the tissues is desired, the tissues can be visualized by electron microscopy by the introduction of variations in the tissue preparation procedure.

Neonatal and adult animals are deeply anesthetized with an overdose of chloral hydrate and perfused with 4% paraformaldehyde. The tissues are then postfixed for 4 hours in the same fixative and cryoprotected with sucrose. Ten-micrometer sections are cut on a cryostat and thawed onto gelatin-coated microscope slides. Sections are then incubated with one either the mAb which immunoreacts with CTfn3 or CTfn6 in PBS overnight which has been diluted 1:200 in PBS. Sections can be double-labeled with mouse anti-GFAP (ICN ImmunoBiologicals) at a dilution of 1:100 in PBS to specifically label astrocytes.

After the incubation, the primary antibody is removed by careful washing with PBS and the sections are incubated with a biotinylated goat anti-mouse IgG at a dilution of 1:100 for 1 hour. The sections are then carefully washed with PBS to remove the secondary antibody and then incubated for 30 minutes in strepavidin conjugated with a 1:100 dilution of Texas red (Amersham). The sections are rinsed and coverslipped in Citifluor (Citifluor Ltd.) and viewed by fluorescent microscopy.

Example 9

Stimulation of Neurite Outgrowth by Anti-Idiotypic Monoclonal Antibodies

Anti-idiotypic antibodies can be used in place of CTfn3 and CTfn6 in the use of this invention because the CTfn3 and CTfn6 anti-idiotypic antibodies mimic the function of CTfn3 and CTfn6, respectively. For example, the anti-idiotypic antibodies can be used for therapeutic applications and offer an advantage over the in vivo use of the CTfn3 and CTfn6 polypeptides due to their long half-life in vivo. Such therapeutic applications include the stimulation of cell attachment and subsequent neurite outgrowth.

A. Competition Binding Assay Using Monoclonal Antibodies in Solid Phase

The applicability of the use of anti-idiotypic mAbs to stimulate cell attachment and neurite outgrowth can be assessed in an in vitro assay in which the anti-idiotypic mAbs are used in the solid phase to promote cell attachment and neurite outgrowth.

1. Purification of Monoclonal Antibody

The anti-idiotypic mAbs are first prepared and purified by the methods described in Example 4.

2. Stimulation of Neurite Outgrowth by Anti-Idiotypic Antibodies

The neurite outgrowth assay can be performed essentially as described in Example 5.C. by substituting the CTfn3 and CTfn6 fusion proteins with the CTfn3 and CTfn6 anti-idiotypic mAbs in the solid phase. A combination of both CTfn3 and CTfn6 anti-idiotypic mAbs may also be advantageous and demonstrate a synergistic effect as seen with a combination of the CTfn3 and CTfn6 fusion protein described in Example 5.B.

Solid supports, comprising a circular array of CTfn3 and CTfn6 anti-idiotypic mAbs bound to a dish either separately or together, are prepared as follows for cell attachment and the stimulation of neurite outgrowth assay. Non tissue-culture treated polystyrene dishes (Falcon 1008) are spotted with 2 μl of a 1 mg/ml solution of mAb in PBS for 30 minutes to coat a specific area on the dish with the mAb. After the mAb has adsorbed to the solid support, the central portion of the dish is washed once with 250 μl of 20% (w/v) BSA in PBS. Non-specific binding sites on the dish are then blocked with 250 μl of 20% (w/v) BSA in PBS by incubation for 2 to 3 hours at room temperature.

Neuronal cells to be assayed for cell attachment and stimulation of neurite outgrowth in the presence of the mAbs are prepared as described in Example 5.A.4. The DRG are resuspended at a density of $2\times10^4$ cells/ml in 1% medium, added to solid supports coated with proteins or adhesion molecules, and placed at 37° C. in 5% $CO_2$ for 15 hours. After the attachment and growth period, the solid supports are gently rinsed with PBS to remove unbound cells, fixed with 1% (v/v) glutaraldehyde, and viewed by phase contrast microscopy. Ten to thirty cells are analyzed for each protein or adhesion molecule spot. Cells are judged as neurite-bearing if the length of the processes are greater than one cell diameter. All cells with neurites are photographed with a 40× objective and the total neurite length per neurite-bearing cell is derived from the prints. Thus, the ability of the CTfn3 and CTfn6 anti-idiotypic mAbs can be assessed by an in vitro assay as described herein.

Example 10

Promotion of Cell Adhesion and Spreading

The ability of CT and CT polypeptides to promote cell adhesion and spreading was determined essentially as follows. To confirm that at least some portion of CT binds to integrins, cell adhesion experiments were performed on surfaces coated with control proteins or with various CT polypeptides or protein.

Cell attachment assays were performed essentially as follows. The chicken fibroblast cell line SL29 was grown to confluence in DMEM with 10% FCS and penicillin/streptomycin. The cells were passaged the night before the assay and seeded at a density of 1:2. Cells were harvested in calcium, magnesium free Hank's balanced salt solution (CMF-HBSS) with 20 mM Hepes buffer and 5 mM EDTA added. The cells were then washed in attachment buffer (CMF-HBSS, 10 mM Hepes, 1 mM CaCl2, 1 mM MgCl2, 0.1 mM MnCl2, 2% BSA) three times, counted in a hemocytometer, resuspended to a density of 6×10$^5$ cells/ml. Dorsal root ganglion (DRG) neurons were prepared for attachment assays as described in Example 5, but were washed and resuspended at a density of 6×10$^5$ cells/ml in attachment buffer. Inhibitors of attachment were added at this time.

To some samples GRGDSP (SEQ ID NO 11) or GRGDTP (SEQ ID NO 12) peptide was added at a concentration of 1 mg/ml. The RGD sequence is capable of mediating cell adhesion via specific members of a family of heterodimeric cell surface receptors, termed integrins (Cheresh and Spiro, *J. Biol. Chem.* 262: 17703–17711 (1987); Hynes, *Cell* 69: 11–25 (1992)). Integrins which recognize the RGD motif include $\alpha_5\beta_1$, $\alpha_{IIb}\beta_3$, and most, if not all, $\alpha_v$ integrins, including $\alpha_v\beta_3$ and $\alpha_v\beta_6$.

Monoclonal antibody JG22 was added at a final concentration of 50 μg/ml where indicated. The cells were incubated with inhibitors for 10 minutes at room temperature, then added to the substrates. After incubation at 37° C., 5% CO$_2$ for 1 hour, the dishes were washed three times in PBS with gentle swirling, fixed in 1% glutaraldehydeIPBS, and viewed by phase contrast microscopy. Bound cells were counted using a 10× objective and an eyepiece reticle. Cells were counted in four fields per dot.

Each substrate protein was tested in triplicate. The number of cells bound for each protein or polypeptide substrate was expressed as the average of the twelve measurements+/−standard deviation.

CT, coated at a concentration of 20 μg/ml, was used as a protein substrate for SL29 fibroblast attachment. The fibroblasts readily attached to the CT-coated substrate (not shown).

To determine which domains of cytotactin mediate the individual attachment activities, fusion proteins spanning the entire length of the molecule were generated and tested for cell attachment activity. Fragments of CT were generated using the pGEX fusion protein system, as described in Example 1 herein, and were analyzed by SDS-PAGE. Fragments identified herein as CTfn3, CTfn6, and CTfg, when coated on plastic at 0.75 μM concentration, supported robust SL29 cell attachment. Both robust attachment and spreading of cells was observed on the CTfn3 substrate. Robust cell attachment, but little or no spreading, was observed on both the CTfn6 and CTfg substrates.

GST (control) and cytotactin fragments identified herein as CTegf, CTfn1–2, CTfn4, CTfn5, and Ctfn7–8, when coated on plastic at three times the concentration used for the CTfn3, CTfn6, and CTfg fragments, did not display any significant attachment activity (less that 1 cell per field).

Although plastic was used as a solid support for substrate) to which the proteinipolypeptide substrates were attached (or upon which they were coated), it should be appreciated that a variety of substrates are useful solid supports upon which CT proteins or peptides may be coated. For example, glass, synthetic resin fiber (e.g., nitrocellulose, polyester, polyethylene, and the like), agarose, long-chain polysaccharides, and similar substances may appropriately be used as solid supports or substrates.

Next, in order to determine the nature of the receptors mediating attachment to CT, specific inhibitors of attachment, including RGD-containing peptides of differing specificities, were added to the cells before plating on CT.

Both soluble GRGDSP (SEQ ID NO 11) or GRGDTP (SEQ ID NO 12) peptides could partially inhibit attachment to CT by 73% and 70%, respectively.

JG22, a function-blocking monoclonal antibody against $\beta_1$ integrin, caused a 22% decrease in attachment when added before plating. Attachment activity was completely abolished, however, when both RGD peptides and JG22 were added. These results are consistent with previous reports suggesting that two integrin binding sites exist on CT.

To determine which receptors are involved in cellular attachment to cytotactin fragments, the same inhibitors of attachment used for intact CT were added to the cells before plating on the above-noted CT fragments. While soluble GRGDSP (SEQ ID NO 11) peptide completely inhibited attachment to CTfn3, attachment to CTfn6 was only partially inhibited and attachment to CTfg was unaffected. In contrast, GRGDTP peptide (SEQ ID NO 12) selectively inhibited attachment to CTfn3 but was ineffective against CTfn6. GRGDTP peptide (SEQ ID NO 12) has been shown previously to inhibit binding to collagen I while GRGDSP (SEQ ID NO 11) generally has no effect (Hynes, *Cell* 69: 11–25 (1992)).

Our results indicated that soluble RGD-containing peptides completely inhibited attachment to CTfn3. The synthetic hexapeptide GRGDSP—but not GRGDTP—could inhibit attachment to CTfn6; The function-blocking anti-$\beta_1$ integrin monoclonal antibody, JG22, inhibited attachment to CTfn6 while having no effect on attachment to CTfn3 or CTfg. While neither RGD-containing peptides nor the JG22 monoclonal antibody could completely inhibit attachment to intact CT, a combination of the two abolished all attachment activity, suggesting that the receptors that bind to CTfn3 and CTfn6 can also bind to the intact molecule.

Monoclonal antibody JG22 only affected attachment to CTfn6. The above results suggest that two separate integrin receptors mediate SL29 attachment to both CTfn3 and CTfn6. Attachment to CTfn3 is selectively inhibitable by an RGD-containing peptide variant previously shown to have altered specificity. In addition, one site for $\beta_1$ integrin binding in CT is localized to the sixth fibronectin type III repeat.

Our data indicate that the third type III (CTfn3) repeat can mediate RGD-dependent cell attachment via integrins $\alpha_v\beta_3$ and $\alpha_v\beta_6$; binding to a $\beta_1$ integrin was observed for the whole molecule but its binding site was not determined. The results presented herein identify the domains of CT that relate to CT binding to $\beta_1$ integrins, which are important in neurite outgrowth promotion. A fusion protein spanning the sixth fibronectin repeat (Ctfn6) was found to support fibroblast and neuronal cell attachment; this attachment was mediated by binding to a $\beta_1$ integrin. In addition, chick fibroblasts and dorsal root ganglion neurons attached well to CTfn3 and CTfg.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A substantially pure cytotactin polypeptide consisting of an amino acid residue sequence selected from the group consisting of SEQ ID NO 5, SEQ ID NO 6 and SEQ ID NO 7, wherein the sequences are fibronectin (Fn) type III repeats respectively in human, mouse and chicken cytotactin.

2. The polypeptide according to claim 1 incorporated into a bioabsorbable matrix.

3. A cytotactin fusion polypeptide consisting of an amino acid residue sequence in SEQ ID NO 29, wherein the sequence is a fibronectin (Fn) type III repeat in chicken cytotactin.

4. The polypeptide according to claim 3 incorporated into a bioabsorbable matrix.

5. A method for preparing a solid support, said method comprising coating or impregnating said solid support with a biological material including a cytotactin polypeptide of claim 1 or claim 3.

6. The method of claim 5 wherein said biological material comprises a bioabsorbable biopolymer.

7. The method of claim 5 wherein said solid support is selected from the group consisting of:

a porous tissue culture insert;

a prosthetic device;

an implant; and a suture.

8. The method of claim 7 wherein said biological material comprises a bioabsorbable biopolymer comprising one or more macromolecules selected from the group consisting of collagen, elastin, fibronectin, vitronectin, laminin, hyaluronic acid, chondroitin sulfate, dermatan sulfate, heparin sulfate, heparin, fibrin, cellulose, gelatin, polylysine, echinonectin, entactin, thrombospondin, uvomorulin, biglycan, decorin, and dextran.

9. The method of claim 8 wherein said biological material further comprises at least one attachment factor selected from the group consisting of collagen (all types), fibronectin, gelatin, laminin, polylysine, vitronectin, cytotactin, echinonectin, entactin, thrombospondin, uvomorulin, biglycan, chondroitin sulfate, decorin, dermatan sulfate, heparin, and hyaluronic acid.

* * * * *

SEQUENCE LISTING

<160> NUMBER OF SEQ ID NOS: 30

<210> SEQ ID NO 1
<211> LENGTH: 7286
<212> TYPE: DNA
<213> ORGANISM: Homo Sapiens
<220> FEATURE:
<221> NAME/KEY: CDS
<222> LOCATION: (55)..(6654)

<400> SEQUENCE: 1

```
gaattcgcta gagccctaga gccccagcag cacccagcca aacccacctc cacc atg          57
                                                             Met
                                                               1 ggg gcc atg act cag ctg ttg gca ggt gtc ttt ctt gct ttc ctt gcc         105
Gly Ala Met Thr Gln Leu Leu Ala Gly Val Phe Leu Ala Phe Leu Ala
          5                  10                  15 ctc gct acc gaa ggt ggg gtc ctc aag aaa gtc atc cgg cac aag cga         153
Leu Ala Thr Glu Gly Gly Val Leu Lys Lys Val Ile Arg His Lys Arg
     20                  25                  30 cag agt ggg gtg aac gcc acc ctg cca gaa gag aac cag cca gtg gtg         201
Gln Ser Gly Val Asn Ala Thr Leu Pro Glu Glu Asn Gln Pro Val Val
 35                  40                  45 ttt aac cac gtt tac aac atc aag ctg cca gtg gga tcc cag tgt tcg         249
Phe Asn His Val Tyr Asn Ile Lys Leu Pro Val Gly Ser Gln Cys Ser
 50                  55                  60                  65 gtg gat ctg gag tca gcc agt ggg gag aaa gac ctg gca ccg cct tca         297
Val Asp Leu Glu Ser Ala Ser Gly Glu Lys Asp Leu Ala Pro Pro Ser
                 70                  75                  80 gag ccc agc gaa agc ttt cag gag cac aca gta gat ggg gaa aac cag         345
Glu Pro Ser Glu Ser Phe Gln Glu His Thr Val Asp Gly Glu Asn Gln
             85                  90                  95 att gtc ttc aca cat cgc atc aac atc ccc cgc cgg gcc tgt ggc tgt         393
Ile Val Phe Thr His Arg Ile Asn Ile Pro Arg Arg Ala Cys Gly Cys
        100                 105                 110 gcc gca gcc cct gat gtt aag gag ctg ctg agc aga ctg gag gag ctg         441
Ala Ala Ala Pro Asp Val Lys Glu Leu Leu Ser Arg Leu Glu Glu Leu
    115                 120                 125 gag aac ctg gtg tct tcc ctg agg gag caa tgt act gca gga gca ggc         489
Glu Asn Leu Val Ser Ser Leu Arg Glu Gln Cys Thr Ala Gly Ala Gly
130                 135                 140                 145 tgc tgt ctc cag cct gcc aca ggc cgc ttg gac acc agg ccc ttc tgt         537
Cys Cys Leu Gln Pro Ala Thr Gly Arg Leu Asp Thr Arg Pro Phe Cys
                150                 155                 160 agc ggt cgg ggc aac ttc agc act gaa gga tgt ggc tgt gtc tgc gaa         585
Ser Gly Arg Gly Asn Phe Ser Thr Glu Gly Cys Gly Cys Val Cys Glu
            165                 170                 175 cct ggc tgg aaa ggc ccc aac tgc tct gag ccc gaa tgt cca ggc aac         633
Pro Gly Trp Lys Gly Pro Asn Cys Ser Glu Pro Glu Cys Pro Gly Asn
        180                 185                 190 tgt cac ctt cga ggc cgg tgc att gat ggg cag tgc atc tgt gac gac         681
Cys His Leu Arg Gly Arg Cys Ile Asp Gly Gln Cys Ile Cys Asp Asp
    195                 200                 205 ggc ttc acg ggc gag gac tgc agc cag ctg gct tgc ccc agc gac tgc         729
Gly Phe Thr Gly Glu Asp Cys Ser Gln Leu Ala Cys Pro Ser Asp Cys
210                 215                 220                 225 aat gac cag ggc aag tgc gtg aat gga gtc tgc atc tgt ttc gaa ggc         777
Asn Asp Gln Gly Lys Cys Val Asn Gly Val Cys Ile Cys Phe Glu Gly
                230                 235                 240
```

-continued

```
tac gcg gct gac tgc agc cgt gaa atc tgc cca gtg ccc tgc agt gag        825
Tyr Ala Ala Asp Cys Ser Arg Glu Ile Cys Pro Val Pro Cys Ser Glu
        245                 250                 255 gag cac ggc aca tgt gta gat ggc ttg tgt gtg tgc cac gat ggc ttt        873
Glu His Gly Thr Cys Val Asp Gly Leu Cys Val Cys His Asp Gly Phe
        260                 265                 270 gca ggc gat gac tgc aac aag cct ctg tgt ctc aac aat tgc tac aac        921
Ala Gly Asp Asp Cys Asn Lys Pro Leu Cys Leu Asn Asn Cys Tyr Asn
    275                 280                 285 cgt gga cga tgc gtg gag aat gag tgc gtg tgt gat gag ggt ttc acg        969
Arg Gly Arg Cys Val Glu Asn Glu Cys Val Cys Asp Glu Gly Phe Thr
290                 295                 300                 305 ggc gaa gac tgc agt gag ctc atc tgc ccc aat gac tgc ttc gac cgg       1017
Gly Glu Asp Cys Ser Glu Leu Ile Cys Pro Asn Asp Cys Phe Asp Arg
                310                 315                 320 ggc cgc tgc atc aat ggc acc tgc tac tgc gaa gaa ggc ttc aca ggt       1065
Gly Arg Cys Ile Asn Gly Thr Cys Tyr Cys Glu Glu Gly Phe Thr Gly
                325                 330                 335 gaa gac tgc ggg aaa ccc acc tgc cca cat gcc tgc cac acc cag ggc       1113
Glu Asp Cys Gly Lys Pro Thr Cys Pro His Ala Cys His Thr Gln Gly
            340                 345                 350 cgg tgt gag gag ggg cag tgt gta tgt gat gag ggc ttt gcc ggt gtg       1161
Arg Cys Glu Glu Gly Gln Cys Val Cys Asp Glu Gly Phe Ala Gly Val
        355                 360                 365 gac tgc agc gag aag agg tgt cct gct gac tgt cac aat cgt ggc cgc       1209
Asp Cys Ser Glu Lys Arg Cys Pro Ala Asp Cys His Asn Arg Gly Arg
370                 375                 380                 385 tgt gta gac ggg cgg tgt gag tgt gat gat ggt ttc act gga gct gac       1257
Cys Val Asp Gly Arg Cys Glu Cys Asp Asp Gly Phe Thr Gly Ala Asp
                390                 395                 400 tgt ggg gag ctc aag tgt ccc aat ggc tgc agt ggc cat ggc cgc tgt       1305
Cys Gly Glu Leu Lys Cys Pro Asn Gly Cys Ser Gly His Gly Arg Cys
                405                 410                 415 gtc aat ggg cag tgt gtg tgt gat gag ggc tat act ggg gag gac tgc       1353
Val Asn Gly Gln Cys Val Cys Asp Glu Gly Tyr Thr Gly Glu Asp Cys
            420                 425                 430 agc cag cta cgg tgt ccc aat gac tgt cac agt cgg ggc cgc tgt gtc       1401
Ser Gln Leu Arg Cys Pro Asn Asp Cys His Ser Arg Gly Arg Cys Val
        435                 440                 445 gag ggc aaa tgt gta tgt gag caa ggc ttc aag ggc tat gac tgc agt       1449
Glu Gly Lys Cys Val Cys Glu Gln Gly Phe Lys Gly Tyr Asp Cys Ser
450                 455                 460                 465 gac atg agc tgc cct aat gac tgt cac cag cac ggc cgc tgt gtg aat       1497
Asp Met Ser Cys Pro Asn Asp Cys His Gln His Gly Arg Cys Val Asn
                470                 475                 480 ggc atg tgt gtt tgt gat gac ggc tac aca ggg gaa gac tgc cgg gat       1545
Gly Met Cys Val Cys Asp Asp Gly Tyr Thr Gly Glu Asp Cys Arg Asp
                485                 490                 495 cgc caa tgc ccc agg gac tgc agc aac agg ggc ctc tgt gtg gac gga       1593
Arg Gln Cys Pro Arg Asp Cys Ser Asn Arg Gly Leu Cys Val Asp Gly
            500                 505                 510 cag tgc gtc tgt gag gac ggc ttc acc ggc cct gac tgt gca gaa ctc       1641
Gln Cys Val Cys Glu Asp Gly Phe Thr Gly Pro Asp Cys Ala Glu Leu
        515                 520                 525 tcc tgt cca aat gac tgc cat ggc cag ggt cgc tgt gtg aat ggg cag       1689
Ser Cys Pro Asn Asp Cys His Gly Gln Gly Arg Cys Val Asn Gly Gln
530                 535                 540                 545 tgc gtg tgc cat gaa gga ttt atg ggc aaa gac tgc aag gag caa aga       1737
Cys Val Cys His Glu Gly Phe Met Gly Lys Asp Cys Lys Glu Gln Arg
                550                 555                 560
```

```
tgt ccc agt gac tgt cat ggc cag ggc cgc tgc gtg gac ggc cag tgc      1785
Cys Pro Ser Asp Cys His Gly Gln Gly Arg Cys Val Asp Gly Gln Cys
            565                 570                 575 atc tgc cac gag ggc ttc aca ggc ctg gac tgt ggc cag cac tcc tgc      1833
Ile Cys His Glu Gly Phe Thr Gly Leu Asp Cys Gly Gln His Ser Cys
        580                 585                 590 ccc agt gac tgc aac aac tta gga caa tgc gtc tcg ggc cgc tgc atc      1881
Pro Ser Asp Cys Asn Asn Leu Gly Gln Cys Val Ser Gly Arg Cys Ile
595                 600                 605 tgc aac gag ggc tac agc gga gaa gac tgc tca gag gtg tct cct ccc      1929
Cys Asn Glu Gly Tyr Ser Gly Glu Asp Cys Ser Glu Val Ser Pro Pro
610                 615                 620                 625 aaa gac ctc gtt gtg aca gaa gtg acg gaa gag acg gtc aac ctg gcc      1977
Lys Asp Leu Val Val Thr Glu Val Thr Glu Glu Thr Val Asn Leu Ala
            630                 635                 640 tgg gac aat gag atg cgg gtc aca gag tac ctt gtc gtg tac acg ccc      2025
Trp Asp Asn Glu Met Arg Val Thr Glu Tyr Leu Val Val Tyr Thr Pro
                645                 650                 655 acc cac gag ggt ggt ctg gaa atg cag ttc cgt gtg cct ggg gac cag      2073
Thr His Glu Gly Gly Leu Glu Met Gln Phe Arg Val Pro Gly Asp Gln
            660                 665                 670 acg tcc acc atc atc cgg gag ctg gag cct ggt gtg gag tac ttt atc      2121
Thr Ser Thr Ile Ile Arg Glu Leu Glu Pro Gly Val Glu Tyr Phe Ile
        675                 680                 685 cgt gta ttt gcc atc ctg gag aac aag aag agc att cct gtc agc gcc      2169
Arg Val Phe Ala Ile Leu Glu Asn Lys Lys Ser Ile Pro Val Ser Ala
690                 695                 700                 705 agg gtg gcc acg tac tta cct gca cct gaa ggc ctg aaa ttc aag tcc      2217
Arg Val Ala Thr Tyr Leu Pro Ala Pro Glu Gly Leu Lys Phe Lys Ser
                710                 715                 720 atc aag gag aca tct gtg gaa gtg gag tgg gat cct cta gac att gct      2265
Ile Lys Glu Thr Ser Val Glu Val Glu Trp Asp Pro Leu Asp Ile Ala
            725                 730                 735 ttt gaa acc tgg gag atc atc ttc cgg aat atg aat aaa gaa gat gag      2313
Phe Glu Thr Trp Glu Ile Ile Phe Arg Asn Met Asn Lys Glu Asp Glu
        740                 745                 750 gga gag atc acc aaa agc ctg agg agg cca gag acc tct tac cgg caa      2361
Gly Glu Ile Thr Lys Ser Leu Arg Arg Pro Glu Thr Ser Tyr Arg Gln
755                 760                 765 act ggt cta gct cct ggg caa gag tat gag ata tct ctg cac ata gtg      2409
Thr Gly Leu Ala Pro Gly Gln Glu Tyr Glu Ile Ser Leu His Ile Val
770                 775                 780                 785 aaa aac aat acc cgg ggc cct ggc ctg aag agg gtg acc acc aca cgc      2457
Lys Asn Asn Thr Arg Gly Pro Gly Leu Lys Arg Val Thr Thr Thr Arg
                790                 795                 800 ttg gat gcc ccc agc cag atc gag gtg aaa gat gtc aca gac acc act      2505
Leu Asp Ala Pro Ser Gln Ile Glu Val Lys Asp Val Thr Asp Thr Thr
            805                 810                 815 gcc ttg atc acc tgg ttc aag ccc ctg gct gag atc gat ggc att gag      2553
Ala Leu Ile Thr Trp Phe Lys Pro Leu Ala Glu Ile Asp Gly Ile Glu
        820                 825                 830 ctg acc tac ggc atc aaa gac gtg cca gga gac cgt acc acc atc gat      2601
Leu Thr Tyr Gly Ile Lys Asp Val Pro Gly Asp Arg Thr Thr Ile Asp
835                 840                 845 ctc aca gag gac gag aac cag tac tcc atc ggg aac ctg aag cct gac      2649
Leu Thr Glu Asp Glu Asn Gln Tyr Ser Ile Gly Asn Leu Lys Pro Asp
850                 855                 860                 865 act gag tac gag gtg tcc ctc atc tcc cgc aga ggt gac atg tca agc      2697
Thr Glu Tyr Glu Val Ser Leu Ile Ser Arg Arg Gly Asp Met Ser Ser
```

-continued

|  |  | 870 |  |  | 875 |  |  | 880 |  |  |  |
|---|---|---|---|---|---|---|---|---|---|---|---|

```
aac cca gcc aaa gag acc ttc aca aca ggc ctc gat gct ccc agg aat    2745
Asn Pro Ala Lys Glu Thr Phe Thr Thr Gly Leu Asp Ala Pro Arg Asn
         885                 890                 895 ctt cga cgt gtt tcc cag aca gat aac agc atc acc ctg gaa tgg agg    2793
Leu Arg Arg Val Ser Gln Thr Asp Asn Ser Ile Thr Leu Glu Trp Arg
        900                 905                 910 aat ggc aag gca gct att gac agt tac aga att aag tat gcc ccc atc    2841
Asn Gly Lys Ala Ala Ile Asp Ser Tyr Arg Ile Lys Tyr Ala Pro Ile
        915                 920                 925 tct gga ggg gac cac gct gag gtt gat gtt cca aag agc caa caa gcc    2889
Ser Gly Gly Asp His Ala Glu Val Asp Val Pro Lys Ser Gln Gln Ala
930                 935                 940                 945 aca acc aaa acc aca ctc aca ggt ctg agg ccg gga act gaa tat ggg    2937
Thr Thr Lys Thr Thr Leu Thr Gly Leu Arg Pro Gly Thr Glu Tyr Gly
            950                 955                 960 att gga gtt tct gct gtg aag gaa gac aag gag agc aat cca gcg acc    2985
Ile Gly Val Ser Ala Val Lys Glu Asp Lys Glu Ser Asn Pro Ala Thr
            965                 970                 975 atc aac gca gcc aca gag ttg gac acg ccc aag gac ctt cag gtt tct    3033
Ile Asn Ala Ala Thr Glu Leu Asp Thr Pro Lys Asp Leu Gln Val Ser
        980                 985                 990 gaa act gca gag acc agc ctg acc ctg ctc tgg aag aca ccg ttg gcc    3081
Glu Thr Ala Glu Thr Ser Leu Thr Leu Leu Trp Lys Thr Pro Leu Ala
        995                 1000                1005 aaa ttt gac cgc tac cgc ctc aat tac agt ctc ccc aca ggc cag tgg    3129
Lys Phe Asp Arg Tyr Arg Leu Asn Tyr Ser Leu Pro Thr Gly Gln Trp
1010                1015                1020                1025 gtg gga gtg cag ctt cca aga aac acc act tcc tat gtc ctg aga ggc    3177
Val Gly Val Gln Leu Pro Arg Asn Thr Thr Ser Tyr Val Leu Arg Gly
            1030                1035                1040 ctg gaa cca gga cag gag tac aat gtc ctc ctg aca gcc gag aaa ggc    3225
Leu Glu Pro Gly Gln Glu Tyr Asn Val Leu Leu Thr Ala Glu Lys Gly
            1045                1050                1055 aga cac aag agc aag ccc gca cgt gtg aag gca tcc act gaa caa gcc    3273
Arg His Lys Ser Lys Pro Ala Arg Val Lys Ala Ser Thr Glu Gln Ala
        1060                1065                1070 cct gag ctg gaa aac ctc acc gtg act gag gtt ggc tgg gat ggc ctc    3321
Pro Glu Leu Glu Asn Leu Thr Val Thr Glu Val Gly Trp Asp Gly Leu
    1075                1080                1085 aga ctc aac tgg acc gcg gct gac cag gcc tat gag cac ttt atc att    3369
Arg Leu Asn Trp Thr Ala Ala Asp Gln Ala Tyr Glu His Phe Ile Ile
1090                1095                1100                1105 cag gtg cag gag gcc aac aag gtg gag gca gct cgg aac ctc acc gtg    3417
Gln Val Gln Glu Ala Asn Lys Val Glu Ala Ala Arg Asn Leu Thr Val
            1110                1115                1120 cct ggc agc ctt cgg gct gtg gac ata ccg ggc ctc aag gct gct acg    3465
Pro Gly Ser Leu Arg Ala Val Asp Ile Pro Gly Leu Lys Ala Ala Thr
        1125                1130                1135 cct tat aca gtc tcc atc tat ggg gtg atc cag ggc tat aga aca cca    3513
Pro Tyr Thr Val Ser Ile Tyr Gly Val Ile Gln Gly Tyr Arg Thr Pro
        1140                1145                1150 gtg ctc tct gct gag gcc tcc aca ggg gaa act ccc aat ttg gga gag    3561
Val Leu Ser Ala Glu Ala Ser Thr Gly Glu Thr Pro Asn Leu Gly Glu
    1155                1160                1165 gtc gtg gtg gcc gag gtg ggc tgg gat gcc ctc aaa ctc aac tgg act    3609
Val Val Val Ala Glu Val Gly Trp Asp Ala Leu Lys Leu Asn Trp Thr
1170                1175                1180                1185 gct cca gaa ggg gcc tat gag tac ttt ttc att cag gtg cag gag gct    3657
```

-continued

```
Ala Pro Glu Gly Ala Tyr Glu Tyr Phe Phe Ile Gln Val Gln Glu Ala
            1190                1195                1200 gac aca gta gag gca gcc cag aac ctc acc gtc cca gga gga ctg agg        3705
Asp Thr Val Glu Ala Ala Gln Asn Leu Thr Val Pro Gly Gly Leu Arg
        1205                1210                1215 tcc aca gac ctg cct ggg ctc aaa gca gcc act cat tat acc atc acc        3753
Ser Thr Asp Leu Pro Gly Leu Lys Ala Ala Thr His Tyr Thr Ile Thr
    1220                1225                1230 atc cgc ggg gtc act cag gac ttc agc aca acc cct ctc tct gtt gaa        3801
Ile Arg Gly Val Thr Gln Asp Phe Ser Thr Thr Pro Leu Ser Val Glu
1235                1240                1245 gtc ttg aca gag gag gtt cca gat atg gga aac ctc aca gtg acc gag        3849
Val Leu Thr Glu Glu Val Pro Asp Met Gly Asn Leu Thr Val Thr Glu
1250                1255                1260                1265 gtt agc tgg gat gct ctc aga ctg aac tgg acc acg cca gat gga acc        3897
Val Ser Trp Asp Ala Leu Arg Leu Asn Trp Thr Thr Pro Asp Gly Thr
        1270                1275                1280 tat gac cag ttt act att cag gtc cag gag gct gac cag gtg gaa gag        3945
Tyr Asp Gln Phe Thr Ile Gln Val Gln Glu Ala Asp Gln Val Glu Glu
    1285                1290                1295 gct cac aat ctc acg gtt cct ggc agc ctg cgt tcc atg gaa atc cca        3993
Ala His Asn Leu Thr Val Pro Gly Ser Leu Arg Ser Met Glu Ile Pro
1300                1305                1310 ggc ctc agg gct ggc act cct tac aca gtc acc ctg cac ggc gag gtc        4041
Gly Leu Arg Ala Gly Thr Pro Tyr Thr Val Thr Leu His Gly Glu Val
1315                1320                1325 agg ggc cac agc act cga ccc ctt gct gta gag gtc gtc aca gag gat        4089
Arg Gly His Ser Thr Arg Pro Leu Ala Val Glu Val Val Thr Glu Asp
1330                1335                1340                1345 ctc cca cag ctg gga gat tta gcc gtg tct gag gtt ggc tgg gat ggc        4137
Leu Pro Gln Leu Gly Asp Leu Ala Val Ser Glu Val Gly Trp Asp Gly
        1350                1355                1360 ctc aga ctc aac tgg acc gca gct gac aat gcc tat gag cac ttt gtc        4185
Leu Arg Leu Asn Trp Thr Ala Ala Asp Asn Ala Tyr Glu His Phe Val
    1365                1370                1375 att cag gtg cag gag gtc aac aaa gtg gag gca gcc cag aac ctc acg        4233
Ile Gln Val Gln Glu Val Asn Lys Val Glu Ala Ala Gln Asn Leu Thr
1380                1385                1390 ttg cct ggc agc ctc agg gct gtg gac atc ccg ggc ctc gag gct gcc        4281
Leu Pro Gly Ser Leu Arg Ala Val Asp Ile Pro Gly Leu Glu Ala Ala
1395                1400                1405 acg cct tat aga gtc tcc atc tat ggg gtg atc cgg ggc tat aga aca        4329
Thr Pro Tyr Arg Val Ser Ile Tyr Gly Val Ile Arg Gly Tyr Arg Thr
1410                1415                1420                1425 cca gta ctc tct gct gag gcc tcc aca gcc aaa gaa cct gaa att gga        4377
Pro Val Leu Ser Ala Glu Ala Ser Thr Ala Lys Glu Pro Glu Ile Gly
        1430                1435                1440 aac tta aat gtt tct gac ata act ccc gag agc ttc aat ctc tcc tgg        4425
Asn Leu Asn Val Ser Asp Ile Thr Pro Glu Ser Phe Asn Leu Ser Trp
    1445                1450                1455 atg gct acc gat ggg atc ttc gag acc ttt acc att gaa att att gat        4473
Met Ala Thr Asp Gly Ile Phe Glu Thr Phe Thr Ile Glu Ile Ile Asp
1460                1465                1470 tcc aat agg ttg ctg gag act gtg gaa tat aat atc tct ggt gct gaa        4521
Ser Asn Arg Leu Leu Glu Thr Val Glu Tyr Asn Ile Ser Gly Ala Glu
1475                1480                1485 cga act gcc cat atc tca ggg cta ccc cct agt act gat ttt att gtc        4569
Arg Thr Ala His Ile Ser Gly Leu Pro Pro Ser Thr Asp Phe Ile Val
1490                1495                1500                1505
```

-continued

| | |
|---|---|
| tac ctc tct gga ctt gct ccc agc atc cgg acc aaa acc atc agt gcc<br>Tyr Leu Ser Gly Leu Ala Pro Ser Ile Arg Thr Lys Thr Ile Ser Ala<br>          1510                   1515                   1520 | 4617 |
| aca gcc acg aca gag gcc ctg ccc ctt ctg gaa aac cta acc att tcc<br>Thr Ala Thr Thr Glu Ala Leu Pro Leu Leu Glu Asn Leu Thr Ile Ser<br>        1525                   1530                   1535 | 4665 |
| gac att aat ccc tac ggg ttc aca gtt tcc tgg atg gca tcg gag aat<br>Asp Ile Asn Pro Tyr Gly Phe Thr Val Ser Trp Met Ala Ser Glu Asn<br>1540                   1545                   1550 | 4713 |
| gcc ttt gac agc ttt cta gta acg gtg gtg gat tct ggg aag ctg ctg<br>Ala Phe Asp Ser Phe Leu Val Thr Val Val Asp Ser Gly Lys Leu Leu<br>      1555                   1560                   1565 | 4761 |
| gac ccc cag gaa ttc aca ctt tca gga acc cag agg aag ctg gag ctt<br>Asp Pro Gln Glu Phe Thr Leu Ser Gly Thr Gln Arg Lys Leu Glu Leu<br>1570                   1575                   1580                   1585 | 4809 |
| aga ggc ctc ata act ggc att ggc tat gag gtt atg gtc tct ggc ttc<br>Arg Gly Leu Ile Thr Gly Ile Gly Tyr Glu Val Met Val Ser Gly Phe<br>            1590                   1595                   1600 | 4857 |
| acc caa ggg cat caa acc aag ccc ttg agg gct gag att gtt aca gaa<br>Thr Gln Gly His Gln Thr Lys Pro Leu Arg Ala Glu Ile Val Thr Glu<br>          1605                   1610                   1615 | 4905 |
| gcc gaa ccg gaa gtt gac aac ctt ctg gtt tca gat gcc acc cca gac<br>Ala Glu Pro Glu Val Asp Asn Leu Leu Val Ser Asp Ala Thr Pro Asp<br>1620                   1625                   1630 | 4953 |
| ggt ttc cgt ctg tcc tgg aca gct gat gaa ggg gtc ttc gac aat ttt<br>Gly Phe Arg Leu Ser Trp Thr Ala Asp Glu Gly Val Phe Asp Asn Phe<br>        1635                   1640                   1645 | 5001 |
| gtt ctc aaa atc aga gat acc aaa aag cag tct gag cca ctg gaa ata<br>Val Leu Lys Ile Arg Asp Thr Lys Lys Gln Ser Glu Pro Leu Glu Ile<br>1650                   1655                   1660                   1665 | 5049 |
| acc cta ctt gcc ccc gaa cgt acc agg gac ata aca ggt ctc aga gag<br>Thr Leu Leu Ala Pro Glu Arg Thr Arg Asp Ile Thr Gly Leu Arg Glu<br>            1670                   1675                   1680 | 5097 |
| gct act gaa tac gaa att gaa ctc tat gga ata agc aaa gga agg cga<br>Ala Thr Glu Tyr Glu Ile Glu Leu Tyr Gly Ile Ser Lys Gly Arg Arg<br>      1685                   1690                   1695 | 5145 |
| tcc cag aca gtc agt gct ata gca aca aca gcc atg ggc tcc cca aag<br>Ser Gln Thr Val Ser Ala Ile Ala Thr Thr Ala Met Gly Ser Pro Lys<br>          1700                   1705                   1710 | 5193 |
| gaa gtc att ttc tca gac atc act gaa aat tcg gct act gtc agc tgg<br>Glu Val Ile Phe Ser Asp Ile Thr Glu Asn Ser Ala Thr Val Ser Trp<br>1715                   1720                   1725 | 5241 |
| agg gca ccc acg gcc caa gtg gag agc ttc cgg att acc tat gtg ccc<br>Arg Ala Pro Thr Ala Gln Val Glu Ser Phe Arg Ile Thr Tyr Val Pro<br>1730                   1735                   1740                   1745 | 5289 |
| att aca gga ggt aca ccc tcc atg gta act gtg gac gga acc aag act<br>Ile Thr Gly Gly Thr Pro Ser Met Val Thr Val Asp Gly Thr Lys Thr<br>            1750                   1755                   1760 | 5337 |
| cag acc agg ctg gtg aaa ctc ata cct ggc gtg gag tac ctt gtc agc<br>Gln Thr Arg Leu Val Lys Leu Ile Pro Gly Val Glu Tyr Leu Val Ser<br>          1765                   1770                   1775 | 5385 |
| atc atc gcc atg aag ggc ttt gag gaa agt gaa cct gtc tca ggg tca<br>Ile Ile Ala Met Lys Gly Phe Glu Glu Ser Glu Pro Val Ser Gly Ser<br>1780                   1785                   1790 | 5433 |
| ttc acc aca gct ctg gat ggc cca tct ggc ctg gtg aca gcc aac atc<br>Phe Thr Thr Ala Leu Asp Gly Pro Ser Gly Leu Val Thr Ala Asn Ile<br>        1795                   1800                   1805 | 5481 |
| act gac tca gaa gcc ttg gcc agg tgg cag cca gcc att gcc act gtg<br>Thr Asp Ser Glu Ala Leu Ala Arg Trp Gln Pro Ala Ile Ala Thr Val<br>1810                   1815                   1820                   1825 | 5529 |

```
gac agt tat gtc atc tcc tac aca ggc gag aaa gtg cca gaa att aca        5577
Asp Ser Tyr Val Ile Ser Tyr Thr Gly Glu Lys Val Pro Glu Ile Thr
                1830                1835                1840 cgc acg gtg tcc ggg aac aca gtg gag tat gct ctg acc gac ctc gag        5625
Arg Thr Val Ser Gly Asn Thr Val Glu Tyr Ala Leu Thr Asp Leu Glu
            1845                1850                1855 cct gcc acg gaa tac aca ctg aga atc ttt gca gag aaa ggg ccc cag        5673
Pro Ala Thr Glu Tyr Thr Leu Arg Ile Phe Ala Glu Lys Gly Pro Gln
        1860                1865                1870 aag agc tca acc atc act gcc aag ttc aca aca gac ctc gat tct cca        5721
Lys Ser Ser Thr Ile Thr Ala Lys Phe Thr Thr Asp Leu Asp Ser Pro
    1875                1880                1885 aga gac ttg act gct act gag gtt cag tcg gaa act gcc ctc ctt acc        5769
Arg Asp Leu Thr Ala Thr Glu Val Gln Ser Glu Thr Ala Leu Leu Thr
1890                1895                1900                1905 tgg cga ccc ccc cgg gca tca gtc acc ggt tac ctg ctg gtc tat gaa        5817
Trp Arg Pro Pro Arg Ala Ser Val Thr Gly Tyr Leu Leu Val Tyr Glu
                1910                1915                1920 tca gtg gat ggc aca gtc aag gaa gtc att gtg ggt cca gat acc acc        5865
Ser Val Asp Gly Thr Val Lys Glu Val Ile Val Gly Pro Asp Thr Thr
            1925                1930                1935 tcc tac agc ctg gca gac ctg agc cca tcc acc cac tac aca gcc aag        5913
Ser Tyr Ser Leu Ala Asp Leu Ser Pro Ser Thr His Tyr Thr Ala Lys
        1940                1945                1950 atc cag gca ctc aat ggg ccc ctg agg agc aat atg atc cag acc atc        5961
Ile Gln Ala Leu Asn Gly Pro Leu Arg Ser Asn Met Ile Gln Thr Ile
    1955                1960                1965 ttc acc aca att gga ctc ctg tac ccc ttc ccc aag gac tgc tcc caa        6009
Phe Thr Thr Ile Gly Leu Leu Tyr Pro Phe Pro Lys Asp Cys Ser Gln
1970                1975                1980                1985 gca atg ctg aat gga gac acg acc tct ggc ctc tac acc att tat ctg        6057
Ala Met Leu Asn Gly Asp Thr Thr Ser Gly Leu Tyr Thr Ile Tyr Leu
                1990                1995                2000 aat ggt gat aag gct cag gcg ctg gaa gtc ttc tgt gac atg acc tct        6105
Asn Gly Asp Lys Ala Gln Ala Leu Glu Val Phe Cys Asp Met Thr Ser
            2005                2010                2015 gat ggg ggt gga tgg att gtg ttc ctg aga cgc aaa aac gga cgc gag        6153
Asp Gly Gly Gly Trp Ile Val Phe Leu Arg Arg Lys Asn Gly Arg Glu
        2020                2025                2030 aac ttc tac caa aac tgg aag gca tat gct gct gga ttt ggg gac cgc        6201
Asn Phe Tyr Gln Asn Trp Lys Ala Tyr Ala Ala Gly Phe Gly Asp Arg
    2035                2040                2045 aga gaa gaa ttc tgg ctt ggg ctg gac aac ctg aac aaa atc aca gcc        6249
Arg Glu Glu Phe Trp Leu Gly Leu Asp Asn Leu Asn Lys Ile Thr Ala
2050                2055                2060                2065 cag ggg cag tac gag ctc cgg gtg gac ctg cgg gac cat ggg gag aca        6297
Gln Gly Gln Tyr Glu Leu Arg Val Asp Leu Arg Asp His Gly Glu Thr
                2070                2075                2080 gcc ttt gct gtc tat gac aag ttc agc gtg gga gat gcc aag act cgc        6345
Ala Phe Ala Val Tyr Asp Lys Phe Ser Val Gly Asp Ala Lys Thr Arg
            2085                2090                2095 tac aag ctg aag gtg gag ggg tac agt ggg aca gca ggt gac tcc atg        6393
Tyr Lys Leu Lys Val Glu Gly Tyr Ser Gly Thr Ala Gly Asp Ser Met
        2100                2105                2110 gcc tac cac aat ggc aga tcc ttc tcc acc ttt gac aag gac aca gat        6441
Ala Tyr His Asn Gly Arg Ser Phe Ser Thr Phe Asp Lys Asp Thr Asp
    2115                2120                2125 tca gcc atc acc aac tgt gct ctg tct aca agg ggc ttc tgg tac agg        6489
Ser Ala Ile Thr Asn Cys Ala Leu Ser Thr Arg Gly Phe Trp Tyr Arg
```

-continued

```
                2130                2135                2140                2145
aac tgt cac cgt gtc aac ctg atg ggg aga tat ggg gac aat aac cac          6537
Asn Cys His Arg Val Asn Leu Met Gly Arg Tyr Gly Asp Asn Asn His
                2150                2155                2160 agt cag ggc gtt aac tgg ttc cac tgg aag ggc cac gaa cac tca atc          6585
Ser Gln Gly Val Asn Trp Phe His Trp Lys Gly His Glu His Ser Ile
        2165                2170                2175 cag ttt gct gag atg aag ctg aga cca agc aac ttc aga aat ctt gaa          6633
Gln Phe Ala Glu Met Lys Leu Arg Pro Ser Asn Phe Arg Asn Leu Glu
        2180                2185                2190 ggc agg cgc aaa cgg gca taa attggaggga ccactgggtg agagaggaat             6684
Gly Arg Arg Lys Arg Ala
    2195                2200 aaggcggccc agagcgagga aaggatttta ccaaagcatc aatacaacca gcccaaccat        6744
cggtccacac ctgggcattt ggtgagaatc aaagctgacc atggatccct ggggccaacg        6804
gcaacagcat gggcctcacc tcctctgtga tttctttctt tgcaccaaag acatcagtct        6864
ccaacatgtt tctgttttgt tgtttgattc agcaaaaatc tcccagtgac aacatcgcaa        6924
tagtttttta cttctcttag gtggctctgg gatgggagag gggtaggatg tacagggta         6984 gtttgtttta gaaccagccg tattttacat gaagctgtat aattaattgt cattattttt        7044
gttagcaaag attaaatgtg tcattggaag ccatcccttt ttttacattt catacaacag        7104
aaaccagaaa agcaatactg tttccatttt aaggatatga ttaatattat taatataata       7164
atgatgatga tgatgatgaa aactaaggat ttttcaagag atctttcttt ccaaaacatt       7224
tctggacagt acctgattgt atttttttt taaataaaag cacaagtact tttgaaaaaa        7284
aa                                                                        7286
```

<210> SEQ ID NO 2
<211> LENGTH: 2199
<212> TYPE: PRT
<213> ORGANISM: Homo Sapiens

<400> SEQUENCE: 2

```
Met Gly Ala Met Thr Gln Leu Leu Ala Gly Val Phe Leu Ala Phe Leu
 1               5                  10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
```

-continued

```
                    165                 170                 175
   Glu Pro Gly Trp Lys Gly Pro Asn Cys Ser Glu Pro Glu Cys Pro Gly
                   180                 185                 190

Asn Cys His Leu Arg Gly Arg Cys Ile Asp Gly Gln Cys Ile Cys Asp
                   195                 200                 205

Asp Gly Phe Thr Gly Glu Asp Cys Ser Gln Leu Ala Cys Pro Ser Asp
                   210                 215                 220

Cys Asn Asp Gln Gly Lys Cys Val Asn Gly Val Cys Ile Cys Phe Glu
   225                 230                 235                 240

Gly Tyr Ala Ala Asp Cys Ser Arg Glu Ile Cys Pro Val Pro Cys Ser
                   245                 250                 255

Glu Glu His Gly Thr Cys Val Asp Gly Leu Cys Val Cys His Asp Gly
                   260                 265                 270

Phe Ala Gly Asp Asp Cys Asn Lys Pro Leu Cys Leu Asn Asn Cys Tyr
                   275                 280                 285

Asn Arg Gly Arg Cys Val Glu Asn Glu Cys Val Cys Asp Glu Gly Phe
                   290                 295                 300

Thr Gly Glu Asp Cys Ser Glu Leu Ile Cys Pro Asn Asp Cys Phe Asp
   305                 310                 315                 320

Arg Gly Arg Cys Ile Asn Gly Thr Cys Tyr Cys Glu Glu Gly Phe Thr
                   325                 330                 335

Gly Glu Asp Cys Gly Lys Pro Thr Cys Pro His Ala Cys His Thr Gln
                   340                 345                 350

Gly Arg Cys Glu Glu Gly Gln Cys Val Cys Asp Glu Gly Phe Ala Gly
                   355                 360                 365

Val Asp Cys Ser Glu Lys Arg Cys Pro Ala Asp Cys His Asn Arg Gly
                   370                 375                 380

Arg Cys Val Asp Gly Arg Cys Glu Cys Asp Asp Gly Phe Thr Gly Ala
   385                 390                 395                 400

Asp Cys Gly Glu Leu Lys Cys Pro Asn Gly Cys Ser Gly His Gly Arg
                   405                 410                 415

Cys Val Asn Gly Gln Cys Val Cys Asp Glu Gly Tyr Thr Gly Glu Asp
                   420                 425                 430

Cys Ser Gln Leu Arg Cys Pro Asn Asp Cys His Ser Arg Gly Arg Cys
                   435                 440                 445

Val Glu Gly Lys Cys Val Cys Glu Gln Gly Phe Lys Gly Tyr Asp Cys
                   450                 455                 460

Ser Asp Met Ser Cys Pro Asn Asp Cys His Gln His Gly Arg Cys Val
   465                 470                 475                 480

Asn Gly Met Cys Val Cys Asp Asp Gly Tyr Thr Gly Glu Asp Cys Arg
                   485                 490                 495

Asp Arg Gln Cys Pro Arg Asp Cys Ser Asn Arg Gly Leu Cys Val Asp
                   500                 505                 510

Gly Gln Cys Val Cys Glu Asp Gly Phe Thr Gly Pro Asp Cys Ala Glu
                   515                 520                 525

Leu Ser Cys Pro Asn Asp Cys His Gly Gln Gly Arg Cys Val Asn Gly
                   530                 535                 540

Gln Cys Val Cys His Glu Gly Phe Met Gly Lys Asp Cys Lys Glu Gln
   545                 550                 555                 560

Arg Cys Pro Ser Asp Cys His Gly Gln Gly Arg Cys Val Asp Gly Gln
                   565                 570                 575

Cys Ile Cys His Glu Gly Phe Thr Gly Leu Asp Cys Gly Gln His Ser
                   580                 585                 590
```

```
Cys Pro Ser Asp Cys Asn Asn Leu Gly Gln Cys Val Ser Gly Arg Cys
            595                 600                 605

Ile Cys Asn Glu Gly Tyr Ser Gly Glu Asp Cys Ser Glu Val Ser Pro
    610                 615                 620

Pro Lys Asp Leu Val Val Thr Glu Val Thr Glu Thr Val Asn Leu
625                 630                 635                 640

Ala Trp Asp Asn Glu Met Arg Val Thr Glu Tyr Leu Val Val Tyr Thr
                    645                 650                 655

Pro Thr His Glu Gly Gly Leu Glu Met Gln Phe Arg Val Pro Gly Asp
            660                 665                 670

Gln Thr Ser Thr Ile Ile Arg Glu Leu Glu Pro Gly Val Glu Tyr Phe
            675                 680                 685

Ile Arg Val Phe Ala Ile Leu Glu Asn Lys Lys Ser Ile Pro Val Ser
690                 695                 700

Ala Arg Val Ala Thr Tyr Leu Pro Ala Pro Glu Gly Leu Lys Phe Lys
705                 710                 715                 720

Ser Ile Lys Glu Thr Ser Val Glu Val Glu Trp Asp Pro Leu Asp Ile
                725                 730                 735

Ala Phe Glu Thr Trp Glu Ile Ile Phe Arg Asn Met Asn Lys Glu Asp
                740                 745                 750

Glu Gly Glu Ile Thr Lys Ser Leu Arg Arg Pro Glu Thr Ser Tyr Arg
            755                 760                 765

Gln Thr Gly Leu Ala Pro Gly Gln Glu Tyr Glu Ile Ser Leu His Ile
            770                 775                 780

Val Lys Asn Asn Thr Arg Gly Pro Gly Leu Lys Arg Val Thr Thr Thr
785                 790                 795                 800

Arg Leu Asp Ala Pro Ser Gln Ile Glu Val Lys Asp Val Thr Asp Thr
                805                 810                 815

Thr Ala Leu Ile Thr Trp Phe Lys Pro Leu Ala Glu Ile Asp Gly Ile
                820                 825                 830

Glu Leu Thr Tyr Gly Ile Lys Asp Val Pro Gly Asp Arg Thr Thr Ile
            835                 840                 845

Asp Leu Thr Glu Asp Glu Asn Gln Tyr Ser Ile Gly Asn Leu Lys Pro
850                 855                 860

Asp Thr Glu Tyr Glu Val Ser Leu Ile Ser Arg Arg Gly Asp Met Ser
865                 870                 875                 880

Ser Asn Pro Ala Lys Glu Thr Phe Thr Thr Gly Leu Asp Ala Pro Arg
                885                 890                 895

Asn Leu Arg Arg Val Ser Gln Thr Asp Asn Ser Ile Thr Leu Glu Trp
            900                 905                 910

Arg Asn Gly Lys Ala Ala Ile Asp Ser Tyr Arg Ile Lys Tyr Ala Pro
            915                 920                 925

Ile Ser Gly Gly Asp His Ala Glu Val Asp Val Pro Lys Ser Gln Gln
930                 935                 940

Ala Thr Thr Lys Thr Thr Leu Thr Gly Leu Arg Pro Gly Thr Glu Tyr
945                 950                 955                 960

Gly Ile Gly Val Ser Ala Val Lys Glu Asp Lys Glu Ser Asn Pro Ala
                965                 970                 975

Thr Ile Asn Ala Ala Thr Glu Leu Asp Thr Pro Lys Asp Leu Gln Val
                980                 985                 990

Ser Glu Thr Ala Glu Thr Ser Leu Thr Leu Leu Trp Lys Thr Pro Leu
            995                 1000                1005
```

-continued

```
Ala Lys Phe Asp Arg Tyr Arg Leu Asn Tyr Ser Leu Pro Thr Gly Gln
    1010                1015                1020

Trp Val Gly Val Gln Leu Pro Arg Asn Thr Thr Ser Tyr Val Leu Arg
1025                1030                1035                1040

Gly Leu Glu Pro Gly Gln Glu Tyr Asn Val Leu Leu Thr Ala Glu Lys
                1045                1050                1055

Gly Arg His Lys Ser Lys Pro Ala Arg Val Lys Ala Ser Thr Glu Gln
                1060                1065                1070

Ala Pro Glu Leu Glu Asn Leu Thr Val Thr Glu Val Gly Trp Asp Gly
            1075                1080                1085

Leu Arg Leu Asn Trp Thr Ala Ala Asp Gln Ala Tyr Glu His Phe Ile
            1090                1095                1100

Ile Gln Val Gln Glu Ala Asn Lys Val Glu Ala Ala Arg Asn Leu Thr
1105                1110                1115                1120

Val Pro Gly Ser Leu Arg Ala Val Asp Ile Pro Gly Leu Lys Ala Ala
                1125                1130                1135

Thr Pro Tyr Thr Val Ser Ile Tyr Gly Val Ile Gln Gly Tyr Arg Thr
                1140                1145                1150

Pro Val Leu Ser Ala Glu Ala Ser Thr Gly Glu Thr Pro Asn Leu Gly
            1155                1160                1165

Glu Val Val Val Ala Glu Val Gly Trp Asp Ala Leu Lys Leu Asn Trp
    1170                1175                1180

Thr Ala Pro Glu Gly Ala Tyr Glu Tyr Phe Phe Ile Gln Val Gln Glu
1185                1190                1195                1200

Ala Asp Thr Val Glu Ala Ala Gln Asn Leu Thr Val Pro Gly Gly Leu
                1205                1210                1215

Arg Ser Thr Asp Leu Pro Gly Leu Lys Ala Ala Thr His Tyr Thr Ile
            1220                1225                1230

Thr Ile Arg Gly Val Thr Gln Asp Phe Ser Thr Thr Pro Leu Ser Val
            1235                1240                1245

Glu Val Leu Thr Glu Glu Val Pro Asp Met Gly Asn Leu Thr Val Thr
    1250                1255                1260

Glu Val Ser Trp Asp Ala Leu Arg Leu Asn Trp Thr Thr Pro Asp Gly
1265                1270                1275                1280

Thr Tyr Asp Gln Phe Thr Ile Gln Val Gln Glu Ala Asp Gln Val Glu
                1285                1290                1295

Glu Ala His Asn Leu Thr Val Pro Gly Ser Leu Arg Ser Met Glu Ile
                1300                1305                1310

Pro Gly Leu Arg Ala Gly Thr Pro Tyr Thr Val Thr Leu His Gly Glu
            1315                1320                1325

Val Arg Gly His Ser Thr Arg Pro Leu Ala Val Glu Val Val Thr Glu
    1330                1335                1340

Asp Leu Pro Gln Leu Gly Asp Leu Ala Val Ser Glu Val Gly Trp Asp
1345                1350                1355                1360

Gly Leu Arg Leu Asn Trp Thr Ala Ala Asp Asn Ala Tyr Glu His Phe
                1365                1370                1375

Val Ile Gln Val Gln Glu Val Asn Lys Val Glu Ala Ala Gln Asn Leu
                1380                1385                1390

Thr Leu Pro Gly Ser Leu Arg Ala Val Asp Ile Pro Gly Leu Glu Ala
            1395                1400                1405

Ala Thr Pro Tyr Arg Val Ser Ile Tyr Gly Val Ile Arg Gly Tyr Arg
    1410                1415                1420

Thr Pro Val Leu Ser Ala Glu Ala Ser Thr Ala Lys Glu Pro Glu Ile
```

-continued

```
1425                1430                1435                1440

Gly Asn Leu Asn Val Ser Asp Ile Thr Pro Glu Ser Phe Asn Leu Ser
                1445                1450                1455

Trp Met Ala Thr Asp Gly Ile Phe Glu Thr Phe Thr Ile Glu Ile Ile
            1460                1465                1470

Asp Ser Asn Arg Leu Leu Glu Thr Val Glu Tyr Asn Ile Ser Gly Ala
        1475                1480                1485

Glu Arg Thr Ala His Ile Ser Gly Leu Pro Pro Ser Thr Asp Phe Ile
    1490                1495                1500

Val Tyr Leu Ser Gly Leu Ala Pro Ser Ile Arg Thr Lys Thr Ile Ser
1505                1510                1515                1520

Ala Thr Ala Thr Thr Glu Ala Leu Pro Leu Leu Glu Asn Leu Thr Ile
                1525                1530                1535

Ser Asp Ile Asn Pro Tyr Gly Phe Thr Val Ser Trp Met Ala Ser Glu
            1540                1545                1550

Asn Ala Phe Asp Ser Phe Leu Val Thr Val Val Asp Ser Gly Lys Leu
        1555                1560                1565

Leu Asp Pro Gln Glu Phe Thr Leu Ser Gly Thr Gln Arg Lys Leu Glu
    1570                1575                1580

Leu Arg Gly Leu Ile Thr Gly Ile Gly Tyr Glu Val Met Val Ser Gly
1585                1590                1595                1600

Phe Thr Gln Gly His Gln Thr Lys Pro Leu Arg Ala Glu Ile Val Thr
                1605                1610                1615

Glu Ala Glu Pro Glu Val Asp Asn Leu Leu Val Ser Asp Ala Thr Pro
            1620                1625                1630

Asp Gly Phe Arg Leu Ser Trp Thr Ala Asp Glu Gly Val Phe Asp Asn
        1635                1640                1645

Phe Val Leu Lys Ile Arg Asp Thr Lys Lys Gln Ser Glu Pro Leu Glu
    1650                1655                1660

Ile Thr Leu Leu Ala Pro Glu Arg Thr Arg Asp Ile Thr Gly Leu Arg
1665                1670                1675                1680

Glu Ala Thr Glu Tyr Glu Ile Glu Leu Tyr Gly Ile Ser Lys Gly Arg
                1685                1690                1695

Arg Ser Gln Thr Val Ser Ala Ile Ala Thr Thr Ala Met Gly Ser Pro
            1700                1705                1710

Lys Glu Val Ile Phe Ser Asp Ile Thr Glu Asn Ser Ala Thr Val Ser
        1715                1720                1725

Trp Arg Ala Pro Thr Ala Gln Val Glu Ser Phe Arg Ile Thr Tyr Val
    1730                1735                1740

Pro Ile Thr Gly Gly Thr Pro Ser Met Val Thr Val Asp Gly Thr Lys
1745                1750                1755                1760

Thr Gln Thr Arg Leu Val Lys Leu Ile Pro Gly Val Glu Tyr Leu Val
                1765                1770                1775

Ser Ile Ile Ala Met Lys Gly Phe Glu Glu Ser Glu Pro Val Ser Gly
            1780                1785                1790

Ser Phe Thr Thr Ala Leu Asp Gly Pro Ser Gly Leu Val Thr Ala Asn
        1795                1800                1805

Ile Thr Asp Ser Glu Ala Leu Ala Arg Trp Gln Pro Ala Ile Ala Thr
    1810                1815                1820

Val Asp Ser Tyr Val Ile Ser Tyr Thr Gly Glu Lys Val Pro Glu Ile
1825                1830                1835                1840

Thr Arg Thr Val Ser Gly Asn Thr Val Glu Tyr Ala Leu Thr Asp Leu
                1845                1850                1855
```

Glu Pro Ala Thr Glu Tyr Thr Leu Arg Ile Phe Ala Glu Lys Gly Pro
          1860                1865                1870

Gln Lys Ser Ser Thr Ile Thr Ala Lys Phe Thr Thr Asp Leu Asp Ser
    1875                1880                1885

Pro Arg Asp Leu Thr Ala Thr Glu Val Gln Ser Glu Thr Ala Leu Leu
    1890                1895                1900

Thr Trp Arg Pro Pro Arg Ala Ser Val Thr Gly Tyr Leu Leu Val Tyr
1905                1910                1915                1920

Glu Ser Val Asp Gly Thr Val Lys Glu Val Ile Val Gly Pro Asp Thr
            1925                1930                1935

Thr Ser Tyr Ser Leu Ala Asp Leu Ser Pro Ser Thr His Tyr Thr Ala
        1940                1945                1950

Lys Ile Gln Ala Leu Asn Gly Pro Leu Arg Ser Asn Met Ile Gln Thr
        1955                1960                1965

Ile Phe Thr Thr Ile Gly Leu Leu Tyr Pro Phe Pro Lys Asp Cys Ser
    1970                1975                1980

Gln Ala Met Leu Asn Gly Asp Thr Thr Ser Gly Leu Tyr Thr Ile Tyr
1985                1990                1995                2000

Leu Asn Gly Asp Lys Ala Gln Ala Leu Glu Val Phe Cys Asp Met Thr
            2005                2010                2015

Ser Asp Gly Gly Gly Trp Ile Val Phe Leu Arg Arg Lys Asn Gly Arg
        2020                2025                2030

Glu Asn Phe Tyr Gln Asn Trp Lys Ala Tyr Ala Ala Gly Phe Gly Asp
        2035                2040                2045

Arg Arg Glu Glu Phe Trp Leu Gly Leu Asp Asn Leu Asn Lys Ile Thr
    2050                2055                2060

Ala Gln Gly Gln Tyr Glu Leu Arg Val Asp Leu Arg Asp His Gly Glu
2065                2070                2075                2080

Thr Ala Phe Ala Val Tyr Asp Lys Phe Ser Val Gly Asp Ala Lys Thr
            2085                2090                2095

Arg Tyr Lys Leu Lys Val Glu Gly Tyr Ser Gly Thr Ala Gly Asp Ser
        2100                2105                2110

Met Ala Tyr His Asn Gly Arg Ser Phe Ser Thr Phe Asp Lys Asp Thr
        2115                2120                2125

Asp Ser Ala Ile Thr Asn Cys Ala Leu Ser Thr Arg Gly Phe Trp Tyr
    2130                2135                2140

Arg Asn Cys His Arg Val Asn Leu Met Gly Arg Tyr Gly Asp Asn Asn
2145                2150                2155                2160

His Ser Gln Gly Val Asn Trp Phe His Trp Lys Gly His Glu His Ser
            2165                2170                2175

Ile Gln Phe Ala Glu Met Lys Leu Arg Pro Ser Asn Phe Arg Asn Leu
        2180                2185                2190

Glu Gly Arg Arg Lys Arg Ala
        2195

<210> SEQ ID NO 3
<211> LENGTH: 6049
<212> TYPE: DNA
<213> ORGANISM: Gallus gallus
<220> FEATURE:
<221> NAME/KEY: CDS
<222> LOCATION: (309)..(5741)

<400> SEQUENCE: 3
cggctgatct gaccagtgtg ccgcactgtc aaaccctcct ttcacacacg cgcgcaccaa      60

-continued

```
atgagacggc acaacttctc tgagttttga caggacggcg aggaatccgg gagccgacag    120
ctgctgctgc agtacctctg cttcgtggag gctgcccgtg gcaggatctg atccgtcagc    180
ccacacgaga ataagcgtgc caagaaagga aggaaactc aacttagttt gaactggctc     240
tcaaatttct ccctccagtc tacaaaggcc aaacaaatat aagactccat cagctttgaa    300 gcactaca atg gga ctc cct tcc cag gtt ttg gcc tgt gcc atc tta ggt    350
         Met Gly Leu Pro Ser Gln Val Leu Ala Cys Ala Ile Leu Gly
           1               5                   10 ttg ctg tac cag cat gcc agt ggt ggg ctc atc aag cga att atc cgg    398
Leu Leu Tyr Gln His Ala Ser Gly Gly Leu Ile Lys Arg Ile Ile Arg
 15              20                  25                  30 cag aag agg gag act ggg ctc aat gtg acc tta cca gag gat aat cag    446
Gln Lys Arg Glu Thr Gly Leu Asn Val Thr Leu Pro Glu Asp Asn Gln
                 35                  40                  45 cct gtg gtt ttc aat cat gtc tac aac atc aag ctg cct gtt ggc tcc    494
Pro Val Val Phe Asn His Val Tyr Asn Ile Lys Leu Pro Val Gly Ser
                 50                  55                  60 ctt tgc tct gtg gac ctg gac aca gca agc ggg gac gca gac ctg aag    542
Leu Cys Ser Val Asp Leu Asp Thr Ala Ser Gly Asp Ala Asp Leu Lys
         65                  70                  75 gca gaa att gag cct gtc aag aat tac gag gag cat acg gtg aat gag    590
Ala Glu Ile Glu Pro Val Lys Asn Tyr Glu Glu His Thr Val Asn Glu
 80                  85                  90 ggg aac cag att gtc ttc acg cac cgc atc aac att ccc cgc cgg gcc    638
Gly Asn Gln Ile Val Phe Thr His Arg Ile Asn Ile Pro Arg Arg Ala
 95                 100                 105                 110 tgt ggc tgt gcg gct gcc cca gac atc aag gac ctg ctg agc aga ctg    686
Cys Gly Cys Ala Ala Ala Pro Asp Ile Lys Asp Leu Leu Ser Arg Leu
                115                 120                 125 gag gag ctg gag ggg ctg gta tcc tcc ctc cgg gag cag tgt gcc agc    734
Glu Glu Leu Glu Gly Leu Val Ser Ser Leu Arg Glu Gln Cys Ala Ser
            130                 135                 140 ggg gct gga tgc tgt cct aat tcc cag aca gca gaa ggt cgc ctg gac    782
Gly Ala Gly Cys Cys Pro Asn Ser Gln Thr Ala Glu Gly Arg Leu Asp
        145                 150                 155 acg gcc ccc tat tgc agt ggg cac ggc aac tac agc acc gag atc tgt    830
Thr Ala Pro Tyr Cys Ser Gly His Gly Asn Tyr Ser Thr Glu Ile Cys
    160                 165                 170 ggc tgc gtg tgc gag cca ggc tgg aaa ggc ccc aac tgc tcc gaa ccg    878
Gly Cys Val Cys Glu Pro Gly Trp Lys Gly Pro Asn Cys Ser Glu Pro
175                 180                 185                 190 gcc tgc cca cgc aac tgc ctc aac cgc ggc ctc tgc gtg cgg gca aag    926
Ala Cys Pro Arg Asn Cys Leu Asn Arg Gly Leu Cys Val Arg Ala Lys
                195                 200                 205 tgc atc tgc gag gag ggc ttt acc ggc gag gac tgc agc cag gct cgc    974
Cys Ile Cys Glu Glu Gly Phe Thr Gly Glu Asp Cys Ser Gln Ala Arg
            210                 215                 220 tgc ccg tct gac tgc aac gac caa ggc aag tgt gtg gat ggg gtg tgc   1022
Cys Pro Ser Asp Cys Asn Asp Gln Gly Lys Cys Val Asp Gly Val Cys
        225                 230                 235 gtc tgc ttc gag ggc tac acg ggc ccg gac tgc ggc gag gag ctc tgc   1070
Val Cys Phe Glu Gly Tyr Thr Gly Pro Asp Cys Gly Glu Glu Leu Cys
    240                 245                 250 ccc cac ggg tgt ggc att cac ggg cgc tgt gtg ggt gga cgc tgt gtg   1118
Pro His Gly Cys Gly Ile His Gly Arg Cys Val Gly Gly Arg Cys Val
255                 260                 265                 270 tgc cac gag ggc ttc act ggc gag gac tgc aat gag ccc ctg tgc ccc   1166
Cys His Glu Gly Phe Thr Gly Glu Asp Cys Asn Glu Pro Leu Cys Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 275 |     |     |     |     | 280 |     |     |     |     | 285 |     |     |      |
| aac | aac | tgt | cac | aac | cgc | ggg | cgc | tgt | gtg | gac | aac | gag | tgc | gtc | tgc | 1214 |
| Asn | Asn | Cys | His | Asn | Arg | Gly | Arg | Cys | Val | Asp | Asn | Glu | Cys | Val | Cys |      |
|     |     |     | 290 |     |     |     |     | 295 |     |     |     |     | 300 |     |     |      |
| gat | gag | ggc | tac | acg | gga | gag | gac | tgc | ggc | gag | ctg | att | tgc | ccc | aat | 1262 |
| Asp | Glu | Gly | Tyr | Thr | Gly | Glu | Asp | Cys | Gly | Glu | Leu | Ile | Cys | Pro | Asn |      |
|     |     | 305 |     |     |     |     | 310 |     |     |     |     | 315 |     |     |     |      |
| gac | tgc | ttt | gac | cgc | ggg | cgc | tgc | atc | aat | ggg | acc | tgc | ttc | tgc | gag | 1310 |
| Asp | Cys | Phe | Asp | Arg | Gly | Arg | Cys | Ile | Asn | Gly | Thr | Cys | Phe | Cys | Glu |      |
|     | 320 |     |     |     |     | 325 |     |     |     |     | 330 |     |     |     |     |      |
| gag | ggc | tac | act | gga | gag | gac | tgc | ggc | gag | ctg | acc | tgc | ccc | aac | aac | 1358 |
| Glu | Gly | Tyr | Thr | Gly | Glu | Asp | Cys | Gly | Glu | Leu | Thr | Cys | Pro | Asn | Asn |      |
| 335 |     |     |     |     | 340 |     |     |     |     | 345 |     |     |     |     | 350 |      |
| tgc | aac | ggc | aac | ggg | cgc | tgt | gag | aac | ggg | ctg | tgt | gtg | tgc | cat | gag | 1406 |
| Cys | Asn | Gly | Asn | Gly | Arg | Cys | Glu | Asn | Gly | Leu | Cys | Val | Cys | His | Glu |      |
|     |     |     | 355 |     |     |     |     | 360 |     |     |     |     | 365 |     |     |      |
| ggc | ttc | gtg | ggg | gat | gac | tgc | agc | cag | aag | agg | tgc | ccg | aag | acg | tgc | 1454 |
| Gly | Phe | Val | Gly | Asp | Asp | Cys | Ser | Gln | Lys | Arg | Cys | Pro | Lys | Thr | Cys |      |
|     |     | 370 |     |     |     |     | 375 |     |     |     |     | 380 |     |     |     |      |
| aat | aac | cgc | ggg | cgc | tgc | gtg | gat | ggg | cgc | tgt | gtg | tgc | cat | gag | ggg | 1502 |
| Asn | Asn | Arg | Gly | Arg | Cys | Val | Asp | Gly | Arg | Cys | Val | Cys | His | Glu | Gly |      |
|     | 385 |     |     |     |     | 390 |     |     |     |     | 395 |     |     |     |     |      |
| tac | ctg | ggg | gag | gac | tgt | ggg | gag | ctg | cgg | tgc | ccc | aac | gac | tgc | cac | 1550 |
| Tyr | Leu | Gly | Glu | Asp | Cys | Gly | Glu | Leu | Arg | Cys | Pro | Asn | Asp | Cys | His |      |
| 400 |     |     |     |     | 405 |     |     |     |     | 410 |     |     |     |     |     |      |
| aac | cgc | ggg | cgc | tgc | atc | aac | ggg | cag | tgt | gtg | tgt | gat | gag | gga | ttc | 1598 |
| Asn | Arg | Gly | Arg | Cys | Ile | Asn | Gly | Gln | Cys | Val | Cys | Asp | Glu | Gly | Phe |      |
| 415 |     |     |     |     | 420 |     |     |     |     | 425 |     |     |     |     | 430 |      |
| att | ggg | gag | gac | tgt | gga | gag | ctg | cgg | tgc | ccc | aac | gac | tgc | cag | caa | 1646 |
| Ile | Gly | Glu | Asp | Cys | Gly | Glu | Leu | Arg | Cys | Pro | Asn | Asp | Cys | Gln | Gln |      |
|     |     |     | 435 |     |     |     |     | 440 |     |     |     |     | 445 |     |     |      |
| cgc | ggg | cgc | tgc | atc | aat | ggg | cag | tgc | gag | tgc | cac | gag | gga | ttc | atc | 1694 |
| Arg | Gly | Arg | Cys | Ile | Asn | Gly | Gln | Cys | Glu | Cys | His | Glu | Gly | Phe | Ile |      |
|     |     |     | 450 |     |     |     |     | 455 |     |     |     |     | 460 |     |     |      |
| ggg | gag | gac | tgc | ggg | gag | ctg | cgg | tgt | ccc | aac | gac | tgc | aac | agc | cat | 1742 |
| Gly | Glu | Asp | Cys | Gly | Glu | Leu | Arg | Cys | Pro | Asn | Asp | Cys | Asn | Ser | His |      |
|     |     | 465 |     |     |     |     | 470 |     |     |     |     | 475 |     |     |     |      |
| ggg | cgc | tgc | gtc | aat | ggg | cag | tgc | gtg | tgt | gat | gag | ggg | tac | aca | ggg | 1790 |
| Gly | Arg | Cys | Val | Asn | Gly | Gln | Cys | Val | Cys | Asp | Glu | Gly | Tyr | Thr | Gly |      |
|     | 480 |     |     |     |     | 485 |     |     |     |     | 490 |     |     |     |     |      |
| gag | gac | tgc | ggg | gag | ttg | cgg | tgc | ccc | aac | gac | tgc | cac | aac | cgc | ggg | 1838 |
| Glu | Asp | Cys | Gly | Glu | Leu | Arg | Cys | Pro | Asn | Asp | Cys | His | Asn | Arg | Gly |      |
| 495 |     |     |     |     | 500 |     |     |     |     | 505 |     |     |     |     | 510 |      |
| cgc | tgc | gtg | gag | gga | cgc | tgt | gtg | tgt | gac | aac | ggc | ttc | atg | ggg | gag | 1886 |
| Arg | Cys | Val | Glu | Gly | Arg | Cys | Val | Cys | Asp | Asn | Gly | Phe | Met | Gly | Glu |      |
|     |     |     | 515 |     |     |     |     | 520 |     |     |     |     | 525 |     |     |      |
| gac | tgc | ggg | gag | ctg | tcc | tgt | ccc | aat | gac | tgc | cac | cag | cac | ggg | cgc | 1934 |
| Asp | Cys | Gly | Glu | Leu | Ser | Cys | Pro | Asn | Asp | Cys | His | Gln | His | Gly | Arg |      |
|     |     | 530 |     |     |     |     | 535 |     |     |     |     | 540 |     |     |     |      |
| tgc | gtc | gat | ggg | cgc | tgc | gtg | tgc | cac | gag | ggc | ttc | act | ggg | gaa | gac | 1982 |
| Cys | Val | Asp | Gly | Arg | Cys | Val | Cys | His | Glu | Gly | Phe | Thr | Gly | Glu | Asp |      |
|     | 545 |     |     |     |     | 550 |     |     |     |     | 555 |     |     |     |     |      |
| tgc | cgg | gaa | cgg | tcc | tgc | ccc | aat | gac | tgc | aac | aac | gtg | ggc | cgc | tgt | 2030 |
| Cys | Arg | Glu | Arg | Ser | Cys | Pro | Asn | Asp | Cys | Asn | Asn | Val | Gly | Arg | Cys |      |
|     |     |     | 560 |     |     |     |     | 565 |     |     |     |     | 570 |     |     |      |
| gtc | gag | gga | cgg | tgt | gtc | tgt | gag | gaa | ggt | tac | atg | ggg | atc | gac | tgt | 2078 |
| Val | Glu | Gly | Arg | Cys | Val | Cys | Glu | Glu | Gly | Tyr | Met | Gly | Ile | Asp | Cys |      |
| 575 |     |     |     |     | 580 |     |     |     |     | 585 |     |     |     |     | 590 |      |
| tct | gat | gtg | tct | cct | cca | acg | gga | ctg | act | gta | acg | aat | gta | aca | gat | 2126 |

```
                                                                      -continued Ser Asp Val Ser Pro Pro Thr Gly Leu Thr Val Thr Asn Val Thr Asp
                    595                 600                 605 aaa acg gta aat ctg gaa tgg aag cat gag aat ctc gtc aat gag tac        2174
Lys Thr Val Asn Leu Glu Trp Lys His Glu Asn Leu Val Asn Glu Tyr
            610                 615                 620 ctt gtc acc tat gtc cct acc agc agt ggt ggc tta gat cta cag ttc        2222
Leu Val Thr Tyr Val Pro Thr Ser Ser Gly Gly Leu Asp Leu Gln Phe
        625                 630                 635 acc gta cca gga aac cag aca tct gcc act att cat gag ctg gag cct        2270
Thr Val Pro Gly Asn Gln Thr Ser Ala Thr Ile His Glu Leu Glu Pro
    640                 645                 650 ggt gtg gaa tac ttc atc cgt gtc ttt gca atc ctt aaa aac aag aaa        2318
Gly Val Glu Tyr Phe Ile Arg Val Phe Ala Ile Leu Lys Asn Lys Lys
655                 660                 665                 670 agt att cca gtc agt gcc aga gta gcg aca tat ttg cct gct cca gaa        2366
Ser Ile Pro Val Ser Ala Arg Val Ala Thr Tyr Leu Pro Ala Pro Glu
                675                 680                 685 ggt ctg aaa ttc aaa tct gtt aga gaa acg tct gtc cag gtg gaa tgg        2414
Gly Leu Lys Phe Lys Ser Val Arg Glu Thr Ser Val Gln Val Glu Trp
            690                 695                 700 gat cct ctg agc att tcc ttt gat ggc tgg gag ctg gtc ttt cgt aat        2462
Asp Pro Leu Ser Ile Ser Phe Asp Gly Trp Glu Leu Val Phe Arg Asn
        705                 710                 715 atg cag aaa aag gat gat aat gga gac ata acc agc agc ttg aaa agg        2510
Met Gln Lys Lys Asp Asp Asn Gly Asp Ile Thr Ser Ser Leu Lys Arg
    720                 725                 730 ccg gag aca tca tat atg cag cca gga ttg gca cca gga caa cag tat        2558
Pro Glu Thr Ser Tyr Met Gln Pro Gly Leu Ala Pro Gly Gln Gln Tyr
735                 740                 745                 750 aat gta tcc ctt cat ata gtg aaa aac aat acc aga gga cca ggg cta        2606
Asn Val Ser Leu His Ile Val Lys Asn Asn Thr Arg Gly Pro Gly Leu
                755                 760                 765 tcc cga gtg ata acc aca aaa ctc gat gcc cct agc cag att gag gcg        2654
Ser Arg Val Ile Thr Thr Lys Leu Asp Ala Pro Ser Gln Ile Glu Ala
            770                 775                 780 aaa gat gtc aca gac acc aca gct ctg atc aca tgg tcc aaa ccc ttg        2702
Lys Asp Val Thr Asp Thr Thr Ala Leu Ile Thr Trp Ser Lys Pro Leu
        785                 790                 795 gct gaa att gaa ggc ata gag ctc aca tat ggc ccc aag gat gtt cca        2750
Ala Glu Ile Glu Gly Ile Glu Leu Thr Tyr Gly Pro Lys Asp Val Pro
    800                 805                 810 ggg gac agg act acc att gac ctc tct gag gat gaa aac caa tat tct        2798
Gly Asp Arg Thr Thr Ile Asp Leu Ser Glu Asp Glu Asn Gln Tyr Ser
815                 820                 825                 830 att gga aac ctg agg cca cac aca gaa tat gaa tat gaa gtg aca ctc        2846
Ile Gly Asn Leu Arg Pro His Thr Glu Tyr Glu Tyr Glu Val Thr Leu
                835                 840                 845 att tct cgg cga ggg gac atg gag agt gac cct gca aaa gaa gtc ttt        2894
Ile Ser Arg Arg Gly Asp Met Glu Ser Asp Pro Ala Lys Glu Val Phe
            850                 855                 860 gtc aca gac ttg gat gct cca cga aac ctg aag cga gtg tca cag aca        2942
Val Thr Asp Leu Asp Ala Pro Arg Asn Leu Lys Arg Val Ser Gln Thr
        865                 870                 875 gac aac agc att act ttg gag tgg aag ttc agc cat gca aat att gat        2990
Asp Asn Ser Ile Thr Leu Glu Trp Lys Phe Ser His Ala Asn Ile Asp
    880                 885                 890 aat tac cga att aag ttt gct ccc att tct ggt gga gac cac act gag        3038
Asn Tyr Arg Ile Lys Phe Ala Pro Ile Ser Gly Gly Asp His Thr Glu
895                 900                 905                 910
```

```
ctg aca gtg cca aag ggc aac caa gca aca acc aga gct aca ctc aca   3086
Leu Thr Val Pro Lys Gly Asn Gln Ala Thr Thr Arg Ala Thr Leu Thr
            915                 920                 925 ggt ttg aga cct gga act gaa tat ggc att gga gtg aca gca gtg aga   3134
Gly Leu Arg Pro Gly Thr Glu Tyr Gly Ile Gly Val Thr Ala Val Arg
        930                 935                 940 cag gac agg gaa agt gct cct gct acc att aat gct ggc act gat ctt   3182
Gln Asp Arg Glu Ser Ala Pro Ala Thr Ile Asn Ala Gly Thr Asp Leu
    945                 950                 955 gat aac ccc aag gac ttg gaa gtc agt gac ccc act gaa acc acc ctg   3230
Asp Asn Pro Lys Asp Leu Glu Val Ser Asp Pro Thr Glu Thr Thr Leu
960                 965                 970 tcc ctt cgc tgg aga aga cca gtg gcc aaa ttt gat cgt tac cgc ctc   3278
Ser Leu Arg Trp Arg Arg Pro Val Ala Lys Phe Asp Arg Tyr Arg Leu
975                 980                 985                 990 act tac gtt agc ccc tct gga aag aag aac gaa atg gag atc cct gtg   3326
Thr Tyr Val Ser Pro Ser Gly Lys Lys Asn Glu Met Glu Ile Pro Val
            995                 1000                1005 gac agc acc tct ttt atc ctg aga gga tta gac gca ggg acg gag tac   3374
Asp Ser Thr Ser Phe Ile Leu Arg Gly Leu Asp Ala Gly Thr Glu Tyr
        1010                1015                1020 acc atc agt cta gtg gca gag aaa ggc aga cac aaa agc aaa ccc aca   3422
Thr Ile Ser Leu Val Ala Glu Lys Gly Arg His Lys Ser Lys Pro Thr
    1025                1030                1035 acc atc aag ggt tcg act gag gaa gaa cct gag ctt gga aac tta tca   3470
Thr Ile Lys Gly Ser Thr Glu Glu Glu Pro Glu Leu Gly Asn Leu Ser
1040                1045                1050 gtg tca gag act ggc tgg gat ggt ttc cag ctc acc tgg aca gca gcc   3518
Val Ser Glu Thr Gly Trp Asp Gly Phe Gln Leu Thr Trp Thr Ala Ala
1055                1060                1065                1070 gac ggg gcc tat gag aac ttt gtc att cag gtg cag cag tct gac aat   3566
Asp Gly Ala Tyr Glu Asn Phe Val Ile Gln Val Gln Gln Ser Asp Asn
        1075                1080                1085 cca gaa gaa acc tgg aac att aca gtc ccc ggc gga cag cac tct gtg   3614
Pro Glu Glu Thr Trp Asn Ile Thr Val Pro Gly Gly Gln His Ser Val
    1090                1095                1100 aac gtt aca ggc ctc aag gcc aac aca cct tat aac gtc aca ctt tac   3662
Asn Val Thr Gly Leu Lys Ala Asn Thr Pro Tyr Asn Val Thr Leu Tyr
1105                1110                1115 ggt gtg att cga ggc tac aga acc aaa ccc ctt tat gtt gaa acc acg   3710
Gly Val Ile Arg Gly Tyr Arg Thr Lys Pro Leu Tyr Val Glu Thr Thr
        1120                1125                1130 aca gga gca cac ccc gaa gtt ggt gag cta acc gtt tcc gac att act   3758
Thr Gly Ala His Pro Glu Val Gly Glu Leu Thr Val Ser Asp Ile Thr
1135                1140                1145                1150 cct gaa agc ttc aac ctt tct tgg acg acc acc aac ggg gac ttt gac   3806
Pro Glu Ser Phe Asn Leu Ser Trp Thr Thr Thr Asn Gly Asp Phe Asp
        1155                1160                1165 gcc ttt act att gaa att att gat tct aac agg ttg ctg gag ccc atg   3854
Ala Phe Thr Ile Glu Ile Ile Asp Ser Asn Arg Leu Leu Glu Pro Met
    1170                1175                1180 gag ttc aac atc tca ggc aat tca aga aca gct cat atc tca ggg ctt   3902
Glu Phe Asn Ile Ser Gly Asn Ser Arg Thr Ala His Ile Ser Gly Leu
            1185                1190                1195 tcc ccc agc act gat ttt att gtc tac ctc tat ggg atc tct cat ggt   3950
Ser Pro Ser Thr Asp Phe Ile Val Tyr Leu Tyr Gly Ile Ser His Gly
    1200                1205                1210 ttc cgc aca cag gca ata agt gct gcg gct aca aca gag gca gaa ccc   3998
Phe Arg Thr Gln Ala Ile Ser Ala Ala Ala Thr Thr Glu Ala Glu Pro
1215                1220                1225                1230
```

```
gag gtg gac aac ctt ctg gtt tca gat gct acc cca gac ggc ttc cgt      4046
Glu Val Asp Asn Leu Leu Val Ser Asp Ala Thr Pro Asp Gly Phe Arg
             1235                1240                1245 ctg acc tgg act gca gat gat ggg gtt ttc gac agt ttt gtt cta aaa      4094
Leu Thr Trp Thr Ala Asp Asp Gly Val Phe Asp Ser Phe Val Leu Lys
             1250                1255                1260 atc agg gat acc aaa agg aaa tct gat cca ctg gaa ctc att gta cca      4142
Ile Arg Asp Thr Lys Arg Lys Ser Asp Pro Leu Glu Leu Ile Val Pro
             1265                1270                1275 ggc cat gag cgc acc cat gat ata aca ggg ctg aaa gag ggc act gag      4190
Gly His Glu Arg Thr His Asp Ile Thr Gly Leu Lys Glu Gly Thr Glu
             1280                1285                1290 tat gaa att gag ctc tat gga gtt agc agt gga cgg cgc tcc caa ccc      4238
Tyr Glu Ile Glu Leu Tyr Gly Val Ser Ser Gly Arg Arg Ser Gln Pro
1295                1300                1305                1310 ata aat tca gta gca acc aca gtt gtg gga tct ccc aag gga atc tct      4286
Ile Asn Ser Val Ala Thr Thr Val Val Gly Ser Pro Lys Gly Ile Ser
             1315                1320                1325 ttc tcg gac atc aca gaa aac tct gct aga gtc agc tgg aca ccc ccc      4334
Phe Ser Asp Ile Thr Glu Asn Ser Ala Arg Val Ser Trp Thr Pro Pro
             1330                1335                1340 cgc agc cgt gtg gat agc tac agg gtc tcc tat gtc ccc atc aca ggc      4382
Arg Ser Arg Val Asp Ser Tyr Arg Val Ser Tyr Val Pro Ile Thr Gly
             1345                1350                1355 ggc act ccc aat gtt gtt aca gtt gat gga agc aag aca agg aca aag      4430
Gly Thr Pro Asn Val Val Thr Val Asp Gly Ser Lys Thr Arg Thr Lys
             1360                1365                1370 ctg gtg aag tta gtc cca ggt gta gac tac aac gtt aat atc atc tct      4478
Leu Val Lys Leu Val Pro Gly Val Asp Tyr Asn Val Asn Ile Ile Ser
1375                1380                1385                1390 gtg aaa ggc ttt gaa gaa agc gaa ccc att tct gga att ctg aaa aca      4526
Val Lys Gly Phe Glu Glu Ser Glu Pro Ile Ser Gly Ile Leu Lys Thr
             1395                1400                1405 gct ctg gac agc ccg tca gga ctg gta gtg atg aac att aca gac tcg      4574
Ala Leu Asp Ser Pro Ser Gly Leu Val Val Met Asn Ile Thr Asp Ser
             1410                1415                1420 gag gct ctg gca acc tgg cag cct gca att gca gct gtg gat aat tac      4622
Glu Ala Leu Ala Thr Trp Gln Pro Ala Ile Ala Ala Val Asp Asn Tyr
             1425                1430                1435 att gtc tcc tac tct tct gag gat gag cca gaa gtt aca cag atg gta      4670
Ile Val Ser Tyr Ser Ser Glu Asp Glu Pro Glu Val Thr Gln Met Val
             1440                1445                1450 tca gga aac aca gtg gag tac gac ctg aat ggc ctt cga cct gcg aca      4718
Ser Gly Asn Thr Val Glu Tyr Asp Leu Asn Gly Leu Arg Pro Ala Thr
1455                1460                1465                1470 gag tac acc ctg agg gtg cat gca gtg aag gat gcg cag aag agc gag      4766
Glu Tyr Thr Leu Arg Val His Ala Val Lys Asp Ala Gln Lys Ser Glu
             1475                1480                1485 acc ctc tcc acc cag ttc act aca gga ctc gat gct cca aaa gat tta      4814
Thr Leu Ser Thr Gln Phe Thr Thr Gly Leu Asp Ala Pro Lys Asp Leu
             1490                1495                1500 agt gct acc gag gtt cag tca gaa aca gct gtg ata acg tgg agg cct      4862
Ser Ala Thr Glu Val Gln Ser Glu Thr Ala Val Ile Thr Trp Arg Pro
             1505                1510                1515 cca cgt gct cct gtc act gat tac ctc ctg acc tac gag tcc att gat      4910
Pro Arg Ala Pro Val Thr Asp Tyr Leu Leu Thr Tyr Glu Ser Ile Asp
             1520                1525                1530 ggc aga gtc aag gaa gtc atc cta gac cct gag acg acc tcc tac acc      4958
Gly Arg Val Lys Glu Val Ile Leu Asp Pro Glu Thr Thr Ser Tyr Thr
```

-continued

```
          1535                1540                1545                1550
ctg aca gag ctg agc cca tcc act caa tac aca gtg aaa ctt cag gca           5006
Leu Thr Glu Leu Ser Pro Ser Thr Gln Tyr Thr Val Lys Leu Gln Ala
              1555                1560                1565 ctg agc aga tct atg agg agc aaa atg atc cag act gtt ttc acc aca           5054
Leu Ser Arg Ser Met Arg Ser Lys Met Ile Gln Thr Val Phe Thr Thr
          1570                1575                1580 act ggt ctt ctt tat cct tat cct aaa gac tgc tcc caa gct ctc ctg           5102
Thr Gly Leu Leu Tyr Pro Tyr Pro Lys Asp Cys Ser Gln Ala Leu Leu
          1585                1590                1595 aat gga gag gtc acc tct ggg ctc tac act att tat ctg aat gga gac           5150
Asn Gly Glu Val Thr Ser Gly Leu Tyr Thr Ile Tyr Leu Asn Gly Asp
      1600                1605                1610 agg aca cag cct ctg caa gtc ttc tgt gac atg gct gaa gat gga ggc           5198
Arg Thr Gln Pro Leu Gln Val Phe Cys Asp Met Ala Glu Asp Gly Gly
  1615                1620                1625                1630 gga tgg att gtg ttc ctg agg cgt caa aat gga aag gaa gat ttc tac           5246
Gly Trp Ile Val Phe Leu Arg Arg Gln Asn Gly Lys Glu Asp Phe Tyr
              1635                1640                1645 agg aac tgg aag aat tac gtg gcc ggc ttt gga gat ccc aag gat gaa           5294
Arg Asn Trp Lys Asn Tyr Val Ala Gly Phe Gly Asp Pro Lys Asp Glu
          1650                1655                1660 ttc tgg ata ggt ctg gag aac ctc cac aaa atc agc tct cag ggg cag           5342
Phe Trp Ile Gly Leu Glu Asn Leu His Lys Ile Ser Ser Gln Gly Gln
          1665                1670                1675 tac gag ctg cgt gtg gat ctg aga gac aga ggt gag aca gcc tat gct           5390
Tyr Glu Leu Arg Val Asp Leu Arg Asp Arg Gly Glu Thr Ala Tyr Ala
      1680                1685                1690 gtg tac gac aag ttc agc gtt gga gat gcc aag acc cgg tac cgg ctg           5438
Val Tyr Asp Lys Phe Ser Val Gly Asp Ala Lys Thr Arg Tyr Arg Leu
1695                1700                1705                1710 agg gtg gat ggc tac agt ggc aca gca ggt gac tcc atg acc tac cat           5486
Arg Val Asp Gly Tyr Ser Gly Thr Ala Gly Asp Ser Met Thr Tyr His
              1715                1720                1725 aat gga aga tcc ttc tcc act ttt gac aag gac aat gat tct gct atc           5534
Asn Gly Arg Ser Phe Ser Thr Phe Asp Lys Asp Asn Asp Ser Ala Ile
          1730                1735                1740 acc aac tgt gct ttg tca tac aag ggt gct ttc tgg tac aag aat tgt           5582
Thr Asn Cys Ala Leu Ser Tyr Lys Gly Ala Phe Trp Tyr Lys Asn Cys
          1745                1750                1755 cac cga gtc aat ctg atg ggc aga tat ggt gac aac aac cac agt cag           5630
His Arg Val Asn Leu Met Gly Arg Tyr Gly Asp Asn Asn His Ser Gln
      1760                1765                1770 ggt gtt aat tgg ttc cac tgg aag ggc cac gaa tac tcc atc cag ttt           5678
Gly Val Asn Trp Phe His Trp Lys Gly His Glu Tyr Ser Ile Gln Phe
1775                1780                1785                1790 gca gag atg aaa ctg aga ccc tcc agc ttt cgg aat ctg gaa gga aga           5726
Ala Glu Met Lys Leu Arg Pro Ser Ser Phe Arg Asn Leu Glu Gly Arg
              1795                1800                1805 cga aag cga gca taa agccttggga tggtgaaagg gctacgggca gggcaacatg          5781
Arg Lys Arg Ala
          1810 gggagggaca gagagcgggg ggcatgggag gatctctggc atcactgggg ttatgggtgt         5841 gaggagctgg tagtcgtacc aaagcatcgc aacccttggc acaagagccc aaacaacgag         5901 ccttacgtgt cccagcaatt ccagcagagc agctccagct ctgcccactg ctgatgtcct         5961 tcacgccaaa gacaacgatc tcaagggttg tatgctgttt tcttcatttt tcttttctca         6021 gcctctggga tgaagttctt ccacggcg                                            6049
```

<210> SEQ ID NO 4
<211> LENGTH: 1810
<212> TYPE: PRT
<213> ORGANISM: Gallus gallus

<400> SEQUENCE: 4

Met Gly Leu Pro Ser Gln Val Leu Ala Cys Ala Ile Leu Gly Leu Leu
 1               5                  10                  15

Tyr Gln His Ala Ser Gly Gly Leu Ile Lys Arg Ile Ile Arg Gln Lys
            20                  25                  30

Arg Glu Thr Gly Leu Asn Val Thr Leu Pro Glu Asp Asn Gln Pro Val
        35                  40                  45

Val Phe Asn His Val Tyr Asn Ile Lys Leu Pro Val Gly Ser Leu Cys
    50                  55                  60

Ser Val Asp Leu Asp Thr Ala Ser Gly Asp Ala Asp Leu Lys Ala Glu
65                  70                  75                  80

Ile Glu Pro Val Lys Asn Tyr Glu Glu His Thr Val Asn Glu Gly Asn
                85                  90                  95

Gln Ile Val Phe Thr His Arg Ile Asn Ile Pro Arg Arg Ala Cys Gly
            100                 105                 110

Cys Ala Ala Ala Pro Asp Ile Lys Asp Leu Leu Ser Arg Leu Glu Glu
        115                 120                 125

Leu Glu Gly Leu Val Ser Ser Leu Arg Glu Gln Cys Ala Ser Gly Ala
    130                 135                 140

Gly Cys Cys Pro Asn Ser Gln Thr Ala Glu Gly Arg Leu Asp Thr Ala
145                 150                 155                 160

Pro Tyr Cys Ser Gly His Gly Asn Tyr Ser Thr Glu Ile Cys Gly Cys
                165                 170                 175

Val Cys Glu Pro Gly Trp Lys Gly Pro Asn Cys Ser Glu Pro Ala Cys
            180                 185                 190

Pro Arg Asn Cys Leu Asn Arg Gly Leu Cys Val Arg Ala Lys Cys Ile
        195                 200                 205

Cys Glu Glu Gly Phe Thr Gly Glu Asp Cys Ser Gln Ala Arg Cys Pro
    210                 215                 220

Ser Asp Cys Asn Asp Gln Gly Lys Cys Val Asp Gly Val Cys Val Cys
225                 230                 235                 240

Phe Glu Gly Tyr Thr Gly Pro Asp Cys Gly Glu Glu Leu Cys Pro His
                245                 250                 255

Gly Cys Gly Ile His Gly Arg Cys Val Gly Gly Arg Cys Val Cys His
            260                 265                 270

Glu Gly Phe Thr Gly Glu Asp Cys Asn Glu Pro Leu Cys Pro Asn Asn
        275                 280                 285

Cys His Asn Arg Gly Arg Cys Val Asp Asn Glu Cys Val Cys Asp Glu
    290                 295                 300

Gly Tyr Thr Gly Glu Asp Cys Gly Glu Leu Ile Cys Pro Asn Asp Cys
305                 310                 315                 320

Phe Asp Arg Gly Arg Cys Ile Asn Gly Thr Cys Phe Cys Glu Glu Gly
                325                 330                 335

Tyr Thr Gly Glu Asp Cys Gly Glu Leu Thr Cys Pro Asn Asn Cys Asn
            340                 345                 350

Gly Asn Gly Arg Cys Glu Asn Gly Leu Cys Val Cys His Glu Gly Phe
        355                 360                 365

Val Gly Asp Asp Cys Ser Gln Lys Arg Cys Pro Lys Thr Cys Asn Asn

```
        370             375             380
Arg Gly Arg Cys Val Asp Gly Arg Cys Val Cys His Glu Gly Tyr Leu
385             390             395             400

Gly Glu Asp Cys Gly Glu Leu Arg Cys Pro Asn Asp Cys His Asn Arg
                405             410             415

Gly Arg Cys Ile Asn Gly Gln Cys Val Cys Asp Glu Gly Phe Ile Gly
                420             425             430

Glu Asp Cys Gly Glu Leu Arg Cys Pro Asn Asp Cys Gln Gln Arg Gly
                435             440             445

Arg Cys Ile Asn Gly Gln Cys Glu Cys His Glu Gly Phe Ile Gly Glu
                450             455             460

Asp Cys Gly Glu Leu Arg Cys Pro Asn Asp Cys Asn Ser His Gly Arg
465             470             475             480

Cys Val Asn Gly Gln Cys Val Cys Asp Glu Gly Tyr Thr Gly Glu Asp
                485             490             495

Cys Gly Glu Leu Arg Cys Pro Asn Asp Cys His Asn Arg Gly Arg Cys
                500             505             510

Val Glu Gly Arg Cys Val Cys Asp Asn Gly Phe Met Gly Glu Asp Cys
                515             520             525

Gly Glu Leu Ser Cys Pro Asn Asp Cys His Gln His Gly Arg Cys Val
530             535             540

Asp Gly Arg Cys Val Cys His Glu Gly Phe Thr Gly Glu Asp Cys Arg
545             550             555             560

Glu Arg Ser Cys Pro Asn Asp Cys Asn Asn Val Gly Arg Cys Val Glu
                565             570             575

Gly Arg Cys Val Cys Glu Glu Gly Tyr Met Gly Ile Asp Cys Ser Asp
                580             585             590

Val Ser Pro Pro Thr Gly Leu Thr Val Thr Asn Val Thr Asp Lys Thr
                595             600             605

Val Asn Leu Glu Trp Lys His Glu Asn Leu Val Asn Glu Tyr Leu Val
610             615             620

Thr Tyr Val Pro Thr Ser Ser Gly Gly Leu Asp Leu Gln Phe Thr Val
625             630             635             640

Pro Gly Asn Gln Thr Ser Ala Thr Ile His Glu Leu Glu Pro Gly Val
                645             650             655

Glu Tyr Phe Ile Arg Val Phe Ala Ile Leu Lys Asn Lys Lys Ser Ile
                660             665             670

Pro Val Ser Ala Arg Val Ala Thr Tyr Leu Pro Ala Pro Glu Gly Leu
                675             680             685

Lys Phe Lys Ser Val Arg Glu Thr Ser Val Gln Val Glu Trp Asp Pro
690             695             700

Leu Ser Ile Ser Phe Asp Gly Trp Glu Leu Val Phe Arg Asn Met Gln
705             710             715             720

Lys Lys Asp Asp Asn Gly Asp Ile Thr Ser Ser Leu Lys Arg Pro Glu
                725             730             735

Thr Ser Tyr Met Gln Pro Gly Leu Ala Pro Gly Gln Gln Tyr Asn Val
                740             745             750

Ser Leu His Ile Val Lys Asn Asn Thr Arg Gly Pro Gly Leu Ser Arg
                755             760             765

Val Ile Thr Thr Lys Leu Asp Ala Pro Ser Gln Ile Glu Ala Lys Asp
                770             775             780

Val Thr Asp Thr Thr Ala Leu Ile Thr Trp Ser Lys Pro Leu Ala Glu
785             790             795             800
```

-continued

```
Ile Glu Gly Ile Glu Leu Thr Tyr Gly Pro Lys Asp Val Pro Gly Asp
            805                 810                 815
Arg Thr Thr Ile Asp Leu Ser Glu Asp Glu Asn Gln Tyr Ser Ile Gly
        820                 825                 830
Asn Leu Arg Pro His Thr Glu Tyr Glu Tyr Glu Val Thr Leu Ile Ser
            835                 840                 845
Arg Arg Gly Asp Met Glu Ser Asp Pro Ala Lys Glu Val Phe Val Thr
        850                 855                 860
Asp Leu Asp Ala Pro Arg Asn Leu Lys Arg Val Ser Gln Thr Asp Asn
865                 870                 875                 880
Ser Ile Thr Leu Glu Trp Lys Phe Ser His Ala Asn Ile Asp Asn Tyr
            885                 890                 895
Arg Ile Lys Phe Ala Pro Ile Ser Gly Gly Asp His Thr Glu Leu Thr
            900                 905                 910
Val Pro Lys Gly Asn Gln Ala Thr Arg Ala Thr Leu Thr Gly Leu
            915                 920                 925
Arg Pro Gly Thr Glu Tyr Gly Ile Gly Val Thr Ala Val Arg Gln Asp
        930                 935                 940
Arg Glu Ser Ala Pro Ala Thr Ile Asn Ala Gly Thr Asp Leu Asp Asn
945                 950                 955                 960
Pro Lys Asp Leu Glu Val Ser Asp Pro Thr Glu Thr Leu Ser Leu
            965                 970                 975
Arg Trp Arg Arg Pro Val Ala Lys Phe Asp Arg Tyr Arg Leu Thr Tyr
            980                 985                 990
Val Ser Pro Ser Gly Lys Lys Asn Glu Met Glu Ile Pro Val Asp Ser
            995                 1000                1005
Thr Ser Phe Ile Leu Arg Gly Leu Asp Ala Gly Thr Glu Tyr Thr Ile
    1010                1015                1020
Ser Leu Val Ala Glu Lys Gly Arg His Lys Ser Lys Pro Thr Thr Ile
1025                1030                1035                1040
Lys Gly Ser Thr Glu Glu Glu Pro Glu Leu Gly Asn Leu Ser Val Ser
            1045                1050                1055
Glu Thr Gly Trp Asp Gly Phe Gln Leu Thr Trp Thr Ala Ala Asp Gly
            1060                1065                1070
Ala Tyr Glu Asn Phe Val Ile Gln Val Gln Gln Ser Asp Asn Pro Glu
        1075                1080                1085
Glu Thr Trp Asn Ile Thr Val Pro Gly Gly Gln His Ser Val Asn Val
        1090                1095                1100
Thr Gly Leu Lys Ala Asn Thr Pro Tyr Asn Val Thr Leu Tyr Gly Val
1105                1110                1115                1120
Ile Arg Gly Tyr Arg Thr Lys Pro Leu Tyr Val Glu Thr Thr Thr Gly
            1125                1130                1135
Ala His Pro Glu Val Gly Glu Leu Thr Val Ser Asp Ile Thr Pro Glu
            1140                1145                1150
Ser Phe Asn Leu Ser Trp Thr Thr Thr Asn Gly Asp Phe Asp Ala Phe
        1155                1160                1165
Thr Ile Glu Ile Ile Asp Ser Asn Arg Leu Leu Glu Pro Met Glu Phe
    1170                1175                1180
Asn Ile Ser Gly Asn Ser Arg Thr Ala His Ile Ser Gly Leu Ser Pro
1185                1190                1195                1200
Ser Thr Asp Phe Ile Val Tyr Leu Tyr Gly Ile Ser His Gly Phe Arg
            1205                1210                1215
```

-continued

```
Thr Gln Ala Ile Ser Ala Ala Thr Thr Glu Ala Glu Pro Glu Val
            1220                1225                1230

Asp Asn Leu Leu Val Ser Asp Ala Thr Pro Asp Gly Phe Arg Leu Thr
            1235                1240                1245

Trp Thr Ala Asp Asp Gly Val Phe Asp Ser Phe Val Leu Lys Ile Arg
1250                1255                1260

Asp Thr Lys Arg Lys Ser Asp Pro Leu Glu Leu Ile Val Pro Gly His
1265                1270                1275                1280

Glu Arg Thr His Asp Ile Thr Gly Leu Lys Glu Gly Thr Glu Tyr Glu
            1285                1290                1295

Ile Glu Leu Tyr Gly Val Ser Ser Gly Arg Arg Ser Gln Pro Ile Asn
            1300                1305                1310

Ser Val Ala Thr Thr Val Val Gly Ser Pro Lys Gly Ile Ser Phe Ser
            1315                1320                1325

Asp Ile Thr Glu Asn Ser Ala Arg Val Ser Trp Thr Pro Pro Arg Ser
            1330                1335                1340

Arg Val Asp Ser Tyr Arg Val Ser Tyr Val Pro Ile Thr Gly Gly Thr
1345                1350                1355                1360

Pro Asn Val Val Thr Val Asp Gly Ser Lys Thr Arg Thr Lys Leu Val
            1365                1370                1375

Lys Leu Val Pro Gly Val Asp Tyr Asn Val Asn Ile Ile Ser Val Lys
            1380                1385                1390

Gly Phe Glu Glu Ser Glu Pro Ile Ser Gly Ile Leu Lys Thr Ala Leu
            1395                1400                1405

Asp Ser Pro Ser Gly Leu Val Val Met Asn Ile Thr Asp Ser Glu Ala
            1410                1415                1420

Leu Ala Thr Trp Gln Pro Ala Ile Ala Ala Val Asp Asn Tyr Ile Val
1425                1430                1435                1440

Ser Tyr Ser Ser Glu Asp Glu Pro Glu Val Thr Gln Met Val Ser Gly
            1445                1450                1455

Asn Thr Val Glu Tyr Asp Leu Asn Gly Leu Arg Pro Ala Thr Glu Tyr
            1460                1465                1470

Thr Leu Arg Val His Ala Val Lys Asp Ala Gln Lys Ser Glu Thr Leu
            1475                1480                1485

Ser Thr Gln Phe Thr Thr Gly Leu Asp Ala Pro Lys Asp Leu Ser Ala
            1490                1495                1500

Thr Glu Val Gln Ser Glu Thr Ala Val Ile Thr Trp Arg Pro Pro Arg
1505                1510                1515                1520

Ala Pro Val Thr Asp Tyr Leu Leu Thr Tyr Glu Ser Ile Asp Gly Arg
            1525                1530                1535

Val Lys Glu Val Ile Leu Asp Pro Glu Thr Thr Ser Tyr Thr Leu Thr
            1540                1545                1550

Glu Leu Ser Pro Ser Thr Gln Tyr Thr Val Lys Leu Gln Ala Leu Ser
            1555                1560                1565

Arg Ser Met Arg Ser Lys Met Ile Gln Thr Val Phe Thr Thr Thr Gly
            1570                1575                1580

Leu Leu Tyr Pro Tyr Pro Lys Asp Cys Ser Gln Ala Leu Leu Asn Gly
1585                1590                1595                1600

Glu Val Thr Ser Gly Leu Tyr Thr Ile Tyr Leu Asn Gly Asp Arg Thr
            1605                1610                1615

Gln Pro Leu Gln Val Phe Cys Asp Met Ala Glu Asp Gly Gly Gly Trp
            1620                1625                1630

Ile Val Phe Leu Arg Arg Gln Asn Gly Lys Glu Asp Phe Tyr Arg Asn
```

```
                 1635              1640              1645
Trp Lys Asn Tyr Val Ala Gly Phe Gly Asp Pro Lys Asp Glu Phe Trp
         1650              1655              1660
Ile Gly Leu Glu Asn Leu His Lys Ile Ser Ser Gln Gly Gln Tyr Glu
1665              1670              1675              1680
Leu Arg Val Asp Leu Arg Asp Arg Gly Glu Thr Ala Tyr Ala Val Tyr
             1685              1690              1695
Asp Lys Phe Ser Val Gly Asp Ala Lys Thr Arg Tyr Arg Leu Arg Val
         1700              1705              1710
Asp Gly Tyr Ser Gly Thr Ala Gly Asp Ser Met Thr Tyr His Asn Gly
         1715              1720              1725
Arg Ser Phe Ser Thr Phe Asp Lys Asp Asn Asp Ser Ala Ile Thr Asn
         1730              1735              1740
Cys Ala Leu Ser Tyr Lys Gly Ala Phe Trp Tyr Lys Asn Cys His Arg
1745              1750              1755              1760
Val Asn Leu Met Gly Arg Tyr Gly Asp Asn Asn His Ser Gln Gly Val
             1765              1770              1775
Asn Trp Phe His Trp Lys Gly His Glu Tyr Ser Ile Gln Phe Ala Glu
         1780              1785              1790
Met Lys Leu Arg Pro Ser Ser Phe Arg Asn Leu Glu Gly Arg Arg Lys
         1795              1800              1805
Arg Ala
   1810

<210> SEQ ID NO 5
<211> LENGTH: 89
<212> TYPE: PRT
<213> ORGANISM: Homo sapiens

<400> SEQUENCE: 5

Leu Asp Ala Pro Ser Gln Ile Glu Val Lys Asp Val Thr Asp Thr Thr
  1               5                  10                  15
Ala Leu Ile Thr Trp Phe Lys Pro Leu Ala Glu Ile Asp Gly Ile Glu
             20                  25                  30
Leu Thr Tyr Gly Ile Lys Asp Val Pro Gly Asp Arg Thr Thr Ile Asp
         35                  40                  45
Leu Thr Glu Asp Glu Asn Gln Tyr Ser Ile Gly Asn Leu Lys Pro Asp
     50                  55                  60
Thr Glu Tyr Glu Val Ser Leu Ile Ser Arg Arg Gly Asp Met Ser Ser
 65                  70                  75                  80
Asn Pro Ala Lys Glu Thr Phe Thr Thr
                 85

<210> SEQ ID NO 6
<211> LENGTH: 89
<212> TYPE: PRT
<213> ORGANISM: Gallus gallus

<400> SEQUENCE: 6

Leu Asp Ala Pro Ser His Ile Glu Val Lys Asp Val Thr Asp Thr Thr
  1               5                  10                  15
Ala Leu Ile Thr Trp Phe Lys Pro Leu Ala Glu Ile Asp Ser Ile Glu
             20                  25                  30
Leu Ser Tyr Gly Ile Lys Asp Val Pro Gly Asp Arg Thr Thr Ile Asp
         35                  40                  45
Leu Thr His Glu Asp Asn Gln Tyr Ser Ile Gly Asn Leu Arg Pro Asp
```

```
                50                  55                  60
Thr Glu Tyr Glu Val Ser Leu Ile Ser Arg Arg Val Asp Met Ala Ser
 65                  70                  75                  80

Asn Pro Ala Lys Glu Thr Phe Ile Thr
                 85
```

<210> SEQ ID NO 7
<211> LENGTH: 89
<212> TYPE: PRT
<213> ORGANISM: Mus musculus

<400> SEQUENCE: 7

```
Leu Asp Ala Pro Ser Gln Ile Glu Ala Lys Asp Val Thr Asp Thr Thr
 1               5                  10                  15

Ala Leu Ile Thr Trp Ser Lys Pro Leu Ala Glu Ile Glu Gly Ile Glu
                20                  25                  30

Leu Thr Tyr Gly Pro Lys Asp Val Pro Gly Asp Arg Thr Thr Ile Asp
                35                  40                  45

Leu Ser Glu Asp Glu Asn Gln Tyr Ser Ile Gly Asn Leu Arg Pro His
             50                  55                  60

Thr Glu Tyr Glu Val Thr Leu Ile Ser Arg Arg Gly Asp Met Glu Ser
 65                  70                  75                  80

Asp Pro Ala Lys Glu Val Phe Val Thr
                 85
```

<210> SEQ ID NO 8
<211> LENGTH: 89
<212> TYPE: PRT
<213> ORGANISM: Homo sapiens

<400> SEQUENCE: 8

```
Ala Met Gly Ser Pro Lys Glu Val Ile Phe Ser Asp Ile Thr Glu Asn
 1               5                  10                  15

Ser Ala Thr Val Ser Trp Arg Ala Pro Thr Ala Gln Val Glu Ser Phe
                20                  25                  30

Arg Ile Thr Tyr Val Pro Ile Thr Gly Gly Thr Pro Ser Met Val Thr
                35                  40                  45

Val Asp Gly Thr Lys Thr Gln Thr Arg Leu Val Lys Leu Ile Pro Gly
             50                  55                  60

Val Glu Tyr Leu Val Ser Ile Ile Ala Met Lys Gly Phe Glu Glu Ser
 65                  70                  75                  80

Glu Pro Val Ser Gly Ser Phe Thr Thr
                 85
```

<210> SEQ ID NO 9
<211> LENGTH: 89
<212> TYPE: PRT
<213> ORGANISM: Gallus gallus

<400> SEQUENCE: 9

```
Ala Met Gly Ser Pro Lys Glu Ile Met Phe Ser Asp Ile Thr Glu Asn
 1               5                  10                  15

Ala Ala Thr Val Ser Trp Arg Ala Pro Thr Ala Gln Val Glu Ser Phe
                20                  25                  30

Arg Ile Thr Tyr Val Pro Met Thr Gly Gly Ala Pro Ser Met Val Thr
                35                  40                  45

Val Asp Gly Thr Asp Thr Glu Thr Arg Leu Val Lys Leu Thr Pro Gly
             50                  55                  60
```

```
Val Glu Tyr Arg Val Ser Val Ile Ala Met Lys Gly Phe Glu Glu Ser
 65                  70                  75                  80

Asp Pro Val Ser Gly Thr Leu Ile Thr
                 85
```

<210> SEQ ID NO 10
<211> LENGTH: 89
<212> TYPE: PRT
<213> ORGANISM: Mus musculus

<400> SEQUENCE: 10

```
Val Val Gly Ser Pro Lys Gly Ile Ser Phe Ser Asp Ile Thr Glu Asn
  1               5                  10                  15

Ser Ala Thr Val Ser Trp Thr Pro Pro Arg Ser Arg Val Asp Ser Tyr
                 20                  25                  30

Arg Val Ser Tyr Val Pro Ile Thr Gly Gly Thr Pro Asn Val Val Thr
             35                  40                  45

Val Asp Gly Ser Lys Thr Arg Thr Lys Leu Val Lys Leu Val Pro Gly
         50                  55                  60

Val Asp Tyr Asn Val Asn Ile Ile Ser Val Lys Gly Phe Glu Glu Ser
 65                  70                  75                  80

Glu Pro Ile Ser Gly Ile Leu Lys Thr
                 85
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 11

```
Arg Gly Asp Ser Pro
  1               5
```

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 12

```
Arg Gly Asp Thr Pro
  1               5
```

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 13
taattggatc cgggatcgac tgttctgatg tgtct                               35

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: primer -continued

```
<400> SEQUENCE: 14
taattggaat tcagggggcat cgagttttgt ggttat                    36

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 15
taattggatc cgagtgataa cccaaaactc gatgc                      35

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 16
taattggaat tctggagcat ccaagtctgt gacaaa                     36

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 17
gcgggatccg acttggatgc tccacg                                26

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 18
gcggaattca gtgccagcat taatggtagc                            30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 19
gcgggatcga tcttgataac cccaaggac                             29

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 20
gcggaattca gtcgaaccct tgatggt                               27

<210> SEQ ID NO 21
<211> LENGTH: 27
```

```
<212> TYPE: DNA
<213> ORGANISM: Artificial Sequence
<220> FEATURE:
<223> OTHER INFORMATION: Description of Artificial Sequence: primer

<400> SEQUENCE: 21
gcgggatccg ttgtgggatc tcccaag                                               27

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 22
gcgctcgagt gttttcagaa ttccagaaat gggttcgc                                   38

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 23
taattggatc ccgaggaaga acctgagctt ggaaactta                                  39

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 24
taaaattgaa ttctgtggtt gctactgaat ttatgggttg ggagcg                          46

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 25

Arg Gly Asp Ser
  1

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 26
gcgggatcca aactcgatgc ccctagc                                               27

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 27
```

```
gcgctcgagt gtgacaaaga cctt                                              24
```

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 28

```
gcgctcgagg ttgtgggatc tcccaag                                           27
```

<210> SEQ ID NO 29
<211> LENGTH: 172
<212> TYPE: PRT
<213> ORGANISM: Gallus gallus

<400> SEQUENCE: 29

```
Leu Asp Ala Pro Ser Gln Ile Glu Ala Lys Asp Val Thr Asp Thr Thr
  1               5                  10                  15

Ala Leu Ile Thr Trp Ser Lys Pro Leu Ala Glu Ile Glu Gly Ile Glu
             20                  25                  30

Leu Thr Tyr Gly Pro Lys Asp Val Pro Gly Asp Arg Thr Thr Ile Asp
         35                  40                  45

Leu Ser Glu Asp Glu Asn Gln Tyr Ser Ile Gly Asn Leu Arg Pro His
     50                  55                  60

Thr Glu Tyr Glu Tyr Glu Val Thr Leu Ile Ser Arg Arg Gly Asp Met
 65                  70                  75                  80

Glu Ser Asp Pro Ala Lys Glu Val Phe Val Thr Val Val Gly Ser Pro
                 85                  90                  95

Lys Gly Ile Ser Phe Ser Asp Ile Thr Glu Asn Ser Ala Arg Val Ser
            100                 105                 110

Trp Thr Pro Pro Arg Ser Arg Val Asp Ser Tyr Arg Val Ser Tyr Val
            115                 120                 125

Pro Ile Thr Gly Gly Thr Pro Asn Val Val Thr Val Asp Gly Ser Lys
        130                 135                 140

Thr Arg Thr Lys Leu Val Lys Leu Val Pro Gly Val Asp Tyr Asn Val
145                 150                 155                 160

Asn Ile Ile Ser Val Lys Gly Phe Glu Glu Ser Glu
                165                 170
```

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 30

```
gggctggcaa gccacgtttg gtg                                               23
```